US011512131B2

(12) United States Patent
Miao et al.

(10) Patent No.: US 11,512,131 B2
(45) Date of Patent: *Nov. 29, 2022

(54) ANTI-PD-L1 ANTIBODY AND USES THEREOF

(71) Applicant: Innovent Biologics (Suzhou) Co., Ltd., Suzhou (CN)

(72) Inventors: Xiaoniu Miao, Suzhou (CN); Huajing Hu, Suzhou (CN); Junjian Liu, Suzhou (CN); Bingliang Chen, Suzhou (CN); Li Li, Suzhou (CN)

(73) Assignee: Innovent Biologics (Suzhou) Co., Ltd., Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/648,033

(22) PCT Filed: Dec. 27, 2018

(86) PCT No.: PCT/CN2018/124314
§ 371 (c)(1),
(2) Date: Mar. 17, 2020

(87) PCT Pub. No.: WO2019/129136
PCT Pub. Date: Jul. 4, 2019

(65) Prior Publication Data
US 2020/0332009 A1 Oct. 22, 2020

(30) Foreign Application Priority Data

Dec. 27, 2017 (CN) .................... 201711449321.X
Dec. 19, 2018 (CN) .................... 201811567281.3

(51) Int. Cl.
| | | |
|---|---|---|
| C07K 16/28 | (2006.01) | |
| A61P 35/00 | (2006.01) | |
| A61K 45/06 | (2006.01) | |
| A61K 39/00 | (2006.01) | |

(52) U.S. Cl.
CPC .......... *C07K 16/2827* (2013.01); *A61P 35/00* (2018.01); *A61K 45/06* (2013.01);
(Continued)

(58) Field of Classification Search
CPC ............ C07K 16/2827; C07K 16/2803; C07K 2317/24; C07K 2317/31; C07K 2317/565;
(Continued)

(56) References Cited

U.S. PATENT DOCUMENTS

| 4,737,456 A | 4/1988 | Weng |
| 4,816,567 A | 3/1989 | Cabilly et al. |

(Continued)

FOREIGN PATENT DOCUMENTS

| CN | 104470949 | 3/2015 |
| CN | 106478819 | 3/2017 |

(Continued)

OTHER PUBLICATIONS

U.S. Appl. No. 60/696,426, filed Jul. 1, 2005, Korman et al.
(Continued)

*Primary Examiner* — Joanne Hama
*Assistant Examiner* — Audrey L Buttice
(74) *Attorney, Agent, or Firm* — Fish & Richardson P.C.

(57) ABSTRACT

The invention relates to a novel antibody and an antibody fragment that specifically bind to PD-L1 and a composition comprising the antibody or the antibody fragment. In addition, the invention relates to a nucleic acid encoding the antibody or the antibody fragment thereof, a host cell comprising the nucleic acid, and a related use. Furthermore, the invention relates to a therapeutic and diagnostic use of these antibodies and antibody fragments. Particularly, the invention relates to a combined treatment of these antibodies and antibody fragments with other therapies.

37 Claims, 6 Drawing Sheets

Specification includes a Sequence Listing.

(52) U.S. Cl.
CPC .... *A61K 2039/507* (2013.01); *C07K 2317/24* (2013.01); *C07K 2317/31* (2013.01); *C07K 2317/565* (2013.01)

(58) Field of Classification Search
CPC ............ C07K 2317/76; C07K 2317/92; C07K 2317/56; A61P 35/00; A61P 35/02; A61K 45/06; A61K 2039/507; A61K 2039/505; A61K 31/7088; A61K 39/39558; A61K 39/395
See application file for complete search history.

(56) References Cited

U.S. PATENT DOCUMENTS

| | | | |
|---|---|---|---|
| 5,500,362 | A | 3/1996 | Robinson et al. |
| 5,624,821 | A | 4/1997 | Winter et al. |
| 5,648,237 | A | 7/1997 | Carter |
| 5,677,425 | A | 10/1997 | Bodmer et al. |
| 5,714,350 | A | 2/1998 | Co et al. |
| 5,789,199 | A | 8/1998 | Joly et al. |
| 5,821,337 | A | 10/1998 | Carter et al. |
| 5,840,523 | A | 11/1998 | Simmons et al. |
| 6,171,586 | B1 | 1/2001 | Lam et al. |
| 6,267,958 | B1 | 7/2001 | Andya et al. |
| 6,350,861 | B1 | 2/2002 | Co et al. |
| 6,737,056 | B1 | 5/2004 | Presta |
| 2004/0110704 | A1 | 6/2004 | Yamane et al. |
| 2010/0178684 | A1 | 7/2010 | Woo et al. |
| 2016/0108123 | A1* | 4/2016 | Freeman ................. A61P 37/02 435/69.6 |
| 2017/0204184 | A1* | 7/2017 | Zha .......................... A61P 33/00 |
| 2017/0355770 | A1* | 12/2017 | Wang ................. C07K 16/2827 |

FOREIGN PATENT DOCUMENTS

| | | |
|---|---|---|
| CN | 106939047 | 7/2017 |
| EP | 0154316 | 9/1985 |
| EP | 0401384 | 12/1990 |
| EP | 0404097 | 12/1990 |
| EP | 1176195 | 1/2002 |
| TW | 201620936 | 6/2016 |
| WO | WO 1991/00906 | 1/1991 |
| WO | WO 1991/10741 | 7/1991 |
| WO | WO 1992/03917 | 3/1992 |
| WO | WO 1992/03918 | 3/1992 |
| WO | WO 1993/01161 | 1/1993 |
| WO | WO 1994/04678 | 3/1994 |
| WO | WO 1999/54342 | 10/1999 |
| WO | WO 2003/035835 | 5/2003 |
| WO | WO 2003/086310 | 10/2003 |
| WO | WO 2005/120571 | 12/2005 |
| WO | WO 2006/044908 | 4/2006 |
| WO | WO 2006/057702 | 6/2006 |
| WO | WO 2006/089231 | 8/2006 |
| WO | WO 2010/077634 | 7/2010 |
| WO | WO 2012/177624 | 12/2012 |
| WO | WO 2014/008218 | 1/2014 |
| WO | WO 2014/100079 | 6/2014 |
| WO | WO 2015/138920 | 9/2015 |
| WO | WO 2015/153513 | 10/2015 |
| WO | WO 2016/007235 | 1/2016 |
| WO | WO 2016/028672 | 2/2016 |
| WO | WO 2016/061142 | 4/2016 |
| WO | WO 2017/215590 | 12/2017 |

OTHER PUBLICATIONS

U.S. Appl. No. 61/264,061, filed Nov. 24, 2009, Alimzhanov.
Al-Lazikani et al., "Standard conformations for the canonical structures of immunoglobulins", Journal of Molecular Biology, 273: 927-948, 1997.
Almagro and Fransson, "Humanization of antibodies", Frontiers in Bioscience 13: 1619-1633, 2008.
Altschul et al., "Basic local alignment search tool", J. Mol. Biol., 215: 403-10, 1990.
Altschul et al., "Gapped BLAST and PSI-BLAST: a new generation of protein database search programs", Nucleic Acids Res. 25: 3389-3402, 1997.
Armour et al., "Recombinant human IgG molecules lacking Fcgamma receptor I binding and monocyte triggering activities", Eur J Immunol., 29(8): 2613-24, 1999.
Bruggeman et al., "Human antibody production in transgenic mice: expression from 100 kb of the human IgH locus", Eur J Immunol 21: 1323-1326, 1991.
Charlton, "Expression and isolation of recombinant antibody fragments in *E. coli*", Methods in Molecular Biology, vol. 248, p. 245-254, 2003.
Chothia et al., "Conformations of immunoglobulin hypervariable regions", Nature 342: 877-883, 1989.
Clackson et al., "Making antibody fragments using phage display libraries", Nature 352: 624-628, 1991.
Clynes et al., "Fc receptors are required in passive and active immunity to melanoma", PNAS (USA) 95: 652-656, 1998.
Estep et al., "High throughput solution-based measurement of antibody-antigen affinity and epitope binning", MAbs, 5(2): 270-8, 2013.
Fellouse et al., "Synthetic antibodies from a four-amino-acid code: a dominant role for tyrosine in antigen recognition", PNAS, USA 101 (34): 12467-12472, 2004.
Flatman et al., "Process analytics for purification of monoclonal antibodies", J. Chromatogr., B848: 79-87, 2007.
Gemgross, "Advances in the production of human therapeutic proteins in yeasts and filamentous fungi", Nat. Biotech. 22: 1409-1414, 2004.
Graham et al., "Characteristics of a human cell line transformed by DNA from human adenovirus type 5", J. Gen Virol. 36: 59-74, 1977.
Green et al., "Antigen-specific human monoclonal antibodies from mice engineered with human Ig heavy and light chain YACs", Nature Genet. 7: 13-21, 1994.
Holliger et al., ""Diabodies": small bivalent and bispecific antibody fragments", Proc. Natl. Acad. Sci. USA 90 (14), 6444-6448, 1993.
Hoogenboom et al., "Overview of antibody phage-display technology and its applications", Methods in Molecular Biology 178: 1-37, 2002.
Hudson et al., "Engineered antibodies", Nat. Med. 9: 129-134, 2003.
Iwai et al., "PD-1 blockade inhibits hematogenous spread of poorly immunogenic tumor cells by enhanced recruitment of effector T cells", Int. Immunol. 17: 133-144, 2005.
Lee et al., "Bivalent antibody phage display mimics natural immunoglobulin", J. Immunol.Methods 284(1-2): 119-132, 2004.
Lee et al., "High-affinity human antibodies from phage-displayed synthetic Fab libraries with a single framework scaffold", J. Mol. Biol 340(5): 1073-1093, 2004.
Li et al., "Optimization of humanized IgGs in glycoengineered Pichia pastoris", Nat. Biotech. 24: 210-215, 2006.
Lonberg et al., "Pillars Article: Three-Dimensional Structure of a Human Class II Histocompatibility Molecule Complexed with Superantigen. Nature. 1994, 368: 711-718", Nature 368: 856-859, 1994.
Lonberg, "Fully human antibodies from transgenic mouse and phage display platforms", Curr. Opin. Immunol 20: 450-459, 2008.
Marks et al., "By-passing immunization. Human antibodies from V-gene libraries displayed on phage", J.Mol.Biol. 222: 581-597, 1991.
Marks et al., "Selection of human antibodies from phage display libraries", Methods in Molecular Biology, 2004, 248:161-175.
McCafferty et al., "Phage antibodies: filamentous phage displaying antibody variable domains", Nature 348: 552-554, 1990.
Meyers and W. Miller, "Optimal alignments in linear space", CABIOS, 4: 11-17, 1989.
Morrison et al., "Chimeric human antibody molecules: mouse antigen-binding domains with human constant region domains", Proc. Natl. Acad. Sci. USA 81: 6851-6855, 1984.

(56) References Cited

OTHER PUBLICATIONS

PCT International Preliminary Report on Patentability in International Application No. PCT/CN2018/124314, dated Mar. 20, 2019, 6 pages.

Pluckthun, "The Pharmacology of Monoclonal Antibodies," Springer-Verlag, 1994, 113:269-315.

Portolano et al., "Lack of promiscuity in autoantigen-specific H and L chain combinations as revealed by human H and L chain" roulette, J. Immunol., 1993, 150: 880-887.

Presta, "Selection, design, and engineering of therapeutic antibodies," J. Allergy Clin. Immunol., 2005, 116(4):731-735.

Ravetch and Kinet, "Fc receptors", Annu. Rev. Immunol. 9: 457-92, 1991.

Shields et al., "Lack of fucose on human IgG1 N-linked oligosaccharide improves binding to human FcγRIII and antibody-dependent cellular toxicity", J. Biol. Chem 277: 26733-26740, 2002.

Sidhu et al., "Phage-displayed antibody libraries of synthetic heavy chain complementarity determining regions", J. Mol. Biol. 338(2): 299-310, 2004.

Stahli et al., "Distinction of epitopes by monoclonal antibodies", Methods in Enzymology, 9: 242-253, 1983.

Tarentino et al., "The isolation and structure of the core oligosaccharide sequences of IgM", Biochem. 14: 5516-23, 1975.

Tuaillon et al., "Human immunoglobulin heavy-chain minilocus recombination in transgenic mice: gene-segment use in mu and gamma transcripts.", PNAS 90: 3720-3724, 1993.

Umana et al., "Engineered glycoforms of an antineuroblastoma IgG1 with optimized antibody-dependent cellular cytotoxic activity", Nat. Biotech, 17: 176-180, 1999.

Urlaub et al., "Isolation of Chinese hamster cell mutants deficient in dihydrofolate reductase activity", Proc. Natl. Acad. Sci. USA 77: 216, 1980.

van Dijk and van de Winkel, "Human antibodies as next generation therapeutics", Curr. Opin. Pharmacol, 5: 368-74, 2001.

Yamada et al., "Next-generation peptide vaccines for advanced cancer," Cancer Sci, , Jan. 2013, 104: 15-21.

Yamane-Ohnuki et al., "Establishment of FUT8 knockout Chinese hamster ovary cells: an ideal host cell line for producing completely defucosylated antibodies with enhanced antibody-dependent cellular cytotoxicity", Biotechnol Bioeng 87: 614-22, 2004.

\* cited by examiner

SEQUENCE LISTING

```
<160> NUMBER OF SEQ ID NOS: 126

<210> SEQ ID NO 1
<211> LENGTH: 7
<212> TYPE: PRT
<213> ORGANISM: Artificial
<220> FEATURE:
<223> OTHER INFORMATION: Synthetic construct

<400> SEQUENCE: 1

Gly Phe Asn Ile Glu Asp Thr
1               5

<210> SEQ ID NO 2
<211> LENGTH: 7
<212> TYPE: PRT
<213> ORGANISM: Artificial
<220> FEATURE:
<223> OTHER INFORMATION: Synthetic construct

<400> SEQUENCE: 2

Gly Asp Ser Ile Thr Ser Gly
1               5

<210> SEQ ID NO 3
<211> LENGTH: 7
<212> TYPE: PRT
<213> ORGANISM: Artificial
<220> FEATURE:
<223> OTHER INFORMATION: Synthetic construct

<400> SEQUENCE: 3

Gly Tyr Thr Phe Thr Thr Tyr
1               5

<210> SEQ ID NO 4
<211> LENGTH: 7
<212> TYPE: PRT
<213> ORGANISM: Artificial
<220> FEATURE:
```

```
<223> OTHER INFORMATION: Synthetic construct
<220> FEATURE:
<221> NAME/KEY: misc_feature
<222> LOCATION: (1)..(1)
<223> OTHER INFORMATION: Xaa can be G
<220> FEATURE:
<221> NAME/KEY: misc_feature
<222> LOCATION: (2)..(2)
<223> OTHER INFORMATION: Xaa can be D, F or Y
<220> FEATURE:
<221> NAME/KEY: misc_feature
<222> LOCATION: (3)..(3)
<223> OTHER INFORMATION: Xaa can be N, S or T.
<220> FEATURE:
<221> NAME/KEY: misc_feature
<222> LOCATION: (4)..(4)
<223> OTHER INFORMATION: Xaa can be I or F
<220> FEATURE:
<221> NAME/KEY: misc_feature
<222> LOCATION: (5)..(5)
<223> OTHER INFORMATION: Xaa can be T or E
<220> FEATURE:
<221> NAME/KEY: misc_feature
<222> LOCATION: (6)..(6)
<223> OTHER INFORMATION: Xaa can be S, D or T
<220> FEATURE:
<221> NAME/KEY: misc_feature
<222> LOCATION: (7)..(7)
<223> OTHER INFORMATION: Xaa can be G, T or Y

<400> SEQUENCE: 4

Xaa Xaa Xaa Xaa Xaa Xaa Xaa
1               5

<210> SEQ ID NO 5
<211> LENGTH: 6
<212> TYPE: PRT
<213> ORGANISM: Artificial
<220> FEATURE:
<223> OTHER INFORMATION: Synthetic construct

<400> SEQUENCE: 5

Asp Pro Ala Asn Asp Asp
1               5

<210> SEQ ID NO 6
<211> LENGTH: 5
<212> TYPE: PRT
<213> ORGANISM: Artificial
<220> FEATURE:
<223> OTHER INFORMATION: Synthetic construct

<400> SEQUENCE: 6

Ser Tyr Thr Gly Ser
1               5

<210> SEQ ID NO 7
<211> LENGTH: 5
<212> TYPE: PRT
<213> ORGANISM: Artificial
<220> FEATURE:
<223> OTHER INFORMATION: Synthetic construct

<400> SEQUENCE: 7

Ser Tyr Ser Gly Ser
1               5

<210> SEQ ID NO 8
<211> LENGTH: 6
<212> TYPE: PRT
<213> ORGANISM: Artificial
```

```
<220> FEATURE:
<223> OTHER INFORMATION: Synthetic construct

<400> SEQUENCE: 8

Asn Pro Asn Ser Asp Tyr
1               5

<210> SEQ ID NO 9
<211> LENGTH: 5
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa can be T or S

<400> SEQUENCE: 9

Ser Tyr Xaa Gly Ser
1               5

<210> SEQ ID NO 10
<211> LENGTH: 8
<212> TYPE: PRT
<213> ORGANISM: Artificial
<220> FEATURE:
<223> OTHER INFORMATION: Synthetic construct

<400> SEQUENCE: 10

Gly Leu Gly Arg Trp Phe Ala Tyr
1               5

<210> SEQ ID NO 11
<211> LENGTH: 10
<212> TYPE: PRT
<213> ORGANISM: Artificial
<220> FEATURE:
<223> OTHER INFORMATION: Synthetic construct

<400> SEQUENCE: 11

Ala Pro Pro Trp Leu Ser Ala Met Asp Tyr
1               5                   10

<210> SEQ ID NO 12
<211> LENGTH: 10
<212> TYPE: PRT
<213> ORGANISM: Artificial
<220> FEATURE:
<223> OTHER INFORMATION: Synthetic construct

<400> SEQUENCE: 12

Gly Asp Leu Trp Pro Pro Trp Phe Ala Tyr
1               5                   10

<210> SEQ ID NO 13
<211> LENGTH: 5
<212> TYPE: PRT
<213> ORGANISM: Artificial
<220> FEATURE:
<223> OTHER INFORMATION: Synthetic construct

<400> SEQUENCE: 13

Gln Ser Phe Asp Tyr
1               5

<210> SEQ ID NO 14
```

```
<211> LENGTH: 11
<212> TYPE: PRT
<213> ORGANISM: Artificial
<220> FEATURE:
<223> OTHER INFORMATION: Synthetic construct

<400> SEQUENCE: 14

Lys Ala Ser Gln Asp Val Ile Asn Ala Val Ala
1               5                   10

<210> SEQ ID NO 15
<211> LENGTH: 17
<212> TYPE: PRT
<213> ORGANISM: Artificial
<220> FEATURE:
<223> OTHER INFORMATION: Synthetic construct

<400> SEQUENCE: 15

Lys Ser Ser Gln Ser Leu Leu Tyr Ser Ser Asn Gln Lys Asn Ser Leu
1               5                   10                  15

Ala

<210> SEQ ID NO 16
<211> LENGTH: 15
<212> TYPE: PRT
<213> ORGANISM: Artificial
<220> FEATURE:
<223> OTHER INFORMATION: Synthetic construct

<400> SEQUENCE: 16

Arg Ala Ser Glu Ser Val Glu Phe Tyr Gly Thr Ser Leu Leu Gln
1               5                   10                  15

<210> SEQ ID NO 17
<211> LENGTH: 7
<212> TYPE: PRT
<213> ORGANISM: Artificial
<220> FEATURE:
<223> OTHER INFORMATION: Synthetic construct

<400> SEQUENCE: 17

Ser Ala Ser Asn Arg Tyr Thr
1               5

<210> SEQ ID NO 18
<211> LENGTH: 7
<212> TYPE: PRT
<213> ORGANISM: Artificial
<220> FEATURE:
<223> OTHER INFORMATION: Synthetic construct

<400> SEQUENCE: 18

Trp Ala Ser Thr Arg Glu Ser
1               5

<210> SEQ ID NO 19
<211> LENGTH: 7
<212> TYPE: PRT
<213> ORGANISM: Artificial
<220> FEATURE:
<223> OTHER INFORMATION: Synthetic construct

<400> SEQUENCE: 19

Ala Ala Ser Asn Val Glu Ser
1               5
```

```
<210> SEQ ID NO 20
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be S, W or A
<220> FEATURE:
<221> NAME/KEY: misc_feature
<222> LOCATION: (2)..(2)
<223> OTHER INFORMATION: Xaa can be A
<220> FEATURE:
<221> NAME/KEY: misc_feature
<222> LOCATION: (3)..(3)
<223> OTHER INFORMATION: Xaa can be S
<220> FEATURE:
<221> NAME/KEY: misc_feature
<222> LOCATION: (4)..(4)
<223> OTHER INFORMATION: Xaa can be N or T
<220> FEATURE:
<221> NAME/KEY: misc_feature
<222> LOCATION: (5)..(5)
<223> OTHER INFORMATION: Xaa can be R or V
<220> FEATURE:
<221> NAME/KEY: misc_feature
<222> LOCATION: (6)..(6)
<223> OTHER INFORMATION: Xaa can be Y or E
<220> FEATURE:
<221> NAME/KEY: misc_feature
<222> LOCATION: (7)..(7)
<223> OTHER INFORMATION: Xaa can be T or S

<400> SEQUENCE: 20

Xaa Xaa Xaa Xaa Xaa Xaa Xaa
1               5

<210> SEQ ID NO 21
<211> LENGTH: 9
<212> TYPE: PRT
<213> ORGANISM: Artificial
<220> FEATURE:
<223> OTHER INFORMATION: Synthetic construct

<400> SEQUENCE: 21

Gln Gln His Tyr Ser Pro Pro Leu Thr
1               5

<210> SEQ ID NO 22
<211> LENGTH: 9
<212> TYPE: PRT
<213> ORGANISM: Artificial
<220> FEATURE:
<223> OTHER INFORMATION: Synthetic construct

<400> SEQUENCE: 22

Gln Gln Tyr Tyr Ser Tyr Pro Trp Thr
1               5

<210> SEQ ID NO 23
<211> LENGTH: 9
<212> TYPE: PRT
<213> ORGANISM: Artificial
<220> FEATURE:
<223> OTHER INFORMATION: Synthetic construct

<400> SEQUENCE: 23

Gln Gln Tyr Tyr Gly Tyr Pro Leu Thr
1               5
```

<210> SEQ ID NO 24
<211> LENGTH: 9
<212> TYPE: PRT
<213> ORGANISM: Artificial
<220> FEATURE:
<223> OTHER INFORMATION: Synthetic construct

<400> SEQUENCE: 24

His Gln Gly Arg Lys Val Pro Tyr Thr
1               5

<210> SEQ ID NO 25
<211> LENGTH: 9
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be Q or H
<220> FEATURE:
<221> NAME/KEY: misc_feature
<222> LOCATION: (2)..(2)
<223> OTHER INFORMATION: Xaa can be Q
<220> FEATURE:
<221> NAME/KEY: misc_feature
<222> LOCATION: (3)..(3)
<223> OTHER INFORMATION: Xaa can be H, Y or G
<220> FEATURE:
<221> NAME/KEY: misc_feature
<222> LOCATION: (4)..(4)
<223> OTHER INFORMATION: Xaa can be Y or R
<220> FEATURE:
<221> NAME/KEY: misc_feature
<222> LOCATION: (5)..(5)
<223> OTHER INFORMATION: Xaa can be S, G or K
<220> FEATURE:
<221> NAME/KEY: misc_feature
<222> LOCATION: (6)..(6)
<223> OTHER INFORMATION: Xaa can be P, Y or V
<220> FEATURE:
<221> NAME/KEY: misc_feature
<222> LOCATION: (7)..(7)
<223> OTHER INFORMATION: Xaa can be P
<220> FEATURE:
<221> NAME/KEY: misc_feature
<222> LOCATION: (8)..(8)
<223> OTHER INFORMATION: Xaa can be L, W or Y
<220> FEATURE:
<221> NAME/KEY: misc_feature
<222> LOCATION: (9)..(9)
<223> OTHER INFORMATION: Xaa can be T

<400> SEQUENCE: 25

Xaa Xaa Xaa Xaa Xaa Xaa Xaa Xaa Xaa
1               5

<210> SEQ ID NO 26
<211> LENGTH: 117
<212> TYPE: PRT
<213> ORGANISM: Artificial
<220> FEATURE:
<223> OTHER INFORMATION: Synthetic construct

<400> SEQUENCE: 26

Glu Val Gln Leu Gln Gln Ser Val Ala Glu Leu Val Lys Pro Gly Ala
1               5                   10                  15

Ser Val Lys Leu Ser Cys Thr Ala Ser Gly Phe Asn Ile Glu Asp Thr
            20                  25                  30

Tyr Ile His Trp Val Lys Gln Arg Pro Glu Gln Gly Leu Glu Trp Ile

```
                   35                  40                  45
Gly Arg Ile Asp Pro Ala Asn Asp Asp Thr Lys Tyr Asp Pro Lys Phe
            50                  55                  60
Gln Gly Lys Ala Thr Ile Thr Ala Asp Thr Ser Ser Asn Thr Ala Tyr
65                  70                  75                  80
Leu Gln Leu Ser Ser Leu Thr Pro Glu Asp Thr Ala Val Tyr Tyr Cys
                85                  90                  95
Gly Arg Gly Leu Gly Arg Trp Phe Ala Tyr Trp Gly Gln Gly Thr Leu
                100                 105                 110
Val Thr Val Ser Ala
            115

<210> SEQ ID NO 27
<211> LENGTH: 118
<212> TYPE: PRT
<213> ORGANISM: Artificial
<220> FEATURE:
<223> OTHER INFORMATION: Synthetic construct

<400> SEQUENCE: 27

Glu Val Gln Leu Gln Gln Ser Gly Pro Ser Leu Val Lys Pro Ser Gln
1               5                   10                  15
Thr Leu Ser Leu Thr Cys Ser Val Thr Gly Asp Ser Ile Thr Ser Gly
            20                  25                  30
Tyr Trp Asn Trp Ile Arg Glu Phe Pro Gly Asn Lys Leu Glu Tyr Leu
                35                  40                  45
Gly Tyr Ile Ser Tyr Thr Gly Ser Thr Tyr Tyr Asn Pro Ser Leu Lys
            50                  55                  60
Ser Arg Ile Ser Ile Thr Arg Asp Thr Ser Lys Asn Gln Tyr Ser Leu
65                  70                  75                  80
Gln Leu Asn Ser Val Thr Thr Glu Asp Thr Ala Thr Tyr Tyr Cys Ala
                85                  90                  95
Lys Ala Pro Arg Trp Leu Ser Ala Met Asp Tyr Trp Gly Gln Gly Thr
                100                 105                 110
Ser Val Thr Val Ser Ser
            115

<210> SEQ ID NO 28
<211> LENGTH: 118
<212> TYPE: PRT
<213> ORGANISM: Artificial
<220> FEATURE:
<223> OTHER INFORMATION: Synthetic construct

<400> SEQUENCE: 28

Gln Val Gln Leu Lys Glu Ser Gly Pro Ser Leu Val Lys Pro Ser Gln
1               5                   10                  15
Thr Leu Ser Leu Thr Cys Ser Val Thr Gly Asp Ser Ile Thr Ser Gly
            20                  25                  30
Tyr Trp Asn Trp Ile Arg Lys Phe Pro Gly Asn Lys Leu Glu Tyr Met
                35                  40                  45
Gly Tyr Ile Ser Tyr Ser Gly Ser Thr Tyr His Asn Pro Ser Leu Lys
            50                  55                  60
Ser Arg Ile Ser Ile Thr Arg Asp Thr Ser Lys Asn Gln Phe Tyr Leu
65                  70                  75                  80
Gln Leu Asn Ser Val Thr Lys Glu Asp Thr Ala Thr Tyr Tyr Cys Ala
                85                  90                  95
```

```
Arg Gly Asp Leu Trp Pro Pro Trp Phe Ala Tyr Trp Gly Gln Gly Thr
                100                 105                 110

Leu Val Thr Val Ser Ala
            115
```

<210> SEQ ID NO 29
<211> LENGTH: 114
<212> TYPE: PRT
<213> ORGANISM: Artificial
<220> FEATURE:
<223> OTHER INFORMATION: Synthetic construct

<400> SEQUENCE: 29

```
Glu Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
                20                  25                  30

Thr Met His Trp Val Lys Gln Arg Pro Gly Gln Gly Leu Glu Trp Ile
            35                  40                  45

Gly Asn Ile Asn Pro Asn Ser Asp Tyr Ala Ile Tyr Asn Gln Lys Phe
        50                  55                  60

Lys Asp Lys Ala Thr Leu Thr Ala Asp Lys Ser Ser Asn Thr Ala Tyr
65                  70                  75                  80

Met Gln Leu Ser Gly Leu Thr Ser Glu Asp Ser Ala Val Tyr Tyr Cys
                85                  90                  95

Ala Lys Gln Ser Phe Asp Tyr Trp Gly Gln Gly Thr Thr Leu Thr Val
                100                 105                 110

Ser Ser
```

<210> SEQ ID NO 30
<211> LENGTH: 117
<212> TYPE: PRT
<213> ORGANISM: Artificial
<220> FEATURE:
<223> OTHER INFORMATION: Synthetic construct

<400> SEQUENCE: 30

```
Glu Val Gln Leu Val Gln Ser Gly Ala Glu Val Lys Lys Pro Gly Ala
1               5                   10                  15

Thr Val Lys Ile Ser Cys Thr Ala Ser Gly Phe Asn Ile Glu Asp Thr
                20                  25                  30

Tyr Ile His Trp Val Gln Gln Ala Pro Gly Gln Gly Leu Glu Trp Ile
            35                  40                  45

Gly Arg Ile Asp Pro Ala Asn Asp Asp Thr Lys Tyr Ala Pro Lys Phe
        50                  55                  60

Gln Gly Arg Ala Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Gly Arg Gly Leu Gly Arg Trp Phe Ala Tyr Trp Gly Gln Gly Thr Leu
                100                 105                 110

Val Thr Val Ser Ser
            115
```

<210> SEQ ID NO 31
<211> LENGTH: 114
<212> TYPE: PRT
<213> ORGANISM: Artificial
<220> FEATURE:

<223> OTHER INFORMATION: Synthetic construct

<400> SEQUENCE: 31

Gln Val Gln Leu Val Gln Ser Gly Ala Glu Val Ala Lys Pro Gly Ala
1               5                   10                  15

Ser Val Lys Val Ser Cys Lys Ala Ser Gly Tyr Thr Phe Thr Thr Tyr
            20                  25                  30

Thr Met His Trp Val Arg Gln Arg Pro Gly Gln Gly Leu Glu Trp Ile
        35                  40                  45

Gly Asn Ile Asn Pro Asn Ser Asp Tyr Ala Ile Tyr Ala Gln Lys Phe
    50                  55                  60

Gln Gly Arg Ala Thr Met Thr Ala Asp Lys Ser Thr Asn Thr Ala Tyr
65                  70                  75                  80

Met Glu Leu Ser Ser Leu Arg Ser Glu Asp Ser Ala Val Tyr Tyr Cys
                85                  90                  95

Ala Lys Gln Ser Phe Asp Tyr Trp Gly Gln Gly Thr Leu Val Thr Val
            100                 105                 110

Ser Ser

<210> SEQ ID NO 32
<211> LENGTH: 107
<212> TYPE: PRT
<213> ORGANISM: Artificial
<220> FEATURE:
<223> OTHER INFORMATION: Synthetic construct

<400> SEQUENCE: 32

Ser Ile Val Met Thr Gln Ser His Lys Phe Met Ser Thr Ser Ile Gly
1               5                   10                  15

Asp Arg Val Asn Ile Ser Cys Lys Ala Ser Gln Asp Val Ile Asn Ala
            20                  25                  30

Val Ala Trp Cys Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Leu
                85                  90                  95

Thr Phe Gly Gly Gly Thr Lys Leu Glu Leu Lys
            100                 105

<210> SEQ ID NO 33
<211> LENGTH: 113
<212> TYPE: PRT
<213> ORGANISM: Artificial
<220> FEATURE:
<223> OTHER INFORMATION: Synthetic construct

<400> SEQUENCE: 33

Asp Ile Val Met Ser Gln Ser Pro Ser Ser Leu Ala Val Ser Val Gly
1               5                   10                  15

Glu Lys Ile Thr Met Ser Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

-continued

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Trp Thr Phe Gly Gly Gly Thr Lys Leu Glu Ile
            100                 105                 110

Lys

<210> SEQ ID NO 34
<211> LENGTH: 113
<212> TYPE: PRT
<213> ORGANISM: Artificial
<220> FEATURE:
<223> OTHER INFORMATION: Synthetic construct

<400> SEQUENCE: 34

Asn Ile Val Met Thr Gln Thr Pro Ser Ser Leu Ala Val Ser Val Gly
1               5                   10                  15

Glu Lys Ile Thr Met Ser Cys Lys Ser Ser Gln Ser Leu Leu Tyr Ser
                20                  25                  30

Ser Asn Gln Lys Asn Ser Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Glu Ala Glu Asp Leu Ala Val Tyr Tyr Cys Gln Gln
                85                  90                  95

Tyr Tyr Gly Tyr Pro Leu Thr Phe Gly Ala Gly Thr Lys Leu Glu Leu
            100                 105                 110

Lys

<210> SEQ ID NO 35
<211> LENGTH: 111
<212> TYPE: PRT
<213> ORGANISM: Artificial
<220> FEATURE:
<223> OTHER INFORMATION: Synthetic construct

<400> SEQUENCE: 35

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Phe Tyr
                20                  25                  30

Gly Thr Ser Leu Leu Gln Trp Tyr Gln Gln Lys Pro Gly Gln Pro Pro
            35                  40                  45

Lys Leu Leu Ile Tyr Ala Ala Ser Asn Val Glu Ser Gly Val Pro Ala
        50                  55                  60

Arg Phe Ser Gly Ser Gly Ser Gly Thr Asp Phe Ser Leu Asn Ile His
65                  70                  75                  80

Pro Val Glu Val Asp Asp Val Ala Leu Tyr Phe Cys His Gln Gly Arg
                85                  90                  95

Lys Val Pro Tyr Thr Phe Gly Gly Gly Thr Lys Leu Glu Ile Lys
            100                 105                 110

<210> SEQ ID NO 36
<211> LENGTH: 107

```
<212> TYPE: PRT
<213> ORGANISM: Artificial
<220> FEATURE:
<223> OTHER INFORMATION: Synthetic construct

<400> SEQUENCE: 36

Gly Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ile Asn Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Leu Ala Val Tyr Tyr Cys Gln Gln His Tyr Ser Pro Pro Leu
                85                  90                  95

Thr Phe Gly Gly Gly Thr Lys Val Glu Ile Lys
            100                 105

<210> SEQ ID NO 37
<211> LENGTH: 111
<212> TYPE: PRT
<213> ORGANISM: Artificial
<220> FEATURE:
<223> OTHER INFORMATION: Synthetic construct

<400> SEQUENCE: 37

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Glu Phe Tyr
            20                  25                  30

Gly Thr Ser Leu Leu Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asp Asp Thr Ala Asn Tyr Tyr Cys His Gln Gly Arg
                85                  90                  95

Lys Val Pro Tyr Thr Phe Gly Gln Gly Thr Lys Leu Glu Ile Lys
            100                 105                 110

<210> SEQ ID NO 38
<211> LENGTH: 447
<212> TYPE: PRT
<213> ORGANISM: Artificial
<220> FEATURE:
<223> OTHER INFORMATION: Synthetic construct

<400> SEQUENCE: 38

Glu Val Gln Leu Gln Gln Ser Val Ala Glu Leu Val Lys Pro Gly Ala
1               5                   10                  15

Ser Val Lys Leu Ser Cys Thr Ala Ser Gly Phe Asn Ile Glu Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Asp Asp Thr Lys Tyr Asp Pro Lys Phe
```

```
            50                  55                  60
Gln Gly Lys Ala Thr Ile Thr Ala Asp Thr Ser Ser Asn Thr Ala Tyr
 65                  70                  75                  80

Leu Gln Leu Ser Ser Leu Thr Pro Glu Asp Thr Ala Val Tyr Tyr Cys
                 85                  90                  95

Gly Arg Gly Leu Gly Arg Trp Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 39
<211> LENGTH: 448
<212> TYPE: PRT
<213> ORGANISM: Artificial
```

<220> FEATURE:
<223> OTHER INFORMATION: Synthetic construct

<400> SEQUENCE: 39

```
Glu Val Gln Leu Gln Gln Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Glu Phe Pro Gly Asn Lys Leu Glu Tyr Leu
        35                  40                  45

Gly Tyr Ile Ser Tyr Thr Gly Ser Thr Tyr Tyr Asn Pro Ser Leu Lys
    50                  55                  60

Ser Arg Ile Ser Ile Thr Arg Asp Thr Ser Lys Asn Gln Tyr Ser Leu
65                  70                  75                  80

Gln Leu Asn Ser Val Thr Thr Glu Asp Thr Ala Thr Tyr Tyr Cys Ala
                85                  90                  95

Lys Ala Pro Arg Trp Leu Ser Ala Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 40
<211> LENGTH: 448
<212> TYPE: PRT
<213> ORGANISM: Artificial
<220> FEATURE:
<223> OTHER INFORMATION: Synthetic construct

<400> SEQUENCE: 40

Gln Val Gln Leu Lys Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ser Thr Tyr His Asn Pro Ser Leu Lys
50                  55                  60

Ser Arg Ile Ser Ile Thr Arg Asp Thr Ser Lys Asn Gln Phe Tyr Leu
65                  70                  75                  80

Gln Leu Asn Ser Val Thr Lys Glu Asp Thr Ala Thr Tyr Tyr Cys Ala
            85                  90                  95

Arg Gly Asp Leu Trp Pro Pro Trp Phe Ala Tyr Trp Gly Gln Gly Thr
            100                 105                 110

Leu Val Thr Val Ser Ala Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
            290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 41
<211> LENGTH: 444
<212> TYPE: PRT
<213> ORGANISM: Artificial
<220> FEATURE:
<223> OTHER INFORMATION: Synthetic construct

<400> SEQUENCE: 41

Glu Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
                20                  25                  30

Thr Met His Trp Val Lys Gln Arg Pro Gly Gln Gly Leu Glu Trp Ile
                35                  40                  45

Gly Asn Ile Asn Pro Asn Ser Asp Tyr Ala Ile Tyr Asn Gln Lys Phe
            50                  55                  60

Lys Asp Lys Ala Thr Leu Thr Ala Asp Lys Ser Ser Asn Thr Ala Tyr
65                  70                  75                  80

Met Gln Leu Ser Gly Leu Thr Ser Glu Asp Ser Ala Val Tyr Tyr Cys
                85                  90                  95

Ala Lys Gln Ser Phe Asp Tyr Trp Gly Gln Gly Thr Thr Leu Thr Val
                100                 105                 110

Ser Ser Ala Ser Thr Lys Gly Pro Ser Val Phe Pro Leu Ala Pro Ser
                115                 120                 125

Ser Lys Ser Thr Ser Gly Gly Thr Ala Ala Leu Gly Cys Leu Val Lys
                130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
                195                 200                 205

Asp Lys Lys Val Glu Pro Lys Ser Cys Asp Lys Thr His Thr Cys Pro
                210                 215                 220

Pro Cys Pro Ala Pro Glu Leu Leu Gly Gly Pro Ser Val Phe Leu Phe
225                 230                 235                 240
```

```
Pro Pro Lys Pro Lys Asp Thr Leu Met Ile Ser Arg Thr Pro Glu Val
            245                 250                 255
Thr Cys Val Val Val Asp Val Ser His Glu Asp Pro Glu Val Lys Phe
        260                 265                 270
Asn Trp Tyr Val Asp Gly Val Glu Val His Asn Ala Lys Thr Lys Pro
        275                 280                 285
Arg Glu Glu Gln Tyr Ala Ser Thr Tyr Arg Val Val Ser Val Leu Thr
    290                 295                 300
Val Leu His Gln Asp Trp Leu Asn Gly Lys Glu Tyr Lys Cys Lys Val
305                 310                 315                 320
Ser Asn Lys Ala Leu Pro Ala Pro Ile Glu Lys Thr Ile Ser Lys Ala
                325                 330                 335
Lys Gly Gln Pro Arg Glu Pro Gln Val Tyr Thr Leu Pro Pro Ser Arg
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly Lys
            435                 440

<210> SEQ ID NO 42
<211> LENGTH: 447
<212> TYPE: PRT
<213> ORGANISM: Artificial
<220> FEATURE:
<223> OTHER INFORMATION: Synthetic construct

<400> SEQUENCE: 42

Glu Val Gln Leu Val Gln Ser Gly Ala Glu Val Lys Lys Pro Gly Ala
1               5                   10                  15
Thr Val Lys Ile Ser Cys Thr Ala Ser Gly Phe Asn Ile Glu Asp Thr
            20                  25                  30
Tyr Ile His Trp Val Gln Gln Ala Pro Gly Gln Gly Leu Glu Trp Ile
        35                  40                  45
Gly Arg Ile Asp Pro Ala Asn Asp Asp Thr Lys Tyr Ala Pro Lys Phe
    50                  55                  60
Gln Gly Arg Ala Thr Ile Thr Ala Asp Thr Ser Thr Asp Thr Ala Tyr
65                  70                  75                  80
Met Glu Leu Ser Ser Leu Arg Ser Glu Asp Thr Ala Val Tyr Tyr Cys
                85                  90                  95
Gly Arg Gly Leu Gly Arg Trp Phe Ala Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
```

Gly Ala Leu Thr Ser Val His Thr Phe Pro Ala Val Leu Gln Ser
                165                 170                 175

Ser Gly Leu Tyr Ser Leu Ser Ser Val Val Thr Val Pro Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Ala Ser Thr Tyr Arg Val Val Ser
                290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 43
<211> LENGTH: 447
<212> TYPE: PRT
<213> ORGANISM: Artificial
<220> FEATURE:
<223> OTHER INFORMATION: Synthetic construct

<400> SEQUENCE: 43

Glu Val Gln Leu Val Gln Ser Gly Ala Glu Val Lys Lys Pro Gly Ala
1               5                   10                  15

Thr Val Lys Ile Ser Cys Thr Ala Ser Gly Phe Asn Ile Glu Asp Thr
                20                  25                  30

Tyr Ile His Trp Val Gln Ala Pro Gly Gln Gly Leu Glu Trp Ile
            35                  40                  45

Gly Arg Ile Asp Pro Ala Asn Asp Asp Thr Lys Tyr Ala Pro Lys Phe
        50                  55                  60

Gln Gly Arg Ala Thr Ile Thr Ala Asp Thr Ser Thr Asp Thr Ala Tyr
65                  70                  75                  80

```
Met Glu Leu Ser Ser Leu Arg Ser Glu Asp Thr Ala Val Tyr Tyr Cys
                 85                  90                  95

Gly Arg Gly Leu Gly Arg Trp Phe Ala Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Ala Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 44
<211> LENGTH: 443
<212> TYPE: PRT
<213> ORGANISM: Artificial
<220> FEATURE:
<223> OTHER INFORMATION: Synthetic construct

<400> SEQUENCE: 44
```

```
Glu Val Gln Leu Val Gln Ser Gly Ala Glu Lys Pro Gly Ala
1               5                   10                  15

Thr Val Lys Ile Ser Cys Thr Ala Ser Gly Phe Asn Ile Glu Asp Thr
            20                  25                  30

Tyr Ile His Trp Val Gln Gln Ala Pro Gly Gln Gly Leu Glu Trp Ile
            35                  40                  45

Gly Arg Ile Asp Pro Ala Asn Asp Asp Thr Lys Tyr Ala Pro Lys Phe
        50                  55                  60

Gln Gly Arg Ala Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Gly Arg Gly Leu Gly Arg Trp Phe Ala Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
                195                 200                 205

Thr Lys Val Asp Lys Arg Val Glu Ser Lys Tyr Gly Pro Pro Cys Pro
        210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415
```

-continued

```
Gly Asn Val Phe Ser Cys Ser Val Met His Glu Ala Leu His Asn His
            420                 425                 430

Tyr Thr Gln Lys Ser Leu Ser Leu Ser Leu Gly
            435                 440

<210> SEQ ID NO 45
<211> LENGTH: 444
<212> TYPE: PRT
<213> ORGANISM: Artificial
<220> FEATURE:
<223> OTHER INFORMATION: Synthetic construct

<400> SEQUENCE: 45

Gln Val Gln Leu Val Gln Ser Gly Ala Glu Val Ala Lys Pro Gly Ala
1               5                   10                  15

Ser Val Lys Val Ser Cys Lys Ala Ser Gly Tyr Thr Phe Thr Thr Tyr
            20                  25                  30

Thr Met His Trp Val Arg Gln Arg Pro Gly Gln Gly Leu Glu Trp Ile
        35                  40                  45

Gly Asn Ile Asn Pro Asn Ser Asp Tyr Ala Ile Tyr Ala Gln Lys Phe
    50                  55                  60

Gln Gly Arg Ala Thr Met Thr Ala Asp Lys Ser Thr Asn Thr Ala Tyr
65                  70                  75                  80

Met Glu Leu Ser Ser Leu Arg Ser Glu Asp Ser Ala Val Tyr Tyr Cys
                85                  90                  95

Ala Lys Gln Ser Phe Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Ala Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335
```

-continued

```
Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 46
<211> LENGTH: 214
<212> TYPE: PRT
<213> ORGANISM: Artificial
<220> FEATURE:
<223> OTHER INFORMATION: Synthetic construct

<400> SEQUENCE: 46

Ser Ile Val Met Thr Gln Ser His Lys Phe Met Ser Thr Ser Ile Gly
1               5                   10                  15

Asp Arg Val Asn Ile Ser Cys Lys Ala Ser Gln Asp Val Ile Asn Ala
            20                  25                  30

Val Ala Trp Cys Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Leu
                85                  90                  95

Thr Phe Gly Gly Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 47
<211> LENGTH: 220
<212> TYPE: PRT
<213> ORGANISM: Artificial
<220> FEATURE:
```

<223> OTHER INFORMATION: Synthetic construct

<400> SEQUENCE: 47

```
Asp Ile Val Met Ser Gln Ser Pro Ser Ser Leu Ala Val Ser Val Gly
1               5                   10                  15

Glu Lys Ile Thr Met Ser Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Trp Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 48
<211> LENGTH: 220
<212> TYPE: PRT
<213> ORGANISM: Artificial
<220> FEATURE:
<223> OTHER INFORMATION: Synthetic construct

<400> SEQUENCE: 48

```
Asn Ile Val Met Thr Gln Thr Pro Ser Ser Leu Ala Val Ser Val Gly
1               5                   10                  15

Glu Lys Ile Thr Met Ser Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Glu Ala Glu Asp Leu Ala Val Tyr Tyr Cys Gln Gln
                85                  90                  95

Tyr Tyr Gly Tyr Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125
```

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 49
<211> LENGTH: 218
<212> TYPE: PRT
<213> ORGANISM: Artificial
<220> FEATURE:
<223> OTHER INFORMATION: Synthetic construct

<400> SEQUENCE: 49

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Phe Tyr
            20                  25                  30

Gly Thr Ser Leu Leu Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Val Asp Asp Val Ala Leu Tyr Phe Cys His Gln Gly Arg
                85                  90                  95

Lys Val Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 50
<211> LENGTH: 214
<212> TYPE: PRT
<213> ORGANISM: Artificial
<220> FEATURE:
<223> OTHER INFORMATION: Synthetic construct

<400> SEQUENCE: 50

Gly Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ile Asn Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Leu Ala Val Tyr Tyr Cys Gln Gln His Tyr Ser Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 218
<212> TYPE: PRT
<213> ORGANISM: Artificial
<220> FEATURE:
<223> OTHER INFORMATION: Synthetic construct

<400> SEQUENCE: 51

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Glu Phe Tyr
            20                  25                  30

Gly Thr Ser Leu Leu Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asp Asp Thr Ala Asn Tyr Tyr Cys His Gln Gly Arg
                85                  90                  95

Lys Val Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr

```
                130             135             140
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 52
<211> LENGTH: 7
<212> TYPE: PRT
<213> ORGANISM: Artificial
<220> FEATURE:
<223> OTHER INFORMATION: Synthetic construct

<400> SEQUENCE: 52

```
Gly Phe Thr Phe Ser Asp Ser
1               5
```

<210> SEQ ID NO 53
<211> LENGTH: 6
<212> TYPE: PRT
<213> ORGANISM: Artificial
<220> FEATURE:
<223> OTHER INFORMATION: Synthetic construct

<400> SEQUENCE: 53

```
Ser Pro Tyr Gly Gly Ser
1               5
```

<210> SEQ ID NO 54
<211> LENGTH: 9
<212> TYPE: PRT
<213> ORGANISM: Artificial
<220> FEATURE:
<223> OTHER INFORMATION: Synthetic construct

<400> SEQUENCE: 54

```
Arg His Trp Pro Gly Gly Phe Asp Tyr
1               5
```

<210> SEQ ID NO 55
<211> LENGTH: 8
<212> TYPE: PRT
<213> ORGANISM: Artificial
<220> FEATURE:
<223> OTHER INFORMATION: Synthetic construct

<400> SEQUENCE: 55

```
Gln Asp Val Ser Thr Ala Val Ala
1               5
```

<210> SEQ ID NO 56
<211> LENGTH: 7
<212> TYPE: PRT
<213> ORGANISM: Artificial
<220> FEATURE:
<223> OTHER INFORMATION: Synthetic construct

<400> SEQUENCE: 56

Ser Ala Ser Phe Leu Tyr Ser
1               5

<210> SEQ ID NO 57
<211> LENGTH: 9
<212> TYPE: PRT
<213> ORGANISM: Artificial
<220> FEATURE:
<223> OTHER INFORMATION: Synthetic construct

<400> SEQUENCE: 57

Gln Gln Tyr Leu Tyr His Pro Ala Thr
1               5

<210> SEQ ID NO 58
<211> LENGTH: 118
<212> TYPE: PRT
<213> ORGANISM: Artificial
<220> FEATURE:
<223> OTHER INFORMATION: Synthetic construct

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 59
<211> LENGTH: 107
<212> TYPE: PRT
<213> ORGANISM: Artificial
<220> FEATURE:
<223> OTHER INFORMATION: Synthetic construct

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys

<210> SEQ ID NO 60
<211> LENGTH: 448
<212> TYPE: PRT
<213> ORGANISM: Artificial
<220> FEATURE:
<223> OTHER INFORMATION: Synthetic construct

<400> SEQUENCE: 60

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
```

```
                   355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
            435                 440                 445

<210> SEQ ID NO 61
<211> LENGTH: 214
<212> TYPE: PRT
<213> ORGANISM: Artificial
<220> FEATURE:
<223> OTHER INFORMATION: Synthetic construct

<400> SEQUENCE: 61

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Ser Thr Ala
                20                  25                  30
Val Ala Trp Tyr Gln Gln Lys Pro Gly Lys Ala Pro Lys Leu Leu Ile
            35                  40                  45
Tyr Ser Ala Ser Phe Leu Tyr Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Leu Tyr His Pro Ala
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 62
<211> LENGTH: 449
<212> TYPE: PRT
<213> ORGANISM: Artificial
<220> FEATURE:
<223> OTHER INFORMATION: Synthetic construct

<400> SEQUENCE: 62
```

-continued

```
Glu Val Arg Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Thr Ser Arg Asp Asp Ser Lys Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Pro Gly Trp Tyr Ala Ala Asp Val Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
    195                 200                 205

Ser Asn Thr Lys Val Asp Lys Lys Ala Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

```
                    420                 425                 430
Ala Leu His Asn His Tyr Thr Gln Lys Ser Leu Ser Leu Ser Pro Gly
            435                 440                 445
Lys

<210> SEQ ID NO 63
<211> LENGTH: 214
<212> TYPE: PRT
<213> ORGANISM: Artificial
<220> FEATURE:
<223> OTHER INFORMATION: Synthetic construct

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Leu Pro Ala Phe
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 64
<211> LENGTH: 330
<212> TYPE: PRT
<213> ORGANISM: Artificial
<220> FEATURE:
<223> OTHER INFORMATION: Synthetic construct

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
                50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Ala Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 65
<211> LENGTH: 330
<212> TYPE: PRT
<213> ORGANISM: Artificial
<220> FEATURE:
<223> OTHER INFORMATION: Synthetic construct

<400> SEQUENCE: 65

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
```

```
            85                  90                  95
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 66
<211> LENGTH: 326
<212> TYPE: PRT
<213> ORGANISM: Artificial
<220> FEATURE:
<223> OTHER INFORMATION: Synthetic construct

<400> SEQUENCE: 66

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
```

115                 120                 125
Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 67
<211> LENGTH: 107
<212> TYPE: PRT
<213> ORGANISM: Artificial
<220> FEATURE:
<223> OTHER INFORMATION: Synthetic construct

<400> SEQUENCE: 67

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 68
<211> LENGTH: 20
<212> TYPE: PRT
<213> ORGANISM: Artificial
<220> FEATURE:
<223> OTHER INFORMATION: Synthetic construct -continued

```
<400> SEQUENCE: 68

Met Glu Thr Asp Thr Leu Leu Leu Trp Val Leu Leu Leu Trp Val Pro
1               5                   10                  15

Gly Ser Thr Gly
            20

<210> SEQ ID NO 69
<211> LENGTH: 11
<212> TYPE: PRT
<213> ORGANISM: Artificial
<220> FEATURE:
<223> OTHER INFORMATION: Synthetic construct

<400> SEQUENCE: 69

Gly Ser Ile Tyr Ser Glu Ser Tyr Tyr Trp Gly
1               5                   10

<210> SEQ ID NO 70
<211> LENGTH: 16
<212> TYPE: PRT
<213> ORGANISM: Artificial
<220> FEATURE:
<223> OTHER INFORMATION: Synthetic construct

<400> SEQUENCE: 70

Ser Ile Val Tyr Ser Gly Tyr Thr Tyr Tyr Asn Pro Ser Leu Lys Ser
1               5                   10                  15

<210> SEQ ID NO 71
<211> LENGTH: 12
<212> TYPE: PRT
<213> ORGANISM: Artificial
<220> FEATURE:
<223> OTHER INFORMATION: Synthetic construct

<400> SEQUENCE: 71

Ala Arg Val Arg Thr Trp Asp Ala Ala Phe Asp Ile
1               5                   10

<210> SEQ ID NO 72
<211> LENGTH: 11
<212> TYPE: PRT
<213> ORGANISM: Artificial
<220> FEATURE:
<223> OTHER INFORMATION: Synthetic construct

<400> SEQUENCE: 72

Gln Ala Ser Gln Asp Ile Ser Asn Tyr Leu Asn
1               5                   10

<210> SEQ ID NO 73
<211> LENGTH: 7
<212> TYPE: PRT
<213> ORGANISM: Artificial
<220> FEATURE:
<223> OTHER INFORMATION: Synthetic construct

<400> SEQUENCE: 73

Asp Ala Ser Asn Leu Glu Thr
1               5

<210> SEQ ID NO 74
<211> LENGTH: 10
<212> TYPE: PRT
<213> ORGANISM: Artificial
```

<220> FEATURE:
<223> OTHER INFORMATION: Synthetic construct

<400> SEQUENCE: 74

Gln Gln Val Leu Glu Leu Pro Pro Trp Thr
1               5                   10

<210> SEQ ID NO 75
<211> LENGTH: 120
<212> TYPE: PRT
<213> ORGANISM: Artificial
<220> FEATURE:
<223> OTHER INFORMATION: Synthetic construct

<400> SEQUENCE: 75

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Tyr Ser Glu
            20                  25                  30

Ser Tyr Tyr Trp Gly Trp Ile Arg Gln Pro Pro Gly Lys Gly Leu Glu
        35                  40                  45

Trp Ile Gly Ser Ile Val Tyr Ser Gly Tyr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Arg Thr Trp Asp Ala Ala Phe Asp Ile Trp Gly Gln
            100                 105                 110

Gly Thr Met Val Thr Val Ser Ser
        115                 120

<210> SEQ ID NO 76
<211> LENGTH: 108
<212> TYPE: PRT
<213> ORGANISM: Artificial
<220> FEATURE:
<223> OTHER INFORMATION: Synthetic construct

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Val Leu Glu Leu Pro Pro
                85                  90                  95

Trp Thr Phe Gly Gly Gly Thr Lys Val Glu Ile Lys
            100                 105

<210> SEQ ID NO 77
<211> LENGTH: 446
<212> TYPE: PRT
<213> ORGANISM: Artificial
<220> FEATURE:

<223> OTHER INFORMATION: Synthetic construct

<400> SEQUENCE: 77

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Tyr Ser Glu
            20                  25                  30

Ser Tyr Tyr Trp Gly Trp Ile Arg Gln Pro Pro Gly Lys Gly Leu Glu
        35                  40                  45

Trp Ile Gly Ser Ile Val Tyr Ser Gly Tyr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Arg Thr Trp Asp Ala Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

-continued

```
Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Leu Gly
    435                 440                 445

<210> SEQ ID NO 78
<211> LENGTH: 215
<212> TYPE: PRT
<213> ORGANISM: Artificial
<220> FEATURE:
<223> OTHER INFORMATION: Synthetic construct

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Val Leu Glu Leu Pro Pro
                85                  90                  95

Trp Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 79
<211> LENGTH: 23
<212> TYPE: DNA
<213> ORGANISM: Artificial
<220> FEATURE:
<223> OTHER INFORMATION: OVH1 primer

<400> SEQUENCE: 79
saggtccagc tgcagcagyy tgg                                            23

<210> SEQ ID NO 80
<211> LENGTH: 23
<212> TYPE: DNA
<213> ORGANISM: Artificial
<220> FEATURE:
```

<223> OTHER INFORMATION: OVH2 primer

<400> SEQUENCE: 80
caggtrcagc tgaagsagtc agg                                    23

<210> SEQ ID NO 81
<211> LENGTH: 23
<212> TYPE: DNA
<213> ORGANISM: Artificial
<220> FEATURE:
<223> OTHER INFORMATION: OVH3 primer

<400> SEQUENCE: 81
gakgtgcagc ttcagcagtc rgg                                    23

<210> SEQ ID NO 82
<211> LENGTH: 23
<212> TYPE: DNA
<213> ORGANISM: Artificial
<220> FEATURE:
<223> OTHER INFORMATION: OVH5 primer

<400> SEQUENCE: 82
gavgtgawgc tggtggagtc tgr                                    23

<210> SEQ ID NO 83
<211> LENGTH: 23
<212> TYPE: DNA
<213> ORGANISM: Artificial
<220> FEATURE:
<223> OTHER INFORMATION: OVH11 primer

<400> SEQUENCE: 83
gaagtgcagc tgttggagac tgg                                    23

<210> SEQ ID NO 84
<211> LENGTH: 23
<212> TYPE: DNA
<213> ORGANISM: Artificial
<220> FEATURE:
<223> OTHER INFORMATION: OVH14 primer

<400> SEQUENCE: 84
gaggttcagc tgcagcagtc tgk                                    23

<210> SEQ ID NO 85
<211> LENGTH: 23
<212> TYPE: DNA
<213> ORGANISM: Artificial
<220> FEATURE:
<223> OTHER INFORMATION: OVH15 primer

<400> SEQUENCE: 85
caggttcacc tacaacagtc tgg                                    23

<210> SEQ ID NO 86
<211> LENGTH: 18
<212> TYPE: DNA
<213> ORGANISM: Artificial
<220> FEATURE:
<223> OTHER INFORMATION: REVESE-6 primer

<400> SEQUENCE: 86
ctgaggarac ggtgaccg                                          18

```
<210> SEQ ID NO 87
<211> LENGTH: 22
<212> TYPE: DNA
<213> ORGANISM: Artificial
<220> FEATURE:
<223> OTHER INFORMATION: REVESE-4 primer

<400> SEQUENCE: 87
ctgaggagac tgtgagagwg gt                                            22

<210> SEQ ID NO 88
<211> LENGTH: 22
<212> TYPE: DNA
<213> ORGANISM: Artificial
<220> FEATURE:
<223> OTHER INFORMATION: REVESE-2-1 primer

<400> SEQUENCE: 88
ctgaggagac ggtgactgag gt                                            22

<210> SEQ ID NO 89
<211> LENGTH: 22
<212> TYPE: DNA
<213> ORGANISM: Artificial
<220> FEATURE:
<223> OTHER INFORMATION: REVESE-2-2 primer

<400> SEQUENCE: 89
ctgcagagac agtgaccaga gt                                            22

<210> SEQ ID NO 90
<211> LENGTH: 23
<212> TYPE: DNA
<213> ORGANISM: Artificial
<220> FEATURE:
<223> OTHER INFORMATION: OVK1 primer

<400> SEQUENCE: 90
gatgytktkv tgacccaaac tcc                                           23

<210> SEQ ID NO 91
<211> LENGTH: 23
<212> TYPE: DNA
<213> ORGANISM: Artificial
<220> FEATURE:
<223> OTHER INFORMATION: OVK3 primer

<400> SEQUENCE: 91
racattgtgc tgacmcaatc tcc                                           23

<210> SEQ ID NO 92
<211> LENGTH: 23
<212> TYPE: DNA
<213> ORGANISM: Artificial
<220> FEATURE:
<223> OTHER INFORMATION: OVK4a primer

<400> SEQUENCE: 92
saaawtgtkc tcwcccagtc tcc                                           23

<210> SEQ ID NO 93
<211> LENGTH: 23
<212> TYPE: DNA
<213> ORGANISM: Artificial
<220> FEATURE:
<223> OTHER INFORMATION: OVK4b primer
```

<400> SEQUENCE: 93
saaawtctkc tcwcccagtc tcc                                              23

<210> SEQ ID NO 94
<211> LENGTH: 23
<212> TYPE: DNA
<213> ORGANISM: Artificial
<220> FEATURE:
<223> OTHER INFORMATION: OVK4c primer

<400> SEQUENCE: 94
saaawtttkc tcwcccagtc tcc                                              23

<210> SEQ ID NO 95
<211> LENGTH: 23
<212> TYPE: DNA
<213> ORGANISM: Artificial
<220> FEATURE:
<223> OTHER INFORMATION: OVK6a primer

<400> SEQUENCE: 95
arcattgtga tgacccagwc tca                                              23

<210> SEQ ID NO 96
<211> LENGTH: 23
<212> TYPE: DNA
<213> ORGANISM: Artificial
<220> FEATURE:
<223> OTHER INFORMATION: OVK6b primer

<400> SEQUENCE: 96
arcattgtga tgacccagwc tcc                                              23

<210> SEQ ID NO 97
<211> LENGTH: 23
<212> TYPE: DNA
<213> ORGANISM: Artificial
<220> FEATURE:
<223> OTHER INFORMATION: OVK6c primer

<400> SEQUENCE: 97
grcattgtga tgacccagwc tca                                              23

<210> SEQ ID NO 98
<211> LENGTH: 23
<212> TYPE: DNA
<213> ORGANISM: Artificial
<220> FEATURE:
<223> OTHER INFORMATION: OVK6d primer

<400> SEQUENCE: 98
grcattgtga tgacccagwc tcc                                              23

<210> SEQ ID NO 99
<211> LENGTH: 23
<212> TYPE: DNA
<213> ORGANISM: Artificial
<220> FEATURE:
<223> OTHER INFORMATION: OVK10 primer

<400> SEQUENCE: 99
gatatccaga tgacacagac tac                                              23

<210> SEQ ID NO 100
<211> LENGTH: 23

<212> TYPE: DNA
<213> ORGANISM: Artificial
<220> FEATURE:
<223> OTHER INFORMATION: OVK14 primer

<400> SEQUENCE: 100
gamatcmwga tgacccartc tcc                                          23

<210> SEQ ID NO 101
<211> LENGTH: 23
<212> TYPE: DNA
<213> ORGANISM: Artificial
<220> FEATURE:
<223> OTHER INFORMATION: mIGKV1-1 primer

<400> SEQUENCE: 101
gatgytgtga tgacccaaac tcc                                          23

<210> SEQ ID NO 102
<211> LENGTH: 23
<212> TYPE: DNA
<213> ORGANISM: Artificial
<220> FEATURE:
<223> OTHER INFORMATION: mIGKV1-2 primer

<400> SEQUENCE: 102
gatgttttga tgacccaaac tcc                                          23

<210> SEQ ID NO 103
<211> LENGTH: 23
<212> TYPE: DNA
<213> ORGANISM: Artificial
<220> FEATURE:
<223> OTHER INFORMATION: mIGKV2-1 primer

<400> SEQUENCE: 103
gatattgtga tgacgcaggc tgc                                          23

<210> SEQ ID NO 104
<211> LENGTH: 23
<212> TYPE: DNA
<213> ORGANISM: Artificial
<220> FEATURE:
<223> OTHER INFORMATION: mIGKV2-2 primer

<400> SEQUENCE: 104
gatattgtga tacccagga tga                                           23

<210> SEQ ID NO 105
<211> LENGTH: 23
<212> TYPE: DNA
<213> ORGANISM: Artificial
<220> FEATURE:
<223> OTHER INFORMATION: mIGKV4-1 primer

<400> SEQUENCE: 105
gaaaatgtgc tcacycagtc tcc                                          23

<210> SEQ ID NO 106
<211> LENGTH: 23
<212> TYPE: DNA
<213> ORGANISM: Artificial
<220> FEATURE:
<223> OTHER INFORMATION: mIGKV5-1 primer

<400> SEQUENCE: 106

```
gacatcttgc tgactcagtc tcc                                             23
```

<210> SEQ ID NO 107
<211> LENGTH: 23
<212> TYPE: DNA
<213> ORGANISM: Artificial
<220> FEATURE:
<223> OTHER INFORMATION: mIGKV5-2 primer

<400> SEQUENCE: 107

```
gacattgtga tgactcagtc tcc                                             23
```

<210> SEQ ID NO 108
<211> LENGTH: 23
<212> TYPE: DNA
<213> ORGANISM: Artificial
<220> FEATURE:
<223> OTHER INFORMATION: mIGKV9-1 primer

<400> SEQUENCE: 108

```
gacatccaga tgattcagtc tcc                                             23
```

<210> SEQ ID NO 109
<211> LENGTH: 23
<212> TYPE: DNA
<213> ORGANISM: Artificial
<220> FEATURE:
<223> OTHER INFORMATION: mIGKV9-2 primer

<400> SEQUENCE: 109

```
gacatccaga tgacccagtc tcc                                             23
```

<210> SEQ ID NO 110
<211> LENGTH: 23
<212> TYPE: DNA
<213> ORGANISM: Artificial
<220> FEATURE:
<223> OTHER INFORMATION: mIGKV12-19 primer

<400> SEQUENCE: 110

```
gacatccaga tgachcagtc tcc                                             23
```

<210> SEQ ID NO 111
<211> LENGTH: 24
<212> TYPE: DNA
<213> ORGANISM: Artificial
<220> FEATURE:
<223> OTHER INFORMATION: IGKV1 primer

<400> SEQUENCE: 111

```
gatgytktga tgacccaaac tcca                                            24
```

<210> SEQ ID NO 112
<211> LENGTH: 24
<212> TYPE: DNA
<213> ORGANISM: Artificial
<220> FEATURE:
<223> OTHER INFORMATION: IGKV2-109 primer

<400> SEQUENCE: 112

```
gatattgtga tgacgcaggc tgca                                            24
```

<210> SEQ ID NO 113
<211> LENGTH: 24
<212> TYPE: DNA
<213> ORGANISM: Artificial

```
<220> FEATURE:
<223> OTHER INFORMATION: IGKV2-112 primer

<400> SEQUENCE: 113
gatattgtga tacccagga tgaa                                          24

<210> SEQ ID NO 114
<211> LENGTH: 24
<212> TYPE: DNA
<213> ORGANISM: Artificial
<220> FEATURE:
<223> OTHER INFORMATION: IGKV3-7 primer

<400> SEQUENCE: 114
gacattgtgc taacacagtc tcct                                         24

<210> SEQ ID NO 115
<211> LENGTH: 24
<212> TYPE: DNA
<213> ORGANISM: Artificial
<220> FEATURE:
<223> OTHER INFORMATION: IGKV3-1-5.10 primer

<400> SEQUENCE: 115
racattgtgc tsacccaatc tcca                                         24

<210> SEQ ID NO 116
<211> LENGTH: 24
<212> TYPE: DNA
<213> ORGANISM: Artificial
<220> FEATURE:
<223> OTHER INFORMATION: IGKV5-48 primer

<400> SEQUENCE: 116
gacatcttgc tgactcagtc tcca                                         24

<210> SEQ ID NO 117
<211> LENGTH: 24
<212> TYPE: DNA
<213> ORGANISM: Artificial
<220> FEATURE:
<223> OTHER INFORMATION: IGKV6-13 primer

<400> SEQUENCE: 117
gacattgtga tgacccagtc tcaa                                         24

<210> SEQ ID NO 118
<211> LENGTH: 24
<212> TYPE: DNA
<213> ORGANISM: Artificial
<220> FEATURE:
<223> OTHER INFORMATION: IGKV6-32 primer

<400> SEQUENCE: 118
agtattgtga tgacccagac tccc                                         24

<210> SEQ ID NO 119
<211> LENGTH: 24
<212> TYPE: DNA
<213> ORGANISM: Artificial
<220> FEATURE:
<223> OTHER INFORMATION: IGKV14 primer

<400> SEQUENCE: 119
gacatcmaga tgacmcagtc tcca                                         24
```

<210> SEQ ID NO 120
<211> LENGTH: 24
<212> TYPE: DNA
<213> ORGANISM: Artificial
<220> FEATURE:
<223> OTHER INFORMATION: IGKV4-51.86 primer

<400> SEQUENCE: 120
gaaaatgtgc tcacycagtc tcca                                         24

<210> SEQ ID NO 121
<211> LENGTH: 24
<212> TYPE: DNA
<213> ORGANISM: Artificial
<220> FEATURE:
<223> OTHER INFORMATION: IGKV7-33 primer

<400> SEQUENCE: 121
gacattgtga tgactcagtc tcca                                         24

<210> SEQ ID NO 122
<211> LENGTH: 24
<212> TYPE: DNA
<213> ORGANISM: Artificial
<220> FEATURE:
<223> OTHER INFORMATION: IGKV9-123 primer

<400> SEQUENCE: 122
gacatccaga tgattcagtc tcca                                         24

<210> SEQ ID NO 123
<211> LENGTH: 24
<212> TYPE: DNA
<213> ORGANISM: Artificial
<220> FEATURE:
<223> OTHER INFORMATION: IGKV9-124 primer

<400> SEQUENCE: 123
gacatccaga tgacccagtc tcca                                         24

<210> SEQ ID NO 124
<211> LENGTH: 24
<212> TYPE: DNA
<213> ORGANISM: Artificial
<220> FEATURE:
<223> OTHER INFORMATION: IGKV10-95 primer

<400> SEQUENCE: 124
gatatccaga tgacacagac tact                                         24

<210> SEQ ID NO 125
<211> LENGTH: 24
<212> TYPE: DNA
<213> ORGANISM: Artificial
<220> FEATURE:
<223> OTHER INFORMATION: IGKV11-125 primer

<400> SEQUENCE: 125
gatgtccaga tgattcagtc tcca                                         24

<210> SEQ ID NO 126
<211> LENGTH: 20
<212> TYPE: DNA
<213> ORGANISM: Artificial
<220> FEATURE:
<223> OTHER INFORMATION: mK-Rev primer

```
<400> SEQUENCE: 126
tacagttggt gcagcatcag                                        20
```

ANTI-PD-L1 ANTIBODY AND USES THEREOF

CROSS-REFERENCE TO RELATED APPLICATIONS

This application claims priority from international application PCT/CN2018/124314, filed on Dec. 27, 2018, which claims the benefit of Chinese patent application 201811567281.3, filed Dec. 19, 2018, and Chinese patent application 201711449321.X, filed Dec. 27, 2017. The entire contents of the foregoing are incorporated herein by reference.

The invention relates to a novel antibody and an antibody fragment thereof that specifically bind to PD-L1 and a composition comprising the antibody or the antibody fragment. In addition, the invention relates to a nucleic acid encoding the antibody or the antibody fragment thereof, a host cell comprising the nucleic acid, and related uses. Furthermore, the invention relates to therapeutic and diagnostic uses of these antibodies and antibody fragments. In particular, the invention relates to combination therapies of these antibodies and antibody fragments with other therapies, such as therapeutic modalities or agents.

BACKGROUND

Programmed death-ligand 1 (PD-L1) is a protein involved in suppressing immune system responses during chronic infections, pregnancy, tissue allografts, autoimmune diseases, and cancer. PD-L1 regulates immune responses by binding to an inhibitory receptor is called programmed death 1 (PD-1) which is expressed on the surface of T cells, B cells, and monocytes. PD-L1 also negatively regulates T cell functions through interaction with another receptor B7.1 (also known as B7-1 or CD80). The formation of PD-L1/PD-1 and PD-L1/B7.1 complexes negatively regulate T cell receptor signaling, leading to subsequent down regulation of T cell activation and inhibition of anti-tumor immune activity. PD-L1 is overexpressed in many cancers, including a variety of solid tumors, such as bladder tumors, breast tumors, colon tumors, lung tumors, melanomas, ovarian tumors, salivary tumors, stomach tumors, and thyroid tumors. PD-L1 overexpression in tumor cells could promote tumor invasion and is often associated with poor prognosis.

Therefore, there is still a need in the art for new anti-PD-L1 antibodies that bind better to PD-L1 and have good druggability.

SUMMARY

Disclosed herein is an antibody molecule binding to PD-LL. A nucleic acid encoding the antibody or the antibody fragment thereof, and an expression vector, a host cell, and a method for producing the antibody molecule are also provided. Also provided are an immunoconjugate comprising an anti-PD-L1 antibody molecule, a multispecific or bispecific antibody molecule, and a pharmaceutical composition. The anti-PD-L1 antibody molecule disclosed herein can be used alone or in combination with other therapies, such as therapeutic agents or modalities, to treat, prevent and/or diagnose tumor diseases and infectious diseases. In addition, disclosed herein are a composition and a method for detecting PD-L1, and a method for preventing or treating a variety of diseases including tumors and/or infectious diseases using the anti-PD-L1 antibody molecule.

Therefore, in some embodiments, the antibody or the fragment thereof of the invention (specifically) binds to PD-L1. In some embodiments, the antibody or the fragment thereof of the invention (specifically) binds to human PD-L1.

In some embodiments, the anti-PD-L1 antibody or the fragment thereof of the invention binds to PD-L1 (e.g., human PD-L1) with high affinity, for example, binds to PD-L1 with an equilibrium dissociation constants ($K_D$) of less than about 50 nM, preferably less than or equal to about 20 nM, more preferably less than or equal to about 15 nM, more preferably less than or equal to about 10 nM, 9 nM, 8 nM, 7 nM, 6 nM, 5 nM, 4 nM, 3 nM, or 2 nM, and most preferably, less than or equal to about 1.5 nM, 1.4 nM, 1.3 nM, 1.2 nM, 1.1 nM, 1 nM, 0.9 nM, or 0.8 nM. In some embodiments, the anti-PD-L1 antibody of the invention binds to PD-L1 with a $K_D$ of 0.1-10 nM, preferably 0.5-10 nM, more preferably 0.6-10 nM, 0.7-8 nM, and 0.7-5 nM, and most preferably 0.5-1.5 nM, 0.7-1.5 nM, and 0.7-1 nM. In some embodiments, the PD-L1 is a human PD-L1. In some embodiments, the antibody binding affinity is determined using biological optical interferometry (e.g., Fortebio affinity measurement).

In some embodiments, the antibody or the fragment thereof of the invention binds to cells expressing human PD-L1, for example, with an $EC_{50}$ of less than or equal to about 4 nM, 3.5 nM, 3 nM, 2.9 nM, 2.8 nM, 2.7 nM, 2.6 nM, 2.5 nM, 2.4 nM, 2.3 nM, 2.2 nM, 2.1 nM, 2 nM, 1.9 nM, 1.8 nM, 1.7 nM, or 1.6 nM. In some embodiments, the binding is determined using flow cytometry (e.g., FACS). In some embodiments, the cell expressing human PD-L1 is a CHO cell expressing human PD-L1.

In some embodiments, the antibody or the fragment thereof of the invention blocks relevant activities of PD-L1, for example, with an $EC_{50}$ of less than or equal to about 10 nM, 5 nM, 4 nM, 3 nM, 2 nM, 1 nM, 0.9 nM, 0.8 nM, or 0.7 nM, and preferably 0.1-1 nM, 0.5-1 nM, 0.6-1 nM, 0.6 nM, 0.7 nM, 0.8 nM, 0.9 nM, or 1 nM. In some embodiments, the relevant activity of PD-L1 is the binding of PD-L1 to PD-1. In some embodiments, the antibody or the fragment thereof of the invention inhibits the binding of PD-L1 to PD-1 with an $EC_{50}$ of less than or equal to about 10 nM, 5 nM, 4 nM, 3 nM, 2 nM, 1 nM, 0.9 nM, 0.8 nM, or 0.7 nM, and preferably 0.1-1 nM, 0.5-1 nM, 0.6-1 nM, 0.6 nM, 0.7 nM, 0.8 nM, 0.9 nM, or 1 nM in an MOA assay. In some embodiments, the cell is a CHO cell.

In some embodiments, the antibody or the fragment thereof of the invention increases T cell functions. In some embodiments, the antibody or the fragment thereof of the invention increases T cell proliferation. In some embodiments, the antibody or the fragment thereof of the invention increases IFN-γ secretion. In some embodiments, the antibody or the fragment thereof of the invention increases IL-2 secretion. In some embodiments, the antibody or the fragment thereof of the invention increases both IFN-γ secretion and IL-2 secretion. In some embodiments, the increase is determined in a mixed lymphocyte reaction (MLR). In some embodiments, the ability of the antibody or the fragment thereof of the invention to activate T cells is superior to known anti-PD-L1 antibodies, such as Tecentriq.

In some embodiments, the antibody or the fragment thereof of the invention is less viscous than known anti-PD-L1 antibody (e.g., Tecentriq), and therefore has better druggability. In some embodiments, the antibody or the fragment thereof of the invention has a retention time (RT) of less than about 10 minutes, about 9 minutes, or about 8 minutes, preferably, about 7-9 minutes, and preferably about 7-8.5 minutes, about 7.5-8.5 minutes, about 7-8 minutes, or about 7.5-8 minutes, such as about 7.5 minutes, 7.6 minutes, 7.7 minutes, 7.8 minutes, 7.9 minutes, 8 minutes, 8.1 minutes, 8.2 minutes, 8.3 minutes, 8.4 minutes, 8.5 minutes, in a Zenix column chromatography.

In some embodiments, the antibody or the fragment thereof of the invention inhibits one or more activities of PD-L1, for example, causing one or more of the following: increased tumor-infiltrating lymphocytes, increased T cell receptor-mediated proliferation, or decreased immune evasion of cancer cells.

In some embodiments, the anti-PD-L1 antibody or the fragment thereof of the invention can induce antibody-dependent cell-mediated cytotoxicity (ADCC).

In some embodiments, the anti-PD-L1 antibody of the invention, alone or in combination with other therapies (e.g., therapeutic modalities and/or agents), is effective in treating tumors (e.g., cancer) or infections (e.g., chronic infection). In some embodiments, the tumor is a tumor immune escape. In some embodiments, the tumor is cancer. In some embodiments, the tumor is a gastrointestinal tumor. In some embodiments, the cancer is colon cancer.

In some embodiments, the heavy chain and/or light chain of the anti-PD-L1 antibody or the fragment thereof of the invention further comprises a signal peptide sequence, such as METDTLLLWVLLLVWVPGSTG (SEQ ID NO: 68).

In some embodiments, the antibody of the invention also encompasses variants of the amino acid sequence of the anti-PD-L1 antibody, as well as antibodies that bind to the same epitope as any of the anti-PD-L1 antibodies or the fragments thereof described above.

In some embodiments, the anti-PD-L1 antibody of the invention further comprises a human or murine constant region. In some embodiments, the anti-PD-L1 antibody of the invention is an antibody in the form of IgG1, IgG2, IgG3, IgG4, IgM, IgA1, IgA2, IgD, or IgE. In some embodiments, the anti-PD-L1 antibody of the invention comprises a heavy chain constant region selected from the group consisting of heavy chain constant regions of, for example, IgG1, IgG2, IgG3, IgG4, IgM, IgA1, IgA2, IgD, and IgE; particularly, selected from the group consisting of heavy chain constant regions of, for example, IgG1, IgG2, IgG3, and IgG4, and more particularly, a heavy chain constant region of IgG1 or IgG4, such as a heavy chain constant region of human IgG1 or IgG4. In one embodiment, the heavy chain constant region is a heavy chain constant region of human IgG1 or human IgG4. In some embodiments, the murine constant region comprised in the anti-PD-L1 antibody of the invention is selected from the group consisting of IgG1, IgG2A, IgG2B, and IgG3.

In another embodiment, the anti-PD-L1 antibody molecule of the invention has a light chain constant region selected from, e.g., a kappa or lambda light chain constant region, and preferably a kappa (e.g., human kappa) light chain constant region.

In another embodiment, the anti-PD-L1 antibody molecule comprises a heavy chain constant region of IgG4 (e.g., human IgG4). In one embodiment, the human IgG4 comprises a substitution at position 228 according to EU numbering (e.g., a substitution of Ser to Pro). In another embodiment, the human IgG4 contains a mutation to AA at positions 114-115 (EU numbering) (Armour KL1, Clark M R, Hadley A G, Williamson L M, Eur J Immunol., August, 1999; 29(8):2613-24, Recombinant human IgG molecules lacking Fcgamma receptor I binding and monocyte triggering activities). In another embodiment, the anti-PD-L1 antibody molecule comprises a heavy chain constant region of IgG1 (e.g., human IgG1). In one embodiment, the human IgG1 comprises a substitution at position 297 according to EU numbering (e.g., a substitution of Asn to Ala). In one embodiment, the human IgG1 comprises a substitution at position 265 according to EU numbering, a substitution at position 329 according to EU numbering, or both (e.g., a substitution of Asp to Ala at position 265 according to EU numbering and/or a substitution of Pro to Ala at position 329 according to EU numbering). In one embodiment, the human IgG1 comprises a substitution at position 234 according to EU numbering, a substitution at position 235 according to EU numbering, or both (e.g., a substitution of Leu to Ala at position 234 according to EU numbering and/or a substitution of Leu to Ala at position 235 according to EU numbering). In one embodiment, the heavy chain constant region comprises an amino acid sequence as shown in SEQ ID NOs: 64, 65, or 66, or a sequence having at least 80%, 85%, 90%, 91%, 92%, 93%, 94%, 95%, 96%, 97%, 98%, 99% or more identity to the same, or consists of the sequence.

In another embodiment, the anti-PD-L1 antibody molecule comprises a kappa light chain constant region, e.g., a human kappa light chain constant region. In one embodiment, the light chain constant region comprises an amino acid sequence as shown in SEQ ID NO: 67, or a sequence having at least 80%, 85%, 90%, 91%, 92%, 93%, 94%, 95%, 96%, 97%, 98%, 99%, or more identity to the same, or consists of the sequence.

In one embodiment, the anti-PD-L1 antibody molecule comprises a heavy chain constant region of IgG1 (e.g., a heavy chain constant region of human IgG1) and a kappa light chain constant region (e.g., a human kappa light chain constant region). In one embodiment, the human IgG1 comprises a substitution at position 297 according to EU numbering (e.g., a substitution of Asn to Ala). In some embodiment, the IgG1 heavy chain constant region comprises an amino acid sequence as shown in SEQ ID NOs: 64 or 65, or a sequence having at least 80%, 85%, 90%, 91%, 92%, 93%, 94%, 95%, 96%, 97%, 98%, 99% or more identity to the same, or consists of the sequence. In one embodiment, the human kappa light chain constant region comprises an amino acid sequence as shown in SEQ ID NO: 67, or a sequence having at least 80%, 85%, 90%, 91%, 92%, 93%, 94%, 95%, 9%%, 97%, 98%, 99% or more identity to the same, or consists of the sequence.

In another embodiment, the anti-PD-L1 antibody molecule comprises a heavy chain constant region of IgG4 (e.g., a human IgG4 heavy chain constant region) and a kappa light chain constant region (e.g., a human kappa light chain constant region). In one embodiment, the constant region is a mutated IgG4 constant region, e.g., a mutated human IgG4 constant region (e.g., having a mutation at position 228 according to EU numbering, such as S228P mutation, and/or having a mutation to AA at positions 114-115 (EU numbering)). In some embodiment, the IgG4 heavy chain constant region comprises an amino acid sequence as shown in SEQ ID NO: 66, or a sequence having at least 80%, 85%, 90%, 91%, 92%, 93%, 94%, 95%, 96%, 97%, 98%, 99% or more identity to the same, or consists of the sequence. In one embodiment, the human kappa light chain constant region comprises an amino acid sequence as shown in SEQ ID NO: 67, or a sequence having at least 80%, 85%, 90%, 91%, 92%, 93%, 94%, 95%, 96%, 97%, 98%, 99% or more identity to the same, or consists of the sequence.

In one embodiment, the anti-PD-L1 antibody molecule is isolated or recombinant.

In some embodiments, the anti-PD-L1 antibody is a monoclonal antibody or an antibody of monospecificity. The anti-PD-L1 antibody molecule may also be a humanized, chimeric, or human antibody molecule. In some embodiments, the anti-PD-L1 antibody is a chimeric antibody. In some embodiments, the anti-PD-L1 antibody is a humanized antibody. In some embodiments, the anti-PD-L1 antibody is a human antibody. In some embodiments, at least a portion of the framework sequence of the anti-PD-L1 antibody is a human consensus framework sequence. In one embodiment, the anti-PD-L1 antibody of the invention also comprises an antibody fragment thereof, preferably an antibody fragment selected from the group consisting of: Fab, Fab', Fab'-SH, Fv, single-chain variable fragment (e.g., scFv) or (Fab')$_2$, single-domain antibody, diabody (dAb), or linear antibody.

In some embodiments, the anti-PD-L1 antibody molecule is in the form of a bispecific or multispecific antibody molecule. In one embodiment, the bispecific antibody molecule has a first binding specificity for PD-L1 and a second binding specificity for LAG-3. In one embodiment, the bispecific antibody molecule binds to PD-L1 and LAG-3. Multispecific antibody molecule may have any combinations of binding specificities for PD-L1 and other targets.

In one aspect, the invention provides a nucleic acid encoding any of the above anti-PD-L1 antibodies or fragments thereof. In one embodiment, a vector comprising the nucleic acid is provided. In one embodiment, the vector is an expression vector. In one embodiment, a host cell comprising the nucleic acid or the vector is provided. In one embodiment, the host cell is eukaryotic. In another embodiment, the host cell is selected from yeast cells, mammalian cells (e.g., CHO cells or 293 cells), or other cells suitable for preparation of an antibody or antigen-binding fragment thereof. In another embodiment, the host cell is prokaryotic, such as an *E. coli* cell.

In one embodiment, the invention provides a method for preparing the anti-PD-L1 antibody or fragment thereof (preferably antigen-binding fragment), wherein the method comprises incubating the host cell under conditions suitable for the expression of nucleic acid encoding the antibody or fragment thereof (preferably antigen-binding fragment), and optionally isolating the antibody or fragment thereof (preferably antigen-binding fragment). In a certain embodiment, the method further comprises recovering the anti-PD-L1 antibody or fragment thereof (preferably antigen-binding fragment) from the host cell.

In some embodiments, the invention provides an immunoconjugate comprising any of the anti-PD-L1 antibodies provided herein and other substances, such as a cytotoxic agent or a marker. In some embodiments, the immunoconjugate is used to prevent or treat tumors (e.g., cancer) or infectious diseases. In some embodiments, the tumor is a tumor immune escape. Preferably, the tumor is a gastrointestinal tumor (e.g., cancer), such as colon cancer. Preferably, the infectious disease is a chronic infection.

In some embodiments, the invention provides a composition comprising any of the anti-PD-L1 antibodies or the fragments thereof (preferably the antigen-binding fragments), or the immunoconjugates thereof described herein, wherein, preferably, the composition is a pharmaceutical composition. In one embodiment, the composition further comprises pharmaceutical supplementary materials. In one embodiment, the composition, e.g., the pharmaceutical composition, comprises the anti-PD-L1 antibody or fragment thereof of the invention or the immunoconjugate thereof, and a combination of one or more other therapeutic agents (e.g., chemotherapeutic agents, other antibodies, cytotoxic agents, vaccines, active anti-infective agents, or immunomodulators such as activators of co-stimulatory molecules or inhibitors of immune checkpoint molecules).

In some embodiments, the pharmaceutical composition is used to prevent or treat tumors (e.g., cancer) or infections. In some embodiments, the tumor is a tumor immune escape. Preferably, the tumor is a gastrointestinal tumor (e.g., cancer), such as colon cancer. Preferably, the infectious disease is a chronic infection. In another aspect, the invention relates to a method for preventing or treating a tumor (e.g., cancer) or an infectious disease in a subject or an individual, wherein the method comprises administering to the subject an effective amount of any anti-PD-L1 antibodies or fragments thereof, pharmaceutical compositions, or immunoconjugates described herein. In some embodiments, the tumor is a tumor immune escape. In one embodiment, the tumor is a gastrointestinal tumor (e.g., cancer), such as colon cancer. In one embodiment, the infectious disease is a chronic infection. In another aspect, the invention also relates to use of any of the anti-PD-L1 antibodies or fragments thereof described herein for preparing a medicament for treating tumors (e.g., cancer) or infections in a subject. In some embodiments, the tumor is a tumor immune escape. In one embodiment, the tumor is a gastrointestinal tumor (e.g., cancer), such as colon cancer. In one embodiment, the infectious disease is a chronic infection.

In some further embodiments, the method of prevention or treatment described herein further comprises administering one or more therapies (e.g., therapeutic modalities and/or other therapeutic agents) to the subject or individual. In some embodiments, the therapeutic modality includes surgical treatments and/or radiation therapies. In some embodiments, other therapeutic agents are selected from the group consisting of chemotherapeutic agents, cytotoxic agents, vaccines, anti-infective active agents, other antibodies, and immunomodulators (e.g., co-stimulatory molecule activators or immune checkpoint molecule inhibitors).

In some embodiments, the subject or individual is a non-human animal, such as a mammal, preferably a human.

In one aspect, the invention relates to a method for detecting PD-L1 in a sample, comprising (a) contacting the sample with any of the anti-PD-L1 antibodies or fragments thereof described herein; and (b) detecting the formation of the complex of the anti-PD-L1 antibodies or fragments thereof and PD-L1. In one embodiment, the anti-PD-L1 antibody is detectably labeled.

In some embodiments, the invention relates to a kit or artifact comprising the anti-PD-L1 antibody or fragment thereof described herein. In some embodiments, the kit or artifact comprises the anti-PD-L1 antibody or fragment thereof described herein and optional pharmaceutical supplementary materials. In some embodiments, the kit or artifact further comprises instructions for administering the drug to treat a tumor or infection.

The invention also encompasses any combination of any of the embodiments described herein. Any of the embodiments described herein or any combination thereof are/is applicable to any and all of the anti-PD-L1 antibodies or fragments thereof, the methods, and the uses of the invention described herein.

STATEMENT REGARDING SEQUENCE LISTING

The Sequence Listing associated with this application is provided in text form in lieu of a paper copy, and is hereby incorporated by reference into the specification. The name of the text file containing the Sequence Listing is Sequence Listing.txt. The text file is 94.2 KB, and was created and submitted electronically via EFS-Web on Jun. 30, 2020.

DETAILED DESCRIPTION

Abbreviations

Figure 1:
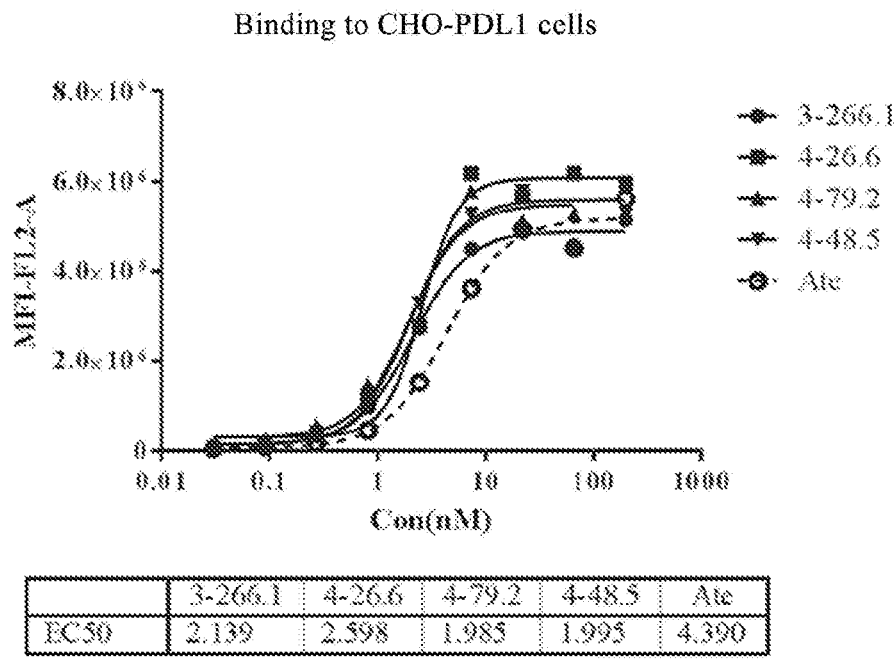
FIG. 1 shows the binding of the anti-PD-L1 antibody of the invention to CHO-PDL1 cells determined by FACS.

Unless otherwise stated, the abbreviations in this specification have the following meanings: The following abbreviations are used:
ADCC Antibody-dependent cell-mediated cytotoxicity
CDC Complement dependent cytotoxicity
CDR Complementarity determining region in variable region of immunoglobulin
CHO Chinese hamster ovary
$EC_{50}$ A concentration resulting in 50% potency or binding
$K_D$ Equilibrium dissociation constant
ELISA Enzyme-linked immunosorbent assay
FACS Fluorescence-activated cell sorting
MOA Mechanism of action
MLR Mixed lymphocyte reaction
FR Antibody framework region
$IC_{50}$ A concentration producing 50% inhibition
Ig Immunoglobulin
Kabat Immunoglobulin alignment and numbering system established by Elvin A Kabat ((1991) Sequences of Proteins of Immunological Interest, 5th Edition Public Health Service, National Institutes of Health, Bethesda, Md.)
mAb/Mab/MAb Monoclonal antibody
PCR Polymerase chain reaction
IFN Interferon
VL Light chain variable region
VH Heavy chain variable region
LC Light chain
HC Heavy chain
HCDR Heavy chain complementary determining region
LCDR Light chain complementary determining region

Definition

Before the invention is described in detail below, it should be understood that the invention is not limited to the particular methodology, protocols, and reagents described herein, as these may vary. It should also be understood that the terminology used herein is for the purpose of describing particular embodiments only, and is not intended to limit the scope of the invention, which will be limited only by the appended claims. Unless defined otherwise, all technical and scientific terms used herein have the same meaning as commonly understood by those of ordinary skill in the art to which the invention belongs.

For the purpose of explaining this specification, the following definitions will be used, and wherever appropriate, terms used in the singular may also include the plural and vice versa. It is understood that the terminology used herein is for the purpose of describing particular embodiments only and is not intended to be limiting.

The term "about" used in combination with a numerical value is intended to encompass the numerical values in a range from a lower limit less than the specified numerical value by 5% to an upper limit greater than the specified numerical value by 5%.

"Affinity" refers to the strength of the sum total of all non-covalent interactions between a single binding site of a molecule (e.g., an antibody) and its binding partner (e.g., an antigen). Unless stated otherwise, when used herein, "binding affinity" refers to intrinsic binding affinity that reflects a 1:1 interaction between members of a binding pair (e.g., antibody and an antigen). The affinity of a molecule X for its partner Y can generally be represented by the equilibrium dissociation constant ($K_D$). Affinity can be measured by common methods known in the art, including those known in the prior art and described herein.

The terms "programmed cell death 1 ligand 1", "PD-L1", "programmed death ligand 1", "cluster of differentiation 274", "CD274", or "B7 homolog 1" as used herein refer to any natural PD-L1 from any vertebrate source including mammals such as primates (e.g., humans) and rodents (e.g., mice and rats). The terms encompass "full length", unprocessed PD-L1, and PD-L1 of any form that results from processing in the cell. PD-L1 may present as a transmembrane protein or as a soluble protein. The terms also encompass variants of naturally occurring PD-L1, such as splicing variants or allelic variants. The basic structure of PD-L1 includes four domains: an extracellular Ig-like V-type domain and an Ig-like C2-type domain, a transmembrane domain and a cytoplasmic domain. Additional information about the human PD-L1 gene including genomic DNA sequences can be found under NCBI Gene ID No. 29126. Additional information about the human PD-L1 gene including genomic DNA sequences can be found under NCBI Gene ID No. 60533. The amino acid sequence of an exemplary full-length human PD-L1 protein can be found, e.g., under NCBI accession number NP_001254653 or UniProt accession number Q9NZQ7, and the sequence of an exemplary full-length mouse PD-L1 protein can be found, e.g., under NCBI accession number NP_068693 or Uniprot accession number Q9EP73.

The terms "anti-PD-L1 antibody", "anti-PD-L1", "PD-L1 antibody" or "PD-L1-binding antibody" as used herein refer to antibodies capable of binding PD-L1 protein with sufficient affinity, or fragments thereof. In one embodiment, the extent to which the anti-PD-L1 antibody binds to a non-PD-L1 protein is less than about 10%, about 20%, about 30%, about 40%, about 50%, about 60%, about 70%, about 80%, or about 90% or more of the extent to which the antibody binds to a PD-L1 protein, as measured. e.g., by radioimmunoassay (RIA) or bio-optical interference assay or MSD assay.

As used herein, "monoclonal antibody" or "mAb" or "Mab" refers to an antibody of a single copy or clone derived from, e.g., a eukaryotic, prokaryotic, or phage clone, and not the method by which they are produced. Monoclonal antibodies or antigen-binding fragments thereof can be produced, e.g., by hybridoma technology, recombinant technology, phage display technology, synthetic technology such as CDR grafting, or a combination of such or other techniques known in the art.

"Native antibody" refers to naturally occurring immunoglobulin molecules of different structures. For example, a native IgG antibody is a heterotetrameric glycoprotein of about 150,000 Daltons, consisting of two identical light chains and two identical heavy chains bonded with a disulfide bond. From N- to C-terminuses, each heavy chain has a variable region (VH), also referred to as a variable heavy domain or a heavy chain variable domain, followed by three constant domains (CH1, CH2, and CH3). Similarly, from N- to C-terminuses, each light chain has a variable region (VL), also referred to as a variable light domain or a light chain variable domain, followed by a constant light (CL) domain. The light chain of antibody can be assigned to one of two types, called kappa (κ) and lambda (λ), based on the amino acid sequence of its constant domain. "Fc region of native sequence" includes amino acid sequence identical to the amino acid sequence of Fc regions found in nature. Human Fc region of native sequence includes: human IgG1 Fc region of native sequence (non-A and A allotypes), human IgG2 Fc region of native sequence, human IgG3 Fc region of native sequence, and human IgG4 Fc region of native sequence, and naturally occurring variants of the foregoing.

"Antibody fragment" refers to a molecule different from an intact antibody, which comprises a portion of the intact antibody and binding to an antigen to which the intact antibody binds. Examples of antibody fragments include but are not limited to Fv, Fab, Fab', Fab'-SH, F(ab')$_2$; diabodies; linear antibodies; single chain antibodies (e.g., scFv); single domain antibodies; bivalent or bispecific antibodies or fragments thereof; camelid antibodies; and bispecific antibodies or multispecific antibodies formed from the antibody fragments.

As used herein, the term "epitope" refers to moieties of an antigen (e.g., human PD-L1) that specifically interact with an antibody molecule. Such moieties (referred to herein as an antigenic determinant) generally comprise, or are part of, elements such as amino acid side chains or sugar side chains. Antigenic determinant can be defined using methods known in the art or disclosed herein (e.g., by crystallography or by hydrogen-deuterium exchange). At least one or some moieties of the antibody molecule that specifically interact with the antigenic determinant are generally located within the CDRs. Generally, an epitope has specific three-dimensional structural characteristics. Generally, an epitope has specific charge characteristics. Some epitopes are linear epitopes, while others are conformational epitopes.

"Antibody that binds to the same or overlapping epitope" as a reference antibody refers to an antibody that blocks 50%, 60%, 70%, 80%, 90%, or 95% or more of the binding of the reference antibody to its antigen in a competition assay, or conversely, the reference antibody blocking 50%, 60%, 70%, 80%, 90%, or 95% or more of the binding of the antibody to its antigen in a competition assay.

An antibody that competes with a reference antibody to bind to its antigen refers to an antibody that blocks 50%, 60%, 70%, 80%, 90%, or 95% or more of the binding of the reference antibody to its antigen in a competition assay. Conversely, the reference antibody blocks 50%, 60%, 70%, 80%, 90%, or 95% or more of the binding of the antibody to its antigen in a competition assay. Numerous types of competitive binding assays can be used to determine whether an antibody competes with another, such as direct or indirect solid-phase radioimmunoassay (RIA), direct or indirect solid-phase enzyme immunoassay (EIA), sandwich competition assay (see, e.g., Stahli et al., 1983. Methods in Enzymology 9:242-253).

An antibody that inhibits (e.g., competitively inhibits) the binding of a reference antibody to its antigen refers to an antibody that inhibits 50%, 60%, 70%, 80%, 90%, or 95% or more of the binding of the reference antibody to its antigen. Conversely, the reference antibody inhibits 50%, 60%, 70%, 80%, 90%, or 95% or more of the binding of the antibody to its antigen. The binding of an antibody to its antigen can be measured by affinity (e.g., equilibrium dissociation constant). Methods for determining affinity are known in the art.

An antibody that shows the same or similar binding affinity and/or specificity as a reference antibody refers to an antibody that is capable of having at least 50%, 60%, 70%, 80%, 90%, or 95% or more of the binding affinity and/or specificity of the reference antibody. This can be determined by any methods known in the art for determining binding affinity and/or specificity.

"Complementarity determining region" or "CDR region" or "CDR" is a region in an antibody variable domain that is highly variable in sequence and forms a structurally defined loop ("hypervariable loop") and/or comprises antigen-contacting residues ("antigen contact point"). CDRs are primarily responsible for binding to epitopes. The CDRs of the heavy and light chains are generally referred to as CDR1, CDR2, and CDR3, and are numbered sequentially from the N-terminus. The CDRs located in the variable domain of the antibody heavy chains are referred to as HCDR1, HCDR2, and HCDR3, while the CDRs located in the variable domain of the antibody light chains are referred to as LCDR1, LCDR2, and LCDR3. In a given amino acid sequence of a light chain variable region or a heavy chain variable region, the exact amino acid sequence boundary of each CDR can be determined using any one or a combination of many well-known antibody CDR assignment systems including, e.g., Chothia based on the three-dimensional structure of antibodies and the topology of the CDR loops (Chothia et al. (1989) Nature 342:877-883; Al-Lazikani et al., "Standard conformations for the canonical structures of immunoglobulins", Journal of Molecular Biology, 273:927-948 (1997)), Kabat based on antibody sequence variability (Kabat et al., Sequences of Proteins of Immunological Interest, 4th edition, US Department of Health and Human Services, National Institutes of Health (1987)), AbM (University of Bath), Contact (University College London), International ImMunoGeneTics database (IMGT) (imgt.cines.fr/ on the World Wide Web), and North CDR definition based on the affinity propagation clustering using a large number of crystal structures.

For example, according to different CDR determination schemes, the residues of each CDR are as follows.

| CDR | Kabat scheme | AbM scheme | Chothia scheme | Contact scheme |
|---|---|---|---|---|
| LCDR1 | L24-L34 | L24-L34 | L26-L32 | L30-L36 |
| LCDR2 | L50-L56 | L50-L56 | L50-L52 | L46-L55 |
| LCDR3 | L89-L97 | L89-L97 | L91-L96 | L89-L96 |
| HCDR1 | H31-H35B | H26-H35B | H26-H32 | H30-H35B |
| | (Kabat numbering system) | | | |
| HCDR1 | H31-H35 | H26-H35 | H26-H32 | H30-H35 |
| | (Chothia Numbering System) | | | |
| HCDR2 | H50-H65 | H50-H58 | H53-H55 | H47-H58 |
| HCDR3 | H95-H102 | H95-H102 | H96-H101 | H93-H101 |
| | (Kabat numbering system) | | | |

CDRs can also be determined based on having the same Kabat numbering positions as a reference CDR sequence (e.g., any of the exemplary CDRs of the invention).

Unless otherwise stated, in the invention, the term "CDR" or "CDR sequence" encompasses CDR sequences determined by any of the manners described above.

Unless otherwise stated, in the invention, when referring to the position of residues in an antibody variable region (including heavy chain variable region residues and light chain variable region residues), it refers to the numbering positions according to the Kabat numbering system (Kabat et al., Sequences of Proteins of Immunological Interest, 5th Ed. Public Health Service, National Institutes of Health, Bethesda, Md. (1991)).

In one embodiment, the boundaries of the CDRs of the antibodies of the invention are determined by Chothia rules or Kabat rules, e.g., antibodies of sequences shown in Table 1.

It should be noted that boundaries of CDRs of variable regions of an antibody obtained by different assignment systems may differ. That is, CDR sequences of variable regions of an antibody defined by different assignment systems differ. Therefore, when it comes to defining an antibody with specific CDR sequences defined in the invention, the scope of the antibody also encompasses such antibody whose variable region sequences comprise the specific CDR sequences, but having claimed CDR boundaries different from the specific CDR boundaries defined by the invention as a different protocol (e.g., different assignment system rules or their combinations) is applied.

Antibodies with different specificities (i.e., different binding sites for different antigens) have different CDRs (under the same assignment system). However, although CDRs differ from antibody to antibody, only a limited number of amino acid positions within the CDRs are directly involved in antigen binding. The smallest overlapping region can be determined using at least two of the Kabat, Chothia, AbM, Contact, and North methods, thereby providing a "minimal binding unit" for antigen binding. The minimal binding unit may be a sub-portion of the CDR. As will be clear to those skilled in the art, residues of the rest CDR sequences can be determined by antibody structure and protein folding. Therefore, any variants of the CDRs given herein will also be considered in the invention. For example, in one CDR variant, the amino acid residues in the minimal binding unit may remain unchanged, while the other CDR residues defined by Kabat or Chothia may be substituted by conservative amino acid residues.

Five major classes of antibodies are known in the art: IgA, IgD, IgE, IgG, and IgM, and several of these classes can be further divided into subclasses (isotypes), e.g., IgG1, IgG2, IgG3, IgG4, IgA1, and IgA2. The heavy chain constant domains that correspond to different classes of immunoglobulins are referred to as α, δ, ε, γ, and μ, respectively.

"Antibody in IgG form" refers to the IgG form to which the heavy chain constant region of an antibody belongs. Heavy chain constant regions of all antibodies of the same type are identical, and heavy chain constant regions of antibodies of different types are different. For example, an antibody in the form of IgG1 refers to the Ig domain of its heavy chain constant region being an Ig domain of an IgG1.

"Antibody-dependent cell-mediated cytotoxicity" or "ADCC" refers to a form of cytotoxicity in which a secreted immunoglobulin binding to a Fc receptor (FcR) present on certain cytotoxic cells (e.g., NK cells, neutrophils and macrophages) enables such cytotoxic effector cells to bind specifically to antigen-bearing target cells and subsequently kill the target cells with cytotoxin. The primary cells mediating ADCC, NK cells, express FcγRIII only, whereas monocytes express FcγRI, FcγRII, and FcγRIII. Table 3 on page 464 of Ravetch and Kinet, Annu. Rev. Immunol. 9:457-92 (1991) summarizes the FcR expression on hematopoietic cells. To evaluate the ADCC activity of the molecule of interest, an in vitro ADCC assay can be performed, such as described in U.S. Pat. No. 5,500,362 or 5,821,337, or U.S. Pat. No. 6,737,056 (Presta). Effector cells useful for such assays include PBMC and NK cells. Optionally/alternatively, the ADCC activity of the molecule of interest can be assessed in vivo, e.g., in an animal model, such as that disclosed in Clynes et al., PNAS (USA) 95:652-656 (1998).

The term "cytotoxic agent" or "cytotoxic factor" used in the invention refers to substances that inhibit or prevent cell function and/or causes cell death or destruction. Examples of cytotoxic agents are those disclosed in WO2015/153513, WO2016/028672. WO2015/138920, and WO2016/007235.

The term "therapeutic agent" as described herein encompasses any substance effective in preventing or treating tumors (such as cancer) and infections (such as chronic infections), including chemotherapeutic agents, cytotoxic agents, vaccines, other antibodies, active anti-infective agents, immunomodulators, such as any of the substances disclosed in WO2016/007235 or WO2010/077634 or U.S. 60/696,426 that can be used in combination with anti-PD-L1 antibodies.

"Chemotherapeutic agents" include chemical compounds useful in treatment of cancer. Examples of chemotherapeutic agents are those disclosed in WO2016/007235, WO2010/077634, U.S. 60/696,426 or WO2016/061142, U.S. 61/264,061, or WO2016/007235.

The term "cytokine" is a general term for proteins that are released by a cell population and act as intercellular mediators on another cell. Examples of such cytokines are lymphokines and monokines; interleukins (IL), such as IL-1, IL-1α, IL-2, IL-3, IL-4, IL-5, IL-6, IL-7, IL-8, IL-9, IL-11, IL-12, and IL-15; tumor necrosis factor, such as TNF-α or TNF-β; and other polypeptide factors, including LIF and kit ligand (KL) and γ-interferon. As used herein, the term cytokine includes proteins from natural sources or from recombinant cell cultures and biologically active equivalents of cytokines of native sequence, including small molecule entities produced by artificial synthesis, and pharmacologically acceptable derivatives and salts thereof.

The term "co-stimulatory molecule" refers to a relevant binding partner that specifically binds to a co-stimulatory ligand on a T cell and thus allows a T-cell-mediated co-stimulatory response (for example, but not limited to, proliferation). Co-stimulatory molecules are cell surface molecules other than antigen receptors or ligands thereof required for a highly efficient immune response. Co-stimulatory molecules include, but are not limited to: MHC Class I molecules, TNF receptor proteins, immunoglobulin-like proteins, cytokine receptors, integrins, signaling lymphocytic activation molecules (SLAM proteins), NK cell activating receptor, BTLA, Toll ligand receptor, OX40, CD2, CD7, CD27. CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30. NKp46, CD19, CD4, CD8a, CD80, IL2Rβ, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4

(CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds to CD83.

The term "activator" or "agonist" includes substances that increase certain parameters (e.g., activity) of a given molecule (e.g., a co-stimulatory molecule). For example, this term includes substances that increase the activity (e.g., co-stimulatory activity) of a given molecule by at least 5%, 10%, 25%, 50%, 75%, or more.

The term "immune checkpoint molecule" refers to the group of molecules on the cell surface of CD4 T cells and CD8 T cells. These molecules can effectively act as "brakes" that down-regulate or suppress anti-tumor immune responses. Immune checkpoint molecules include, but are not limited to, programmed death receptor 1 (PD-1), cytotoxic T lymphocyte antigen 4 (CTLA-4), B7H1, B7H4, OX-40, CD137, CD40, and LAG-3, which directly inhibit immune cells.

The term "inhibitor" or "antagonist" includes substance that reduce certain parameters (e.g., activity) of a given molecule (e.g., an immune checkpoint inhibitory protein). For example, this term includes substances that inhibit the activity (e.g., LAG-3 activity) of a given molecule by at least 5%, 10%, 20%, 30%, 40% or more. Therefore, the inhibitory effect need not be 100%.

The term "diabody" refers to an antibody fragment having two antigen binding sites, the fragment comprising a heavy chain variable domain (VH) linked to a light chain variable domain (VL) in one polypeptide chain (VH-VL). By using a linker that is too short to pair between the two domains in each chain, the domains are forced to pair with the complementary domains of another chain to form two antigen-binding sites. Diabodies can be bivalent or bispecific. Diabodies are described in greater detail in, e.g., EP 404,097; WO 1993/01161; Hudson et al., Nat. Med. 9:129-134 (2003); and Hollinger et al., Proc. Natl. Acad. Sci. USA, 90:6444-6448 (1993). Tribodies and tetrabodies are also described in Hudson et al., Nat. Med. 9:129-134 (2003).

"Functional Fc region" possesses the "effector functions" of Fc regions of native sequences. Exemplary "effector functions" include C1q binding, CDC, Fc receptor binding, ADCC, phagocytosis, cell surface receptors (e.g., B cell receptors, or BCRs) down-regulation, and the like. Such effector functions generally require that the Fc region is associated with a binding domain (e.g., an antibody variable domain) and can be assessed using a variety of assays, such as those disclosed herein.

"Effector function" refers to biological activities which can be attributed to the antibody Fc region and vary with the antibody isotype. Examples of antibody effector functions include: C1q binding and complement-dependent cytotoxicity (CDC), Fc receptor binding, antibody-dependent cell-mediated cytotoxicity (ADCC), phagocytosis, cell surface receptors (e.g., B cell receptors) down-regulation, and B cell activation.

"Human effector cell" refers to a leukocyte that expresses one or more FcRs and executes effector functions. In certain embodiments, the cell expresses at least FcγRIII and executes effector function of ADCC. Examples of human leukocytes mediating ADCC include peripheral blood mononuclear cells (PBMC), natural killer (NK) cells, monocytes, cytotoxic T cells, and neutrophils. Effector cells can be isolated from their natural sources, such as blood.

The term "effective amount" refers to an amount or dosage of the antibody or fragment or conjugate or composition of the invention which generates expected effects in a patient in need of treatment or prevention after administered to the patient in a single or multiple doses. The effective amount can be easily determined by an attending physician as a person skilled in the art by considering a variety of factors as follows: species such as mammals; its size, age, and general health; the specific disease involved; the extent or severity of the disease; response in an individual patient; specific antibody administered; route of administration, bioavailability characteristics of the administered formulation; selected dose regimen; and use of any concomitant therapy.

"Therapeutically effective amount" refers to an amount effective to achieve a desired therapeutic outcome at a required dosage for a desired period of time. The therapeutically effective amount of an antibody or an antibody fragment, or conjugate or composition thereof can vary depending on a variety of factors such as morbid state, age, sex, and weight of an individual, and the ability of the antibody or antibody portion to elicit a desired response in the individual. The therapeutically effective amount is also such an amount in which any toxic or undesired effect of the antibody or antibody fragment, or conjugate or composition thereof is inferior to the therapeutically beneficial effect. "Therapeutically effective amount" preferably inhibits a measurable parameter (e.g., tumor growth rate) by at least about 20%, more preferably at least about 40%, even more preferably at least about 50%, 60%, or 70%, and still more preferably at least about 80% or 90%, relative to untreated subjects. The ability of a compound to inhibit a measurable parameter (e.g., cancer) can be evaluated in an animal model system that predicts efficacy in human tumors. Optionally, such property of a composition can be evaluated by examining the inhibition ability of the compound, which can be measured in vitro by assays known to those skilled.

"Prophylactically effective amount" refers to an amount effective to achieve a desired prophylactic outcome at a required dosage for a desired period of time. Generally, since a prophylactic dose is administered in a subject before or at an earlier stage of a disease, a prophylactically effective amount will be less than a therapeutically effective amount.

"Antibodies and antigen-binding fragments thereof" suitable for the invention include, but are not limited to, polyclonal, monoclonal, monovalent, bispecific, heteroconjugate, multispecific, recombinant, heterologous, heterohybrid, chimeric, humanized (especially CDR-grafted), deimmunized, or human antibody, Fab fragment, Fab' fragment, F (ab')$_2$ fragment, fragment generated from the Fab expression library, Fd, Fv, disulfide-stabilized Fv (dsFv), single chain antibody (e.g., scFv), diabody or tetrabody (Holliger P. et al. (1993) Proc. Natl. Acad. Sci. USA 90 (14), 6444-6448), nanobody (also referred to as single domain antibody), anti-idiotypic (anti-Id) antibody (including, e.g., anti-Id antibody against the antibody of the invention), and epitope binding fragment of any of the above.

"Fab" fragment includes a heavy chain variable domain and a light chain variable domain, and also includes the constant domain of the light chain and the first constant domain (CH1) of the heavy chain. An Fab' fragment differs from the Fab fragment due to addition of some residues (including one or more cysteine from an antibody hinge region) to the carboxyl terminal of the heavy chain CH1 domain. Fab'-SH refers to an Fab' in which the cysteine residue of the constant domain carries a free thiol group. An F(ab')$_2$ antibody fragment was originally generated as paired Fab' fragments with hinge cysteines between the Fab' fragments. Other chemical couplings of antibody fragments are also known.

The term "Fc region" is used herein to define a C-terminal region of an immunoglobulin heavy chain, comprising at least a portion of a constant region. The term includes Fc regions and variant Fc regions of native sequences. In certain embodiments, a human IgG heavy chain Fc region extends from Cys226 or Pro230 to the carbonyl end of the heavy chain. However, the C-terminal lysine (Lys447) of the Fc region may or may not be present. Unless otherwise stated, the numbering of amino acid residues in the Fc region or constant region is based on an EU numbering system, which is also called EU index as described in Kabat et al., Sequences of Proteins of Immunological Interest, 5$^{th}$ Ed. Public Health Service, National Institutes of Health, Bethesda, Md., 1991.

The term "variable region" or "variable domain" refers to a domain of a heavy or light chain of an antibody involved in the binding of the antibody to an antigen. Variable domains of heavy and light chains of native antibodies often have similar structures, wherein each domain contains four conserved framework regions (FR) and three complementarity determining regions (CDR). (See, e.g., Kindt et al., Kuby Immunology, 6$^{th}$ Ed., W.H. Freeman and Co. p 91 (2007)). A single VH or VL domain may be sufficient to provide antigen-binding specificity. In addition, a VH or VL domain from an antibody binding to a particular antigen can be used to isolate antibodies that bind to the antigen, so as to screen libraries of complementary VL or VH domains, respectively. See, e.g., Portolano et al., J. Immunol., 150: 880-887 (1993); Clarkson et al., Nature, 352:624-628 (1991).

"Framework" or "FR" refers to variable domain residues other than complementarity determining region CDR residues. An FR of a variable domain generally consists of four FR domains: FR1, FR2, FR3, and FR4. Therefore, CDR and FR sequences generally appear in the following sequence of heavy chain variable domain (VH) (or light chain variable domain (VL)).
FR1-HCDR1 (LCDR1)-FR2-HCDR2 (LCDR2)-FR3-HCDR3 (LCDR3)-FR4.

Unless otherwise stated, the numbering of residues in various domains of antibodies is based on the EU numbering system, which is also called EU index as described in Kabat et al., Sequences of Proteins of Immunological Interest, 5$^{th}$ Ed. Public Health Service, National Institutes of Science Health, Bethesda, Md., 1991.

The terms "full-length antibody", "whole antibody" and "intact antibody" are used interchangeably herein to refer to an antibody having a substantially similar structure to a native antibody structure or an antibody having a heavy chain that contains an Fc region as defined herein.

"Fv" is the smallest antibody fragment that contains an intact antigen-binding site. In one embodiment, a double-chain Fv type consists of one heavy chain variable domain and one light chain variable domain in a tight, non-covalently associated dimer. In a single-chain Fv (scFv) type, one heavy chain variable domain and one light chain variable domain can be covalently linked through a flexible peptide linker so that the light chain and heavy chain can be associated with a structure similar to the "Dimer" structure of the double-chain type. In this configuration, it is the three CDRs of each variable domain that define the antigen-binding site on the surface of the VH-VL dimer. To summarize, the six CDRs impart antigen-binding specificity to the antibody. Nevertheless, even a single variable domain (or containing only half Fv of the three CDRs specific to the antigen) has the ability to recognize and bind to an antigen, although the affinity is lower than an intact binding site. For a review of scFv, see, e.g., Pluckthun in The Pharmacology of Monoclonal Antibodies, Vol. 113, Edited by Rosenburg and Moore, (Springer-Verlag, New York, 1994), pages 269-315.

The terms "host cell", "host cell line" and "host cell culture" are used interchangeably and refer to cells into which an exogenous nucleic acid is introduced, including generations of such cells. Host cells include "transformants" and "transformed cells", which include primary transformed cells and generations derived therefrom, regardless of the number of passages. A generation may not be completely identical in nucleic acid content to the parent cell, but may contain mutations. Mutant generations having the same function or biological activity that are screened or selected from the initially transformed cells are included herein.

"Human antibody" refers to an antibody having an amino acid sequence which corresponds to the amino acid sequence of an antibody generated by a human or human cell or derived from a non-human source that utilizes human antibody libraries or other human antibody encoding sequences. This definition of a human antibody explicitly excludes humanized antibodies containing non-human antigen-binding residues.

"Human consensus framework" refers to a framework that represents the most frequently occurring amino acid residues in the selection of human immunoglobulin VL or VH framework sequences. Generally, the selection of human immunoglobulin VL or VH sequences is a selection from a subtype of a variable domain sequence. Generally, the subtype of the sequence is a subtype disclosed in Kabat et al., Sequences of Proteins of Immunological Interest, Fifth Edition, NIH Public Publication 91-3242, Bethesda Md. (1991), Volumes 1-3. In one embodiment, for VL, the subtype is the subtype kappa I as in Kabat et al. (see above). In one embodiment, for VH, the subtype is the subtype III as in Kabat et al. (see above).

"Humanized" antibody refers to a chimeric antibody comprising amino acid residues from non-human CDRs and amino acid residues from human FRs. In some embodiments, a humanized antibody will comprise substantially all of at least one, typically two variable domains, wherein all or substantially all CDRs (e.g., CDRs) correspond to those of a non-human antibody, and all or substantially all FRs correspond to those of a human antibody. A humanized antibody may optionally comprise at least a portion of an antibody constant region derived from a human antibody. The "humanized form" of an antibody (e.g., a non-human antibody) refers to an antibody that has been humanized.

The terms "cancer" and "cancerous" refer to or describe a physiological disease in mammals that is typically characterized by unregulated cell growth. Examples of cancers include, but are not limited to, carcinomas, lymphomas, blastomas, sarcomas, and leukemias or lymphoid malignancies. More specific examples of such cancers include, but are not limited to, squamous cell carcinoma (e.g., epithelial squamous cell carcinoma), lung cancer (including small cell lung cancer, non-small cell lung cancer, lung adenocarcinoma, and lung squamous cell carcinoma), peritoneal cancer, hepatocellular carcinoma, gastric cancer (including gastrointestinal cancer and gastrointestinal stromal cancer), pancreatic cancer, glioblastoma, cervical cancer, ovarian cancer, liver cancer, bladder cancer, urinary tract cancer, liver tumor, breast cancer, colon cancer, rectal cancer, colorectal cancer, endometrial or uterine cancer, salivary adenocarcinoma, kidney cancer, prostate cancer, vulvar cancer, thyroid cancer, liver cancer, anal cancer, penile cancer, melanoma, superficial diffuse melanoma, lentigo maligna melanoma, acral melanoma, nodular melanoma, multiple myeloma and B-cell lymphoma, chronic lymphocytic leukemia (CLL), acute lymphoblastic leukemia (ALL), hairy cell leukemia, chronic myelogenous leukemia, and post-transplant lymphoproliferative disorder (PTLD), as well as abnormal vascular proliferation associated with phakomatoses, edema (such as those associated with brain tumors), and Meigs syndrome, brain tumors and brain cancer, and head and neck cancer, and related metastases. In certain embodiments, cancers suitable for treatment by the antibodies of the invention include non-small cell lung cancer, squamous cell carcinoma, small cell lung cancer, peritoneal cancer, hepatocellular carcinoma, gastrointestinal cancer, pancreatic cancer, neuroglioma, cervical cancer, ovarian cancer, liver cancer, bladder cancer, hepatocellular carcinoma, breast cancer, colon cancer, colorectal cancer, endometrial cancer or uterine cancer, salivary gland cancer, kidney cancer, liver cancer, prostate cancer, vulvar cancer, thyroid cancer, liver cancer, leukemia, and head and neck cancer, including the metastatic forms of those cancers.

The terms "cell proliferative disorder" and "proliferative disorder" refer to disorders associated with a certain extent of abnormal cell proliferation. In one embodiment, the cell proliferative disorder refers to cancer.

The term "tumor" refers to all neoplastic cell growth and proliferation regardless of whether malignant or benign, and all pre-cancerous and cancerous cells and tissues. The terms "cancer", "cancerous". "cell proliferative disorder", "proliferative disorder", and "tumor" are not mutually exclusive when referred to herein.

The term "infectious disease" refers to a disease caused by a pathogen, including, for example, viral infection, bacterial infection, fungal infection, or protozoan such as parasitic infection.

The term "tumor immune escape" refers to tumors evading immune recognition and clearance. Therefore, as a concept of treatment, tumor immunity is "treated" and the tumor is recognized and attacked by the immune system when the escape is weakened. Examples of tumor recognition include tumor binding, tumor shrinkage, and tumor clearance.

The term "chronic infection" refers to such an infection in which an infectious agent (e.g., a pathogen such as a virus, bacteria, protozoa such as a parasite, fungus, or the like) has induced an immune response in an infected host, but has not been cleared or eliminated from the host as in acute infections. Chronic infections can be persistent, latent or slow. While acute infections are generally resolved by immune system within days or weeks (such as the flu), persistent infections can last for months, years, decades, or a lifetime at relatively lower levels (e.g., hepatitis B). In contrast, latent infections are characterized by long-term asymptomatic activity, interrupted at times by rapidly increasing hyperinfections and elevated pathogen levels (such as herpes simplex). Finally, slow infections are characterized by gradual and continuous progressions of disease symptoms, such as a long incubation period followed by prolonged and progressive clinical processes after the onset of clinical symptoms. Unlike latent and persistent infections, chronic infections may not begin in the acute phase of virus proliferation (e.g., picomaviruses infection, visna virus, scrapie, Creutzfeldt-Jakob disease). Exemplary infectious agents capable of inducing chronic infections include viruses (e.g., cytomegalovirus, EB virus, hepatitis B virus, hepatitis C virus, herpes simplex virus types I and II, human immunodeficiency virus types 1 and 2, human papilloma virus, human T lymphocyte virus types 1 and 2, varicella-zoster virus, etc.), bacteria (e.g., *Mycobacterium tuberculosis*, *Listeria* spp., *Klebsiella pneumoniae*. *Streptococcus pneumoniae*, *Staphylococcus aureus*, *Borrelia* spp., *Helicobacter pylori*, etc.), protozoa such as parasites (e.g., *Leishmania* spp., *Plasmodium falciparum*, *Schistosoma* spp., *Toxoplasma* spp., *Trypanosoma* spp., *Taenia carssiceps*, etc.), and fungi (e.g., *Aspergillus* spp., *Candida albicans*, *Coccidioides immitis*, *Histoplasma capsulatum*, *Pneumocystis carinii*, etc.). Additional infectious agents include prions or misfolded proteins which affect brain or neuron structure by further propagating protein misfolding in these tissues, leading to the formation of amyloid plaques (which cause cell death, tissue damage, and eventually, death). Examples of diseases caused by prion infections include Creutzfeldt-Jakob disease and its varieties, Gerstmann-Straussler-Scheinker syndrome (GSS), fatal familial insomnia (sFI), kuru, scrapie, bovine spongiform encephalopathy (BSE) in cattle (aka "mad cow" disease), and various other encephalopathy in various animal forms [e.g., transmissible mink encephalopathy (TME), chronic wasting disease (CWD) in white-tailed deer, elk and mule deer, feline spongiform encephalopathy, exoticungulate encephalopathy (EUE) in nyala, oryx and greater kudu, spongiform encephalopathy of the ostrich].

"Immunoconjugate" is an antibody which is conjugated to one or more other substances, including but not limited to cytotoxic agents or labels.

The term "label" used herein refers to a compound or composition which is directly or indirectly conjugated or fused to an agent, such as a polynucleotide probe or an antibody, and facilitates the detection of the agent to which it is conjugated or fused. The label itself can be detectable (e.g., a radioisotope label or a fluorescent label) or can catalyze a chemical change of a detectable substrate compound or composition in the case of enzymatic labeling. The term is intended to encompass direct labeling of a probe or an antibody by coupling (i.e., physical linking) a detectable substance to the probe or antibody and indirect labeling of a probe or an antibody by reacting with another reagent which is directly labeled. Examples of indirect labeling include detection of a primary antibody using a fluorescently labeled secondary antibody, and end labeling of a biotinylated DNA probe such that it can be detected with a fluorescently labeled streptavidin.

"Individual" or "subject" includes mammals. Mammals include, but are not limited to, domestic animals (e.g., cattle, goat, cat, dog, and horse), primates (e.g., human and non-human primates such as monkey), rabbit, and rodents (e.g., mouse and rat). In some embodiments, the individual or subject is human.

An "isolated" antibody is one that has been separated from components of its natural environment. In some embodiments, the antibody is purified to a purity greater than 95% or 99% as determined by, e.g., electrophoresis [e.g., SDS-PAGE, isoelectric focusing (IEF), capillary electrophoresis] or chromatography (e.g., ion exchange or reversed phase HPLC). For a review of methods for assessing antibody purity, see, e.g., Flatman et al., J. Chromatogr., B848:79-87 (2007).

An "isolated" nucleic acid refers to a nucleic acid molecule which has been separated from components of its natural environment. The isolated nucleic acid includes a nucleic acid molecule contained in a cell that normally contains the nucleic acid molecule, but present extrachromosomally or at a chromosomal location that is different from its natural chromosomal location.

"An isolated nucleic acid encoding an anti-PD-L1 antibody or a fragment thereof" refers to one or more nucleic acid molecules encoding the antibody heavy or light chain (or fragment thereof), including such nucleic acid molecules in a single vector or separate vectors, and such nucleic acid molecules present at one or more locations in a host cell.

The terms "nucleic acid", "nucleic acid sequence", "nucleotide sequence" or "polynucleotide sequence" and "polynucleotide" are used interchangeably. They refer to nucleotides (deoxyribonucleotides or ribonucleotides) of any length in polymer form or analogs thereof. A polynucleotide may be single-stranded or double-stranded, and if single-stranded, may be a coding or non-coding (antisense) strand. Polynucleotides can include modified nucleotides, such as methylated nucleotides and nucleotide analogs. The sequence of nucleotide can be interrupted by non-nucleotide components. The polynucleotide may be further modified after polymerization, such as by conjugation with a labeling component. A nucleic acid can be a recombinant polynucleotide or a polynucleotide which does not exist in nature, or is linked in an unnatural layout to another polynucleotide from genomic source, cDNA source, semi-synthetic source, or synthetic source.

The terms "polypeptide", "peptide" and "protein" (if in single chain) are used interchangeably herein and refer to amino acid polymers of any length. The polymer can be linear or branched, can comprise modified amino acids, and can be interrupted by non-amino acids. The term also includes amino acid polymers which have been modified (e.g., formation of disulfide bond, glycosylation, lipidation, acetylation, phosphorylation, or any other operation such as conjugation with a labeling component). Polypeptides can be isolated from natural sources, can be produced from eukaryotic or prokaryotic hosts via recombinant techniques, and can be the products of synthetic methods.

The calculation of sequence identity between sequences is performed as follows.

To determine the percent identity of two amino acid sequences or two nucleic acid sequences, the sequences are aligned for optimal comparison purposes (e.g., for optimal alignment, gaps can be introduced in the first and second amino acid sequences or in one or both of nucleic acid sequences, or non-homologous sequences can be discarded for comparison purposes). In one preferred embodiment, for comparison purposes, the length of the aligned reference sequence is at least 30%, preferably at least 40%, more preferably at least 50%, 60%, and even more preferably at least 70%, 80%, 90%, 100% of the length of the reference sequence. Amino acid residues or nucleotides at corresponding amino acid positions or nucleotide positions are then compared. When a position in the first sequence is occupied by the same amino acid residue or nucleotide at the corresponding position in the second sequence, then the molecules are identical at this position.

A mathematical algorithm can be used to achieve the sequence comparison and calculation of percent identity between two sequences. In one preferred embodiment, the percent identity between two amino acid sequences is determined with the Needlema and Wunsch [(1970) J. Mol. Biol., 48:444-453] algorithm (available at http://www.gcg.com) which has been integrated into the GAP program of the GCG software package, using the Blossom 62 matrix or PAM250 matrix and gap weights of 16, 14, 12, 10, 8, 6, or 4 and length weights of 1, 2, 3, 4, 5, or 6. In yet another preferred embodiment, the percent identity between two nucleotide acid sequences is determined with the GAP program (available at http://www.gcg.com) of the GCG software package, using the NWSgapdna.CMP matrix and gap weight of 40, 50, 60, 70, or 80 and length weight of 1, 2, 3, 4, 5 or 6. A particularly preferred parameter set (and one that should be used unless otherwise stated) is a Blossom 62 scoring matrix with a gap penalty of 12, a gap extension penalty of 4, and a frameshift gap penalty of 5.

The percent identity between two amino acid sequences or nucleotide sequences can also be determined with PAM120 weighted remainder table, gap length penalty of 12 and gap penalty of 4, using the E. Meyers and W. Miller algorithms which have been incorporated into the ALIGN program (version 2.0) ((1989) CABIOS, 4:11-17).

Additionally or alternatively, the nucleic acid sequences and protein sequences described herein can be further used as "query sequences" to perform searches against public databases to, e.g., identify other family member sequences or related sequences. For example, such searches can be performed using the NBLAST and XBLAST programs of Altschul et al., (1990) J. Mol. Biol., 215:403-10. BLAST nucleotide searches can be performed with the NBLAST program, score=100, word length=12, to obtain nucleotide sequences homologous to the nucleic acid molecule of the invention. BLAST protein searches can be performed with the XBLAST program, score=50, word length=3, to obtain amino acid sequences homologous to the protein molecule of the invention. To obtain gapped alignment results for comparison purposes, gapped BLAST can be used as described in Altschul et al. (1997) Nucleic Acids Res. 25:3389-3402. When using BLAST and gapped BLAST programs, the default parameters of the respective programs (e.g., XBLAST and NBLAST) can be used. See http://www.ncbi.nlm.nih.gov.

As used herein, the term "hybridization under conditions of low stringency, medium stringency, high stringency, or extreme stringency" describes hybridization and washing conditions. Instructions for performing hybridization reactions can be found in Current Protocols in Molecular Biology, John Wiley & Sons, N.Y. (1989), 6.3.1-6.3.6, which is incorporated by reference. Aqueous and non-aqueous methods are described in the references and either method can be used. The specific hybridization conditions mentioned herein are as followed: 1) low stringency hybridization conditions are in 6× sodium chloride/sodium citrate (SSC) at about 45° C., followed by two washes in 0.2×SSC, 0.1% SDS at least at 50° C. (for low stringency conditions, the temperature of the washes can be increased to 55° C.), 2) medium stringency hybridization conditions are in 6×SSC at about 45° C. followed by one or more washes in 0.2×SSC, 0.1% SDS at about 60° C.; 3) high stringency hybridization conditions are in 6×SSC at about 45° C., followed by one or more washes in 0.2×SSC, 0.1% SDS at 65° C.; and preferably 4) extreme stringency hybridization conditions are in 0.5 M sodium phosphate, 7% SDS at 65° C., followed by one or more washes in 0.2×SSC, 0.1% SDS at 65° C. Extreme stringency condition (4) is a preferred condition and the one that should be used unless otherwise stated.

The term "pharmaceutical composition" refers to such a composition that exists in a form which allows the biological activity of the active ingredient contained therein to be effective, and does not contain additional ingredients having unacceptable toxicity to a subject to which the composition is administered.

The term "pharmaceutical supplementary materials" refers to diluents, adjuvants (e.g., Freund's adjuvants (complete and incomplete)), excipients, carriers or stabilizers, etc., which are administered with the active substance.

As used herein, "treatment" (or "treat" or "treating") refers to slowing, interrupting, arresting, alleviating, stopping, reducing, or reversing the progression or severity of an existing symptom, disorder, condition, or disease.

As used herein, "prevention" (or "prevent" or "preventing") includes the inhibition of the onset or progression of a disease or disorder or a symptom of a particular disease or disorder. In some embodiments, subjects with family history of cancer are candidates for preventive regimens. Generally, in the context of cancer, the term "prevention" refers to the administration of a drug prior to the onset of signs or symptoms of a cancer, particularly in subjects at risk of cancer.

The term "anti-infective agent" includes any molecule that specifically inhibits or eliminates the growth of microorganisms such as viruses, bacteria, fungi, or protozoa, e.g., parasites, and is not lethal to the host, at the administration concentration and interval of administration. As used herein, the term anti-infective agent includes antibiotics, antibacterials, antivirals, antifungals, and antiprotozoals. In one specific aspect, the anti-infective agent is non-toxic to the host at the administration concentration and interval of administration.

Antibacterial anti-infective agents or antibacterial agents can be broadly classified into bactericidal (i.e., directly killing) or bacteriostatic (i.e., preventing division). Antibacterial anti-infective agents can be further classified into narrow-spectrum antibacterial agents (i.e., affecting only limited bacterial subtypes, such as Gram-negative, etc.) or broad-spectrum antibacterial agents (i.e., affecting a wide range of species). Examples include amikacin, gentamicin, geldanamycin, herbimycin, mupirocin, furantoin, pyrazinamide, quinupristin/dalfopristin, rifampicin/rifampin, isoniazid and pyrazinamide tablets, or tinidazole.

The term "antiviral" includes any substance that inhibits or eliminates the growth, pathogenicity, and/or survival of a virus. This includes, e.g., acyclovir, cidofovir, zidovudine, didanosine (ddI, VIDEX), zalcitabine (ddC, HIVID), stavudine (d4T, ZERIT), lamivudine (3TC, EPIVIR), abacavir (ZIAGEN), emtricitabine (EMTRIVA), etc.

The term "antifungal" includes any substance that inhibits or eliminates the growth, pathogenicity, and/or survival of a fungus. This includes, e.g., natamycin, rimocidin, filipin, nystatin, amphotericin B, candicin, patchouli, neem seed oil, coconut oil, etc.

The term "antiprotozoal" includes any substance that inhibits or eliminates the growth, pathogenicity, and/or survival of protozoan organisms (e.g., parasites). Examples of antiprotozoal agents include antimalarials such as quinine, quinidine, etc.

For exemplary antibacterials, antivirals, antifungals, and antiprotozoals, see, e.g., WO2010/077634 and the like.

For anti-infective agents, see also, e.g., WO2014/008218, WO2016/028672, WO2015/138920 or WO2016/061142.

The term "vector" as used herein refers to a nucleic acid molecule capable of proliferating another nucleic acid to which it is linked. The term includes vectors that serve as self-replicating nucleic acid structures as well as vectors binding to the genome of a host cell into which they have been introduced. Some vectors are capable of directing the expression of a nucleic acid to which they are operably linked. Such vectors are called "expression" vectors herein.

"Subject/patient sample" refers to a collection of cells or fluids obtained from a patient or subject. The source of the tissue or cell samples can be solid tissues, e.g., from fresh, frozen and/or preserved organ or tissue samples or biopsy samples or puncture samples; blood or any blood component; body fluids such as cerebrospinal fluids, amniotic fluids, peritoneal fluids, or interstitial fluids; cells from a subject at any time during pregnancy or development. Tissue samples may comprise compounds which are naturally not mixed with tissues, such as preservatives, anticoagulants, buffers, fixatives, nutrients, antibiotics, and the like. Examples of tumor samples include but are not limited to tumor biopsies, fine needle aspirates, bronchial lavage fluids, pleural fluids, sputa, urine, surgical specimens, circulating tumor cells, serum, plasma, circulating plasma proteins, ascites, primary cell cultures or cell lines derived from tumors or exhibiting tumor-like properties, and preserved tumor samples such as formalin-fixed, paraffin-embedded tumor samples or frozen tumors samples.

The term "package insert" is used to refer to the instructions generally contained in the commercial package of therapeutic products, which contain information about indications, usage, dosage, administration, combination therapies, contraindications and/or warnings related to the application of such therapeutic products.

Antibody of the Invention

Therefore, in some embodiments, the antibody or fragment thereof of the invention binds to PD-L1. In some embodiments, the antibody or fragment thereof of the invention binds to mammalian PD-L1, such as human PD-L1. For example, the antibody molecule specifically binds to an epitope (e.g., a linear or conformational epitope) of PD-L1. In some embodiments, the antibody molecule binds to one or more extracellular domains of PD-L1.

In some embodiments, the anti-PD-L1 antibody or fragment thereof of the invention has one or more of the following properties:

(1) The anti-PD-L1 antibody or the fragment thereof of the invention binds to PD-L1 (e.g., human PD-L1) with high affinity, for example, binds to PD-L1 with an equilibrium dissociation constants ($K_D$) of less than about 50 nM, preferably less than or equal to about 20 nM, more preferably less than or equal to about 15 nM, more preferably less than or equal to about 10 nM, 9 nM, 8 nM, 7 nM, 6 nM, 5 nM, 4 nM, 3 nM, or 2 nM, and most preferably less than or equal to about 1.5 nM, 1.4 nM, 1.3 nM, 1.2 mM, 1.1 nM, 1 nM, 0.9 nM, or 0.8 nM. In some embodiments, the anti-PD-L1 antibody of the invention binds to PD-L1 with a $K_D$ of 0.1-10 nM, preferably 0.5-10 nM, more preferably 0.6-10 nM, 0.7-8 nM, and 0.7-5 nM, and most preferably 0.5-1.5 nM, 0.7-1.5 nM, and 0.7-1 nM. In some embodiments, the PD-L1 is a human PD-L1. In some embodiments, the antibody binding affinity is determined using biological optical interferometry (e.g., Fortebio affinity measurement).

(2) The antibody or the fragment thereof of the invention binds to cells expressing human PD-L1, for example, with an $EC_{50}$ of less than or equal to about 4 nM, 3.5 nM, 3 nM, 2.9 nM, 2.8 nM, 2.7 nM, 2.6 nM, 2.5 nM, 2.4 nM, 2.3 nM, 2.2 nM, 2.1 nM, 2 nM, 1.9 nM, 1.8 nM, 1.7 nM, or 1.6 nM. In some embodiments, the binding is determined using flow cytometry (e.g., FACS). In some embodiments, the cell expressing human PD-L1 is a CHO cell expressing human PD-L1.

(3) The antibody or the fragment thereof of the invention blocks relevant activities of PD-L1, for example, with an $EC_{50}$ of less than or equal to about 10 nM, 5 nM, 4 nM, 3 nM, 2 nM, 1 nM, 0.9 nM, 0.8 nM, or 0.7 nM, and preferably 0.1-1 nM, 0.5-1 nM, 0.6-1 nM, 0.6 nM, 0.7 nM, 0.8 nM, 0.9 nM, or 1 nM. In some embodiments, the relevant activity of PD-L1 is the binding of PD-L1 to PD-1. In some embodiments, the antibody or the fragment thereof of the invention inhibits the binding of PD-L1 to PD-1 with an $EC_{50}$ of less than or equal to about 10 nM, 5 nM, 4 nM, 3 nM, 2 nM, 1 nM, 0.9 nM, 0.8 nM, or 0.7 nM, and preferably 0.1-1 nM, 0.5-1 nM, 0.6-1 nM, 0.6 nM, 0.7 nM, 0.8 nM, 0.9 nM, or 1 nM in an MOA assay. In some embodiments, the cell is a CHO cell.

(4) The ability of the antibody or the fragment thereof of the invention to improve T cell function, e.g., is superior to known anti-PD-L1 antibodies, such as Tecentriq.

(5) The ability of the antibody or the fragment thereof of the invention to activate T cells, for example in MLR, e.g., is superior to known anti-PD-L1 antibodies, such as Tecentriq.

(6) The ability of the antibody or the fragment thereof of the invention to increase IFN-γ secretion, for example in MLR, e.g., is superior to known anti-PD-L1 antibodies, such as Tecentriq.

(7) The ability of the antibody or the fragment thereof of the invention to increase IL-2 secretion, for example in MLR, e.g., is superior to known anti-PD-L1 antibodies, such as Tecentriq.

(8) The antibody or the fragment thereof of the invention is less viscous than known anti-PD-L1 antibody (e.g., Tecentriq), and therefore has better druggability. In some embodiments, the antibody or the fragment thereof of the invention has a retention time (RT) of less than about 10 minutes, about 9 minutes, or about 8 minutes, preferably about 7-9 minutes, and preferably about 7-8.5 minutes, about 7.5-8.5 minutes, about 7-8 minutes, or about 7.5-8 minutes, such as about 7.5 minutes, 7.6 minutes, 7.7 minutes, 7.8 minutes, 7.9 minutes, 8 minutes, 8.1 minutes, 8.2 minutes, 8.3 minutes, 8.4 minutes, 8.5 minutes, in a Zenix column chromatography.

(9) The antibody or the fragment thereof of the invention inhibits one or more activities of PD-L1, for example, causing one or more of the following: increased tumor-infiltrating lymphocytes, increased T cell receptor-mediated proliferation, or decreased immune evasion of cancer cells.

(10) The anti-PD-L1 antibody or the fragment thereof of the invention can induce antibody-dependent cell-mediated cytotoxicity (ADCC).

In some embodiments, the anti-PD-L1 antibody or the antigen-binding fragment thereof of the invention has one or more of the following characteristics:

(i) showing the same or similar binding affinity and/or specificity for PD-L1 as the antibody of the invention (e.g., any of the antibodies listed in Table 3);

(ii) inhibiting (e.g., competitively inhibiting) the binding of the antibody of the invention (e.g., any of the antibodies listed in Table 3) to PD-L1;

(iii) binding to the same or overlapping epitope as the antibody of the invention (e.g., any of the antibodies listed in Table 3);

(iv) competing with the antibody of the invention (e.g., any of the antibodies listed in Table 3) for binding to PD-L1;

(v) having one or more biological characteristics of the antibody of the invention (e.g., any of the antibodies listed in Table 3).

Exemplary Antibodies

In some embodiments, the anti-PD-L1 antibody or the antigen-binding fragment thereof of the invention comprises a heavy chain variable region (VH), wherein the VH comprises:

(i) three complementary determining regions (CDRs) contained in a VH of any of the antibodies listed in Table B, or (ii) relative to the sequence of (i), a sequence comprising a total of at least one and no more than 5, 4, 3, 2 or 1 amino acid alternation (preferably amino acid substitution, preferably conservative substitution) in the three CDR regions.

In some embodiments, the anti-PD-L1 antibody or the antigen-binding fragment thereof of the invention comprises a light chain variable region (VL), wherein the VL comprises:

(i) three complementary determining regions (CDRs) contained in a VL of any of the antibodies listed in Table B, or (ii) relative to the sequence of (i), a sequence comprising a total of at least one and no more than 5, 4, 3, 2 or 1 amino acid alternation (preferably amino acid substitution, preferably conservative substitution) in the three CDR regions.

In some embodiments, the anti-PD-L1 antibody or antigen-binding fragment thereof of the invention comprises a heavy chain variable region VH and a light chain variable region VL, wherein (a) the VH comprises:
(i) three complementary determining regions (CDRs) contained in a VH of any of the antibodies listed in Table B. or (ii) relative to the sequence of (i), a sequence comprising a total of at least one and no more than 5, 4, 3, 2 or 1 amino acid alternation (preferably amino acid substitution, preferably conservative substitution) in the three CDR regions; and/or (b) the VL comprises:
(i) three complementary determining regions (CDRs) contained in a VL of any of the antibodies listed in Table B. or (ii) relative to the sequence of (i), a sequence comprising a total of at least one and no more than 5, 4, 3, 2 or 1 amino acid alternation (preferably amino acid substitution, preferably conservative substitution) in the three CDR regions.

In a preferred embodiment, the VH comprises or consists of an amino acid sequence selected from the group consisting of SEQ ID NO: 26, 27, 28, 29, 30, or 31.

In a preferred embodiment, the VL comprises or consists of an amino acid sequence selected from the group consisting of SEQ ID NO: 32, 33, 34, 35, 36, or 37.

In a preferred embodiment, the anti-PD-L1 antibody or the antigen-binding fragment thereof of the invention comprises:

(i) three complementary determining regions HCDRs of the heavy chain variable region shown in SEQ ID NO: 26 or 30, and three complementary determining regions LCDRs of the light chain variable region shown in SEQ ID NO: 32 or 36, or (ii) three complementary determining regions HCDRs of the heavy chain variable region shown in SEQ ID NO: 27, and three complementary determining regions LCDRs of the light chain variable region shown in SEQ ID NO: 33, or (iii) three complementary determining regions HCDRs of the heavy chain variable region shown in SEQ ID NO: 28, and three complementary determining regions LCDRs of the light chain variable region shown in SEQ ID NO: 34, or (iv) three complementary determining regions HCDRs of the heavy chain variable region shown in SEQ ID NO: 29 or 31, and three complementary determining regions LCDRs of the light chain variable region shown in SEQ ID NO: 35 or 37.

In some embodiments, the anti-PD-L1 antibody or the antigen-binding fragment thereof of the invention comprises a heavy chain variable region (VH) and/or a light chain variable region (VL), wherein (i) the VH comprises complementary determining regions (CDRs), HCDR1, HCDR2, and HCDR3, wherein the HCDR1 comprises or consists of an amino acid sequence selected from the group consisting of SEQ ID NO: 1, 2, 3, or 4, or the HCDR1 comprises an amino acid sequence having one, two, or three alternations (preferably amino acid substitutions, preferably conservative substitutions) compared to an amino acid sequence selected from the group consisting of SEQ ID NO: 1, 2, 3, or 4; the HCDR2 comprises or consists of an amino acid sequence selected from the group consisting of SEQ ID NO: 5, 6, 7, 8, or 9, or the HCDR2 comprises an amino acid sequence having one, two, or three alternations (preferably amino acid substitutions, preferably conservative substitutions) compared to an amino acid sequence selected from the group consisting of SEQ ID NO: 5, 6, 7, 8, or 9; the HCDR3 comprises or consists of an amino acid sequence selected from the group consisting of SEQ ID NO: 10, 11, 12, or 13, or the HCDR3 comprises an amino acid sequence having one, two, or three alternations (preferably amino acid substitutions, preferably conservative substitutions) compared to an amino acid sequence selected from the group consisting of SEQ ID NO: 10, 11, 12, or 13;

and/or (ii) the VL comprises complementary determining regions (CDRs), LCDR1, LCDR2, and LCDR3, wherein the LCDR1 comprises or consists of an amino acid sequence selected from the group consisting of SEQ ID NO: 14, 15, or 16, or the LCDR1 comprises an amino acid sequence having one, two, or three alternations (preferably amino acid substitutions, preferably conservative substitutions) compared to an amino acid sequence selected from the group consisting of SEQ ID NO: 14, 15, or 16; the LCDR2 comprises or consists of an amino acid sequence selected from the group consisting of SEQ ID NO: 17, 18, 19, or 20, or the LCDR2 comprises an amino acid sequence having one, two, or three alternations (preferably amino acid substitutions, preferably conservative substitutions) compared to an amino acid sequence selected from the group consisting of SEQ ID NO: 17, 18, 19, or 20; the LCDR3 comprises or consists of an amino acid sequence selected from the group consisting of SEQ ID NO: 21, 22, 23, 24, or 25, or the LCDR3 comprises an amino acid sequence having one, two, or three alternations (preferably amino acid substitutions, preferably conservative substitutions) compared to an amino acid sequence selected from the group consisting of SEQ ID NO: 21, 22, 23, 24, or 25.

In a preferred embodiment, the invention provides an anti-PD-L1 antibody or an antigen-binding fragment thereof comprising a heavy chain variable region (VH) and/or a light chain variable region (VL), wherein (a) the VH comprises:

(i) a combination of HCDR1, HCDR2, and HCDR3 shown in Table A; or (ii) a variant of an HCDR combination of (i), comprising a total of at least one and no more than 5, 4, 3, 2, or 1 amino acid alternation (preferably amino acid substitution, preferably conservative substitution) in the three CDR regions;

and/or (b) the VL comprises:

(i) a combination of LCDR1. LCDR2 and LCDR3 shown in Table A; or (ii) a variant of an LCDR combination of (i), comprising a total of at least one and no more than 5, 4, 3a 2 or 1 amino acid alternation (preferably amino acid substitution, preferably conservative substitution) in the three CDR regions.

In a preferred embodiment, the invention provides an anti-PD-L1 antibody or an antigen-binding fragment thereof, comprising a heavy chain variable region (VH) and a light chain variable region (VL), wherein the VH comprises complementary determining regions (CDRs), HCDR1, HCDR2, and HCDR3, and the VL comprises CDRs, LCDR1, LCDR2, and LCDR3, wherein combinations of HCDR1, HCDR2, HCDR3, LCDR1, LCDR2, and LCDR3 contained in the antibody or the antigen-binding fragment thereof are shown in the following table (Table A):

TABLE A

Exemplary combinations of HCDR1, HCDR2, HCDR3, LCDR1, LCDR2, and LCDR3 in the antibody or the antigen-binding fragment thereof of the invention

| Combinations | HCDR1, which comprises or consists of an amino acid sequence shown in the following SEQ ID NOs | HCDR2, which comprises or consists of an amino acid sequence shown in the following SEQ ID NOs | HCDR3, which comprises or consists of an amino acid sequence shown in the following SEQ ID NOs | LCDR1, which comprises or consists of an amino acid sequence shown in the following SEQ ID NOs | LCDR2, which comprises or consists of an amino acid sequence shown in the following SEQ ID NOs | LCDR3, which comprises or consists of an amino acid sequence shown in the following SEQ ID NOs |
|---|---|---|---|---|---|---|
| (1) | SEQ ID NO: 1 | SEQ ID NO: 5 | SEQ ID NO: 10 | SEQ ID NO: 14 | SEQ ID NO: 17 | SEQ ID NO: 21 |
| (2) | SEQ ID NO: 2 | SEQ ID NO: 6 | SEQ ID NO: 11 | SEQ ID NO: 15 | SEQ ID NO: 18 | SEQ ID NO: 22 |
| (3) | SEQ ID NO: 2 | SEQ ID NO: 7 | SEQ ID NO: 12 | SEQ ID NO: 15 | SEQ ID NO: 18 | SEQ ID NO: 23 |
| (4) | SEQ ID NO: 3 | SEQ ID NO: 8 | SEQ ID NO: 13 | SEQ ID NO: 16 | SEQ ID NO: 19 | SEQ ID NO: 24 |
| (5) | SEQ ID NO: 4 | SEQ ID NO: 9 | SEQ ID NO: 10, 11, 12, or 13 | SEQ ID NO: 14, 15, or 16 | SEQ ID NO: 20 | SEQ ID NO: 25 |

In some embodiments, the anti-PD-L1 antibody or the antigen-binding fragment thereof of the invention comprises a heavy chain variable region VH and/or a light chain variable region VL, wherein, (a) the heavy chain variable region VH (i) comprises or consists of an amino acid sequence having at least 90%, 91%, 92%, 93%, 94%, 95%, 96%, 97%, 98% or 99% identity to an amino acid sequence selected from SEQ ID NO: 26, 27, 28, 29, 30, or 31;

(ii) comprises or consists of an amino acid sequence selected from the group consisting of SEQ ID NO: 26, 27, 28, 29, 30, or 31; or (iii) comprises an amino acid sequence having 1 or more (preferably not more than 10, more preferably not more than 5, 4, 3, 2 or 1) amino acid alterations (preferably amino acid substitutions, more preferably amino acid conservative substitutions) as compared to an amino acid sequence selected from the SEQ ID NO: 26, 27, 28, 29, 30, or 31, wherein preferably, the amino acid alterations do not occur in the CDRs:

and/or (b) the light chain variable region VL (i) comprises or consists of an amino acid sequence having at least 90%, 91%, 92%, 93%, 94%, 95%, 96%, 97%, 98% or 99% identity to an amino acid sequence selected from SEQ ID NO: 32, 33, 34, 35, 36, or 37;

(ii) comprises or consists of an amino acid sequence selected from the group consisting of SEQ ID NO: 32, 33, 34, 35, 36, or 37; or (iii) comprises an amino acid sequence having 1 or more (preferably not more than 10, more preferably not more than 5, 4, 3, 2 or 1) amino acid alterations (preferably amino acid substitutions, more preferably amino acid conservative substitutions) as compared to an amino acid sequence selected from the SEQ ID NO: 32, 33, 34, 35, 36, or 37, wherein preferably, the amino acid alterations do not occur in the CDRs.

In a preferred embodiment, the invention provides an anti-PD-L1 antibody or an antigen-binding fragment thereof, comprising a heavy chain variable region (VH) and a light chain variable region (VL), wherein combinations of the heavy chain variable region VH and light chain variable region VL contained in the antibody or the antigen-binding fragment thereof are shown in the following table (Table B):

TABLE B

Exemplary combinations of heavy chain variable region VH and light chain variable region VL in the antibody or the antigen-binding fragment thereof of the invention

| Combinations | VH, which comprises or consists of the amino acid sequence shown in the following SEQ ID NO | VL, which comprises or consists of the amino acid sequence shown in the following SEQ ID NO |
|---|---|---|
| (1) | SEQ ID NO: 26 | SEQ ID NO: 32 |
| (2) | SEQ ID NO: 27 | SEQ ID NO: 33 |
| (3) | SEQ ID NO: 28 | SEQ ID NO: 34 |
| (4) | SEQ ID NO: 29 | SEQ ID NO: 35 |
| (5) | SEQ ID NO: 30 | SEQ ID NO: 36 |
| (6) | SEQ ID NO: 31 | SEQ ID NO: 37 |

In some embodiments, the anti-PD-L1 antibody or the antigen-binding fragment thereof of the invention comprises a heavy chain and/or a light chain, wherein (a) the heavy chain (i) comprises or consists of an amino acid sequence having at least 85%, 90%, 91%, 92%, 93%, 94%, 95%, 96%, 97%, 98% or 99% identity to an amino acid sequence selected from SEQ ID NO: 38, 39, 40, 41, 42, 43, 44, or 45:

(ii) comprises or consists of an amino acid sequence selected from the group consisting of SEQ ID NO: 38, 39, 40, 41, 42, 43, 44, or 45; or (iii) comprises an amino acid sequence having 1 or more (preferably no more than 20 or 10, more preferably no more than 5, 4, 3, 2 or 1) amino acid alterations (preferably amino acid substitutions, more preferably amino acid conservative substitutions) as compared to an amino acid sequence selected from the SEQ ID NO: 38, 39, 40, 41, 42, 43, 44 or 45, wherein preferably, the amino acid alterations do not occur in the CDRs of the heavy chain, and more preferably, the amino acid alterations do not occur in the heavy chain variable region; and/or (b) the light chain (i) comprises or consists of an amino acid sequence having at least 85%, 90%, 91%, 92%, 93%, 94%, 95%, 96%, 97%, 98% or 99% identity to an amino acid sequence selected from SEQ ID NO: 46, 47, 48, 49, 50, or 51;

(ii) comprises or consists of an amino acid sequence selected from the group consisting of SEQ ID NO: 46, 47, 48, 49, 50, or 51; or (iii) comprises an amino acid sequence having 1 or more (preferably no more than 20 or 10, more preferably no more than 5, 4, 3, 2 or 1) amino acid alterations (preferably amino acid substitutions, more preferably amino acid conservative substitutions) as compared to an amino acid sequence selected from the SEQ ID NO: 46, 47, 48, 49, 50 or 51, wherein preferably, the amino acid alterations do not occur in the CDRs of the light chain, and more preferably, the amino acid alterations do not occur in the light chain variable region;

In a preferred embodiment, the invention provides an anti-PD-L1 antibody or an antigen-binding fragment thereof, comprising a heavy chain and a light chain, wherein the combinations of the heavy and light chains contained in the antibody or the antigen-binding fragment thereof are shown in the following table (Table C):

TABLE C

Exemplary combinations of heavy chain and light chain in the antibody or the antigen-binding fragment thereof of the invention

| Combinations | HC, which comprises or consists of the amino acid sequence shown in the following SEQ ID NO | LC, which comprises or consists of the amino acid sequence shown in the following SEQ ID NO |
|---|---|---|
| (1) | SEQ ID NO: 38 | SEQ ID NO: 46 |
| (2) | SEQ ID NO: 39 | SEQ ID NO: 47 |
| (3) | SEQ ID NO: 40 | SEQ ID NO: 48 |
| (4) | SEQ ID NO: 41 | SEQ ID NO: 49 |
| (5) | SEQ ID NO: 42 | SEQ ID NO: 50 |
| (6) | SEQ ID NO: 43 | SEQ ID NO: 50 |
| (7) | SEQ ID NO: 44 | SEQ ID NO: 50 |
| (8) | SEQ ID NO: 45 | SEQ ID NO: 51 |

In some embodiments, the heavy chain and/or light chain of the anti-PD-L1 antibody or the fragment thereof of the invention further comprises a signal peptide sequence, such as METDTLLLWVLLLWVPGSTG (SEQ ID NO: 68).

In one embodiment of the invention, the amino acid alternation described herein includes amino acid substitution, insertion, or deletion. Preferably, the amino acid alternation described herein is amino acid substitution, preferably conservative substitution.

In a preferred embodiment, the amino acid alteration described herein occurs in regions outside the CDRs (e.g., in FRs). More preferably, the amino acid alternation described herein occurs in regions outside the heavy chain variable region and/or outside the light chain variable region.

Optionally, the anti-PD-L1 antibody of the invention comprises post-translational modifications to the light chain variable region, the heavy chain variable region, the light chain, or the heavy chain. Exemplary post-translational modifications include disulfide bond formation, glycosylation, lipidation, acetylation, phosphorylation, or any other operations, such as conjugation with a labeling component.

In some embodiments, the substitution is a conservative substitution. A conservative substitution refers to a replacement of an amino acid by another amino acid of the same class, e.g., an acidic amino acid replacement by another acidic amino acid, a basic amino acid replacement by another basic amino acid, or a neutral amino acid replacement by another neutral amino acid. Exemplary substitutions are shown in Table D below:

TABLE D

| Original residue | Exemplary substitution | Preferred substitution |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; norleucine | Leu |
| Leu (L) | norleucin; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; norleucine | Leu |

In certain embodiments, the antibody provided herein is altered to increase or decrease the extent to which the antibody is glycosylated. Addition or deletion of glycosylation sites to an antibody can be conveniently achieved by altering the amino acid sequence such that one or more glycosylation sites are created or removed.

For example, one or more amino acid substitutions can be performed to eliminate one or more variable region framework glycosylation sites, thereby eliminating glycosylation at that site. Such aglycosylation can increase the affinity of an antibody for an antigen. See, e.g., U.S. Pat. Nos. 5,714,350 and 6,350,861. Antibodies with altered classes of glycosylation can be prepared, such as low fucosylated antibodies with reduced amounts of fucosyl residues or antibodies with increased bisecting GlcNac structures. Such altered glycosylation patterns have shown the ability to increase ADCC of antibodies. Such carbohydrate modifications can be achieved by, e.g., expressing antibodies in host cells with altered glycosylation systems. Cells with altered glycosylation systems have been described in the art and can be used as host cells in which the antibodies of the invention are expressed to thereby produce antibodies with altered glycosylation. For example, cell lines Ms704, Ms705, and Ms709 lack the fucosyltransferase gene FUT8 ($\alpha(1,6)$-fucosyltransferase), such that antibodies expressed in cell lines Ms704, Ms705, and Ms709 lack fucose in their carbohydrates. Cell lines Ms704, Ms705, and Ms709FUT8−/− are created by using two alternative vectors to target the FUT8 gene in the CHO/DG44 cells for disruption (see US Patent Publication No. 20040110704 and Yamane-Ohnuki et al. (2004) Biotechnol Bioeng 87:614-22). EP 1,176,195 describes cell lines with a functionally disrupted FUT8 gene encoding a fucosyltransferase, such that antibodies expressed in the cell lines exhibit low fucosylation by reducing or eliminating $\alpha$-1,6 bond-related enzymes. EP 1,176,195 also describes cell lines with low or no enzymatic activity which adds fucose to N-acetylglucosamine binding to Fc regions of an antibody, such as rat myeloma cell line YB2/0 (ATCC CRL 1662). PCT publication WO03/035835 describes a variant CHO cell line Lec13 cells, in which the ability of attaching fucose to Asn (297)-linked carbohydrates is reduced, thereby also leading to low fucosylation of antibodies expressed in the host cell (see also Shields et al. (2002) J. Biol. Chem. 277:26733-26740). Antibodies with modified glycosylation profiles can also be produced in eggs, as described in PCT publication WO06/089231. Alternatively, antibodies with modified glycosylation profiles can be produced in plant cells, such as Lemna. A method for producing antibodies in plant systems is disclosed in a US patent application filed on Aug. 11, 2006, corresponding to Alston and Bird LLP. 60/856,998. PCT publication WO99/54342 describes a cell line engineered to express a glycoprotein modifying glycosyltransferase [such as $\beta(1,4)$-N-acetylglucosaminyltransferase III (GnTIII)], thereby antibodies expressed in the engineered cell line exhibit increased bisecting GlcNac structures, which results in increased ADCC activity of the antibody [see also Umana et al. (1999) Nat. Biotech. 17:176-180]. Alternatively, fucosidase can be used to cut fucosyl residues off the antibody; for example, $\alpha$-L-fucosidase removes fucosyl residues from the antibody [Tarentino et al. (1975) Biochem. 14:5516-23].

In one embodiment of the invention, the antibody or the fragment of the invention is glycosylated with an engineered yeast N-linked glycan or CHO N-linked glycan.

Another modification encompassed by the invention to the antibody or the fragment thereof described herein is PEGylation. An antibody can be PEGylated to, e.g. increase the biological (e.g., serum) half-life of the antibody. To PEGylate an antibody, the antibody or the fragment thereof typically reacts with polyethylene glycol (PEG) (such as a reactive ester or aldehyde derivative of PEG) in a condition where one or more PEG groups become attached to the antibody or antibody fragment. Preferably, PEGylation is performed via an acylation reaction or an alkylation reaction using a reactive PEG molecule (or a similar reactive water-soluble polymer). As used herein, the term "polyethylene glycol" is intended to encompass any form of PEG which has been used to derivatize other proteins, such as mono (C1-C10) alkoxy- or aryloxy polyethylene glycol or polyethylene glycol-maleimide. In certain embodiments, the antibody to be PEGylated is an aglycosylated antibody. Methods for PEGylation of proteins are known in the art and can be applied to the antibody of the invention, see for example EP 0154316 and EP 0401384.

In certain embodiments, one or more amino acid modifications can be introduced into an Fc region of an antibody provided herein, thereby producing an Fc region variant such that, for example, the efficacy of the antibody in treating cancer or a cell proliferative disease is enhanced. The anti-PD-L1 antibody (e.g., humanized or chimeric antibody) and the antigen-binding fragment thereof disclosed herein also include antibodies and fragments having modified (or closed) Fc regions to provide altered effector functions. See, e.g., U.S. Pat. No. 5,624,821, WO2003/086310, WO2005/120571, WO2006/0057702. Such modifications can be used to enhance or suppress various responses of the immune system and may have beneficial effects in diagnosis and treatment. Modifications of the Fc region include amino acid alternation (substitution, deletions and insertion), glycosylation or deglycosylation, and addition of multiple Fc. Modifications to Fc can also alter the half-life of the antibody in the therapeutic antibodies, thereby enabling less frequent administrations, and thus increased convenience and reduced material use. See Presta (2005) J. Allergy Clin. Immunol. 116:731, pages 734-735.

In one embodiment, the number of cysteine residues of an antibody can be altered to modify antibody properties. For example, the hinge region of CH1 is modified to change (e.g., increase or decrease) the number of cysteine residues in the hinge region. This method is further described in U.S. Pat. No. 5,677,425. The number of cysteine residues in the hinge region of CH1 can be changed to, e.g., facilitate assembly of the light and heavy chains, or increase or decrease the stability of the antibody.

In certain embodiments, the antibodies provided herein can be further modified to contain other non-protein portions known in the art and readily available. Suitable portions for antibody derivatization include, but are not limited to, water-soluble polymers. Non-limiting examples of water-soluble polymers include, but are not limited to, polyethylene glycol (PEG), ethylene glycol/propylene glycol copolymers, carboxymethyl cellulose, dextran, polyvinyl alcohol, polyvinylpyrrolidone, poly-1,3-dioxane, poly-1,3, 6-trioxane, ethylene/maleic anhydride copolymer, polyamino acid (homopolymer or random copolymer), and dextran or poly(n-ethylene methylpyrrolidone) polyethylene glycol, propylene glycol homopolymer, polypropylene oxide/ethylene oxide copolymer, polyoxyethylated polyol (such as glycerol), polyvinyl alcohol, and mixtures thereof. The polymer may have any molecular weight and may be branched or unbranched. The number of polymers attached to the antibody can vary, and if more than one polymer is attached, they can be the same or different molecules. In general, the number and/or type of polymers used for derivatization can be determined based on considerations including, but not limited to, the specific characteristics or functions of the antibody to be improved, whether the antibody derivative will be used in therapy in defined conditions, etc.

In some embodiments, the invention encompasses fragments of the anti-PD-L1 antibodies. Examples of antibody fragments include but are not limited to Fv, Fab, Fab', Fab'-SH, F(ab')$_2$, diabodies, linear antibodies, single chain antibodies (e.g., scFv), single domain antibodies, and bispecific antibodies formed from the antibody fragments.

For example, the antibody molecule may comprise a heavy chain (HC) variable domain sequence and a light chain (LC) variable domain sequence. In one embodiment, the antibody molecule (referred to herein as an incomplete antibody) comprises or consists of a heavy chain and a light chain. In another example, the antibody molecule contains two heavy chain variable domain sequences and two light chain variable domain sequences, thereby forming two antigen-binding sites. Such as Fab, Fab', F(ab')$_2$, Fc, Fd, Fd', Fv, single chain antibodies (e.g., scFv), single domain antibodies, diabody (Dab) (bivalent and bispecific) and chimeric (e.g., humanized) antibodies, which can be produced by modifying intact antibodies, or de novo synthesized using recombinant DNA technology. These functional antibody fragments retain the ability to selectively bind to their corresponding antigens or receptors. Antibodies and antibody fragments can be from any antibody class, including but not limited to, IgG, IgA, IgM, IgD, and IgE, and from any antibody subclass (e.g., IgG1, IgG2, IgG3, and IgG4). The preparation of antibody molecules can be monoclonal or polyclonal. The antibody may be a human antibody, a humanized antibody, a chimeric antibody, a CDR-grafted antibody, or an antibody produced in vitro. The antibody may have, e.g., a heavy chain constant region selected from IgG1, IgG2, IgG3, or IgG4. The antibody may also have a light chain selected from, e.g., kappa or lambda.

The antibody of the invention may also be a single-domain antibody. The single-domain antibody can include antibody whose complementary determining regions are part of a single-domain polypeptide. Examples include, but are not limited to, heavy chain antibodies, antibodies naturally devoid of light chains, single-domain antibodies or engineered antibodies derived from conventional 4-chain antibody. The single-domain antibody can be any antibody of the prior art, or any single-domain antibody in the future. The single-domain antibody can be derived from any species, including but not limited to, mouse, human, camel, alpaca, fish, shark, goat, rabbit, and cattle. According to another aspect of the invention, the single-domain antibody is a naturally occurring single domain-antibody, which is referred to as a heavy chain antibody devoid of light chains. Such single-domain antibodies are disclosed, e.g., in WO94/04678. A single domain antibody or nanobody can be an antibody produced from camelidae species, such as camel, alpaca, dromedary, llama, and guanaco. Species other than camel can produce heavy chain antibodies naturally devoid of light chains; such single domain antibodies are within the scope of the invention.

In some embodiments, the anti-PD-L1 antibody of the invention is a humanized antibody. Different methods for humanizing antibodies are known to those skilled, as summarized by Almagro & Fransson, the contents of which are fully incorporated herein by reference [Almagro J. C. and Fransson J (2008) Frontiers in Bioscience 13:1619-1633]. Almagro & Fransson distinguishes between rational approach and empirical approach. The rational approach is characterized by generating a small number of engineered antibody variants and assessing their binding or any other characteristics of interest. If variants of the design does not produce the expected results, a new round of design and integration evaluation starts. The rational approach includes CDR grafting, resurfacing, superhumanization, and human string content optimization. In contrast, the empirical method is based on generating large humanized variant libraries, and selects the best clones using enrichment techniques or high-throughput screening. Thus, the empirical approach depends on a reliable selection and/or screening system capable of searching a large number of antibody variants. In vitro display technologies such as phage display and ribosome display meet these requirements and are well known to those skilled. The Empirical approach includes FR library construction, guided selection, framework-shuffling, and humaneering.

In some embodiments, the anti-PD-L1 antibody is a human antibody. The human antibody can be prepared through a variety of techniques known in the art. The human antibody is generally described in van Dijk and van de Winkel, Curr. Opin. Pharmacol 5:368-74(2001) and Lonberg, Curr. Opin. Immunol 20:450-459(2008). For example, a transgenic mouse carrying human immunoglobulin genes rather than a mouse system can be used for producing human monoclonal antibodies (see, e.g., Wood et al., International Application WO 91/00906; Kucherlapati et al., PCT Publication WO 91/10741; Lonberg et al., International Application WO 92/03918; Kay et al., International Application 92/03917; Lonberg, N. et al., 1994 Nature 368:856-859; Green, L. L. et al., 1994 Nature Genet. 7:13-21; Morrison, S. L. et al., 1994 Proc. Natl. Acad. Sci. USA 81:6851-6855; Bruggeman et al., 1993 Yeast Immunol 7:33-40; Tuaillon et al., 1993 PNAS 90:3720-3724; and Bruggeman et al., 1991 Eur J Immunol 21:1323-1326).

In some embodiments, the anti-PD-L1 antibody of the invention is a non-human antibody, such as a rodent (mouse or rat) antibody, a goat antibody, a primate (e.g., monkey) antibody and a camelid antibody. Preferably, the non-human antibody is a rodent (mouse or rat) antibody. A method for producing the rodent antibody is known in the art.

In some embodiments, the antibody of the invention is a chimeric antibody. Some chimeric antibodies are described in, for example, U.S. Pat. No. 4,816,567; and Morrison et al., Proc. Natl. Acad. Sci. USA. 81:6851-6855, 1984. In one embodiment, the chimeric antibody comprises a non-human variable region (e.g., a variable region derived from mice, rats, hamsters, rabbits or non-human primates such as monkeys) and a human constant region. In another embodiment, the chimeric antibody is a "class-switched" antibody of which the class or subclass has been altered compared to the class or subclass of parent antibody. The chimeric antibody includes antigen-binding fragments thereof.

In certain embodiments, the chimeric antibody is a humanized antibody. Typically, a non-human antibody is humanized to reduce its immunogenicity in human while retaining the specificity and affinity of its parent non-human antibody. In general, the humanized antibody comprises one or more variable domains, wherein, for example, a CDR (or a part thereof) is derived from the non-human antibody and an FR (or a part thereof) is derived from a human antibody sequence. Optionally, the humanized antibody further comprises at least part of the human constant region. In some embodiments, some FR residues in the humanized antibody are replaced by corresponding residues of a non-human antibody (e.g., the antibody from which CDR residues are derived), e.g., to restore or improve the antibody specificity or affinity.

The antibody of the invention can be isolated by screening a combinatorial library for antibodies having desired activities. For example, various methods are known in the art for generating phage display libraries and screening the libraries for the antibodies with desired binding characteristics. The methods are described in, for example, Hoogenboom et al., Methods in Molecular Biology 178:1-37 (compiled by O' Brien et al., Human Press, Totowa. N.J., 2001), and further described in, for example. McCafferty et al., Nature 348: 552-554; Clackso et al., Nature 352:624-628 (1991); Marks et al., J. Mol. Biol. 222:581-597(1992); Marks and Bradbury, Methods in Molecular Biology 248:161-175 (compiled by Lo, Human Press, Totowa, N.J., 2003); Sidhu et al., J. Mol. Biol. 338(2):299-310(2004); Lee et al., J. Mol. Biol 340(5):1073-1093(2004); Fellouse, Proc. Natl. Acad. Sci. USA 101 (34):12467-12472(2004); and Lee et al., J. Immunol. Methods 284(1-2):119-132(2004).

In one embodiment, the antibody molecule is a monospecific antibody molecule and binds to a single epitope. For example, the monospecific antibody molecule includes a plurality of immunoglobulin variable domain sequences that each binds to the same epitope.

In one embodiment, the antibody molecule is a multispecific antibody molecule, for example, the antibody molecule comprises a plurality of immunoglobulin variable domain sequences, wherein a first immunoglobulin variable domain sequence of the plurality of immunoglobulin variable domain sequences has binding specificity for a first epitope, and a second immunoglobulin variable domain sequence of the plurality of immunoglobulin variable domain sequences has binding specificity for a second epitope. In one embodiment, the first and second epitopes are on the same antigen (e.g., the same protein or the same subunit of a multimeric protein). In one embodiment, the first and second epitopes overlap. In one embodiment, the first and second epitopes do not overlap. In one embodiment, the first and second epitopes are located on different antigens (e.g., different proteins or different subunits of a multimeric protein). In one embodiment, the multispecific antibody molecule comprises a third, fourth or fifth immunoglobulin variable domain. In one embodiment, the multispecific antibody molecule is a bispecific antibody molecule or a trispecific antibody molecule or a tetraspecific antibody molecule.

In one embodiment, the multispecific antibody molecule is a bispecific antibody molecule. A bispecific antibody is specific for no more than two antigens. A bispecific antibody molecule is characterized by a first immunoglobulin variable domain sequence having binding specificity for a first epitope and a second immunoglobulin variable domain sequence having binding specificity for a second epitope. In one embodiment, the first and second epitopes are on the same antigen (e.g., the same protein or the same subunit of a multimeric protein). In one embodiment, the first and second epitopes overlap. In one embodiment, the first and second epitopes do not overlap. In one embodiment, the first and second epitopes are located on different antigens (e.g., different proteins or different subunits of a multimeric protein). In one embodiment, a bispecific antibody molecule comprises heavy and light chain variable domain sequences having binding specificity for a first epitope, and heavy and light chain variable domain sequences having binding specificity for a second epitope. In one embodiment, a bispecific antibody molecule comprises an incomplete antibody having binding specificity for a first epitope, and an incomplete antibody having binding specificity for a second epitope. In one embodiment, a bispecific antibody molecule comprises an incomplete antibody or a fragment thereof having binding specificity for a first epitope, and an incomplete antibody or a fragment thereof having binding specificity for a second epitope. In one embodiment, the bispecific antibody molecule comprises a scFv or a fragment thereof having binding specificity for a first epitope, and a scFv or a fragment thereof having binding specificity for a second epitope. In one embodiment, the first epitope is on PD-L1 and the second epitope is on LAG-3, OX40, TIM-3, CEACAM (e.g., CEACAM-1 and/or CEACAM-5), or PD-L2.

In some embodiments, the invention further provides an anti-PD-L1 monoclonal antibody ("an immunoconjugate") conjugated to other substances, e.g., a therapeutic moiety or marker, such as a cytotoxic agent or an immunomodulator. The cytotoxic agent includes any agent that is harmful to cells. Examples of cytotoxic agent (e.g. a chemotherapeutic agent) suitable for forming the immunoconjugate are known in the art, see e.g. WO2015/153513 or WO2015/138920 or the like. For example, the cytotoxic agent includes, but is not limited to, radioisotopes, e.g., iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99m}$Tc), phosphorus ($^{32}$P), rhodium ($^{188}$Rh), sulfur ($^{35}$S), carbon ($^{14}$C), tritium ($^3$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Examples of cytotoxic agents further include chemotherapeutic agents or other therapeutic substance, e.g., paclitaxel, cytochalasin B, gramicidin D, ethidium bromide, emetine, mitomycin, etoposide, teniposide, vincristine, vinblastine, colchicine, doxorubicin, daunomycin, dihydroxyanthracine diketone, mitoxantrone, mithramycin, actinomycin D, 1-dihydrotestosterone, glucocorticoids, procaine, tetracaine, lidocaine, propranolol, and puromycin and analogs or homologs of all above therapeutic agents. Cytotoxic agents further include, for example, antimetabolites (e.g., methotrexate, 6-mercaptopurine, 6-thioguanine, cytarabine, 5-fluorouracil, and dacarbazine), alkylating agents (e.g., mechlorethamine, thioephaloramucil, melphalan, carmustine (BSNU), lomustine (CCNU), cyclophosphamide, busulfan, dibromomannitol, streptozotocin, mitomycin C, and cis-dichlorodiammineplatinum (II) (DDP) cisplatin), anthramycins (e.g., daunorubicin (formerly known as daunomycin) and doxorubicin), antibiotics (e.g., actinomycin D (formerly known as actinomycin), bleomycin, mithramycin, and anthramycin (AMC)), and antimitotics (e.g., vincristine and vinblastine).

Substances that can be conjugated/coupled to anti-PD-L1 antibody can be seen in, for example, WO2010/077634 or U.S. 60/696,426 or WO2016/007235 or WO2016/061142 or the like.

Nucleic Acid of the Invention and Host Cell Comprising Same

In one aspect, the invention provides a nucleic acid encoding any of the above anti-PD-L1 antibodies or fragments thereof. The nucleic acid can encode an amino acid sequence comprising the light chain variable region and/or the heavy chain variable region of the antibody, or an amino acid sequence comprising the light chain and/or the heavy chain of the antibody.

For example, an exemplary nucleic acid of the invention includes a nucleic acid encoding an amino acid sequence selected from any one of SEQ ID NOs: 26 to 51, or a nucleic acid encoding an amino acid sequence having at least 85%, 90%, 91%, 92%, 93%, 94%, 95%, 96%, 97%, 98%, or 99% identity to an amino acid sequence selected from any one of SEQ ID NOs: 26 to 51.

The invention further provides a nucleic acid that is hybridized under a stringent condition with the following nucleic acid or a variation of the following nucleic acid having one or more substitutions (e.g., conservative substitutions), deletions or insertions: a nucleic acid encoding an amino acid sequence selected from any one of SEQ ID NOs: 26 to 51; or a nucleic acid encoding an amino acid sequence having at least 85%, 90%, 91%, 92%, 93%, 94%, 95%, 96%, 97%, 98%, or 99% identity to an amino acid sequence selected from any one of SEQ ID NOs: 26 to 51.

In one embodiment, one or more vectors containing the nucleic acid are provided. In one embodiment, the vector is an expression vector, such as an eukaryotic expression vector. The vector includes, but is not limited to, a virus, a plasmid, a cosmid, a lambda phage or a yeast artificial chromosome (YAC). Numerous vector systems can be used. For example, one class of vectors utilizes DNA elements derived from animal viruses such as bovine papillomaviruses, polyomaviruses, adenoviruses, vaccinia virus, baculoviruses, retroviruses (Rous sarcoma virus or MMTV or MOMLV) and SV40 virus. Another class of vectors utilizes RNA elements derived from RNA viruses such as Semliki Forest virus, eastern equine encephalitis virus and flaviviruses. In a preferred embodiment, the expression vector of the present invention is a pTT5 expression vector.

Additionally, cells having stably incorporated DNA in chromosomes thereof can be selected by introducing one or more markers permitting the selection of transfected host cells. The markers may, for example, provide prototrophy, biocidal (e.g., antibiotics) resistance, or heavy metal (e.g., copper) resistance, etc., for an auxotrophic host. Selectable marker genes may be linked directly to a DNA sequence to be expressed or introduced through co-transformation into the same cell. Additional elements may also be required for optimal synthesis of mRNA. The elements may include splicing signals, transcriptional promoters, enhancers, and termination signals.

Once the expression vector or DNA sequence has been prepared for expression, the expression vector can be transfected or introduced into suitable host cells. Various techniques can be used for this purpose, for example, protoplast fusion, calcium phosphate precipitation, electroporation, retroviral transduction, viral transfection, biolistics, lipid-based transfection, or other conventional techniques. In the case of protoplast fusion, cells are incubated in a culture medium and screened for appropriate activity. Methods and conditions for incubating the resulting transfected cell and for recovering the resulting antibody molecules are known to those skilled in the art and may be varied or optimized according to the particular expression vector and the particular mammalian host cell used based on the present description and methods known in the art.

In one embodiment, a host cell containing a nucleic acid encoding the antibody molecule described herein or the vector described herein is provided. Suitable host cells for cloning or expressing the nucleic acid encoding the antibody or the vector include prokaryotic or eukaryotic cells as described herein. The antibody can be produced, for example, in bacteria, particularly when glycosylation and Fc effector functions are not required. Expression of an antibody fragment and a polypeptide in bacteria is described in, for example, U.S. Pat. Nos. 5,648,237, 5,789,199 and 5,840,523, and also described in Charlton, Methods in Molecular Biology, Vol. 248 (B. K. C. Lo, ed., Humana Press, Totowa, N.J., 2003), pg. 245-254, which describes expression of antibody fragments in *E. coli*. After expression, the antibody can be isolated from bacterial paste in soluble fraction and can be further purified. In one embodiment, the host cell is *E. coli*.

In one embodiment, the host cell is eukaryotic. In another embodiment, the host cell is selected from the group consisting of yeasts, mammalian cells (e.g., a human cell), insect cells, plant cells, or other cells suitable for preparation of an antibody or an antigen-binding fragment thereof. For example, eukaryotic microorganisms such as filamentous fungi or yeast are suitable cloning or expression hosts for the vector encoding the antibody, including fungus and yeast strains in which a glycosylation pathway has been "humanized" resulting in production of an antibody having a partially or fully human glycosylation pattern, referring to Gerngross, Nat. Biotech. 22: 1409-1414(2004), and Nat. Biotech. 24:210-215 (2006). Host cells suitable for expressing a glycosylated antibody are also derived from multicellular organisms (invertebrates and vertebrates).

Vertebrate cells may also be used as host. For example, a mammalian cell line engineered to be suitable for suspension growth may be used. Other examples of useful mammalian host cell lines are monkey kidney CV1 lines (COS-7) transformed with SV40, human embryonic kidney lines (293HEK or 293 cells, as described in, e.g., Graham et al., J. Gen Virol. 36: 59 (1977)) and the like. Other useful mammalian host cell lines include Chinese hamster ovary (CHO) cells including DHFR$^-$ CHO cells (Urlaub et al., Proc. Natl. Acad. Sci. USA 77: 216 (1980)), and myeloma cell lines such as Y0, NS0, and Sp2/0.

Reviews of certain mammalian host cell lines suitable for antibody production can be seen from, e.g., Yazaki and Wu, Methods in Molecular Biology, Vol. 248 (B. K. C. Lo, ed., Humana Press, Totowa, N.J.), pg. 255-268 (2003). Other useful host cells include, but are not limited to, Vero cells, Hela cells, COS cells. CHO cells. HEK293 cells, BHK cells, MDCKII cells, oocytes from PerC6 cell lines (e.g., PERC6 cells from Crucell), and cells from transgenic animals, such as mammary epithelial cells. Suitable insect cells include, but are not limited to, Sf9 cells.

Method for Preparing Antibody and Antigen-Binding Fragment Thereof

The anti-PD-L1 antibody disclosed herein can be recombinantly produced. There are several methods known in the art for the production of recombinant antibodies. An example of methods for recombinant production of antibodies is disclosed in U.S. Pat. No. 4,816,567.

In one embodiment, a method for preparing an anti-PD-L1 antibody is provided, wherein the method comprises steps of incubating host cells containing an nucleic acid encoding the antibody, as provided above, under conditions suitable for expressing antibodies, and optionally, recovering the antibody from the host cells (or the host cell cultures). For recombinant production of the anti-PD-L1 antibody, a nucleic acids encoding the antibody (e.g., the antibody described above) is isolated and inserted into one or more vectors for further cloning and/or expression in the host cells. The nucleic acid is readily isolated and sequenced by using conventional procedures (e.g., by using oligonucleotide probes that are capable of binding specifically to genes encoding heavy and light chains of antibodies).

In one embodiment, the host cell contains a vector including a nucleic acid encoding an amino acid sequence of a VL of the antibody and a nucleic acid encoding an amino acid sequence of a VH of the antibody. In one embodiment, the host cell contains a first vector comprising a nucleic acid encoding an amino acid sequence of a VL of the antibody and a second vector comprising a nucleic acid encoding an amino acid sequence of a VH of the antibody.

Assay

The anti-PD-L1 antibody provided herein can be identified, screened, or characterized for its physical/chemical properties and/or biological activity through a variety of assays known in the art. In one aspect, the antigen-binding activity of the antibody of the invention is tested, for example, by known methods such as ELISA, Western blotting, flow cytometry, and magnetic beads coated with antibody molecules. PD-L1 binding can be determined by methods known in the art, and exemplary methods are disclosed herein. In some embodiments, a biological optical interferometry (e.g., Fortebio affinity measurement) or MSD assay or flow cytometry is used.

In another aspect, a competitive binding assay can be used for identifying an antibody that competes for binding to PD-L1 with any of the anti-PD-L1 antibodies disclosed herein. In some embodiments, such competitive antibodies bind to the same epitope (e.g., a linear or conformational epitope) as any of the anti-PD-L1 antibodies disclosed herein. A detailed exemplary method for locating an antibody binding epitope is described in Morris (1996) "Epitope Mapping Protocols", Methods in Molecular Biology vol. 66 (Humana Press, Totowa, N.J.).

The invention further provides an assay for identifying an anti-PD-L1 antibody having one or more of the properties described above. Further provided is an antibody having such biological activities in vivo and/or in vitro.

In some embodiments, the antibody of the invention is tested for one or more of the properties described above.

Cells for use in any of said in-vitro assays include cells or cell lines that naturally express PD-L1 or that are engineered to express PD-L1.

It will be appreciated that any of said assays can be performed by using the immunoconjugate of the invention in place of or in addition to the anti-PD-L1 antibody.

It will be appreciated that any of said assays can be performed by using the anti-PD-L1 antibody and other therapeutic agents.

Pharmaceutical Composition and Pharmaceutical Preparation

The invention further provides a composition (including a pharmaceutical composition or a pharmaceutical preparation) comprising an anti-PD-L1 antibody or a fragment of the antibody or a immunoconjugate thereof, and a composition comprising the nucleic acid encoding the anti-PD-L1 antibody or the fragment thereof. In certain embodiments, the compositions comprise one or more antibodies that bind to PD-L1 or fragments of the antibodies or immunoconjugates thereof, or one or more nucleic acids encoding the one or more antibodies that bind PD-L1 or the fragments thereof. Such compositions may further contain suitable pharmaceutical supplementary materials such as a pharmaceutical carrier, an excipient, and the like known in the art, including buffers.

The pharmaceutical carrier suitable for use in the invention can be sterile liquid, such as water and oil, including petroleum, or oil of animal, vegetable, or synthetic source, e.g., peanut oil, soybean oil, mineral oil, sesame oil, and the like. Water is a preferred carrier when the pharmaceutical composition is administered intravenously. Saline solutions and aqueous dextrose and glycerol solutions can also be employed as liquid carriers, particularly used for injectable solutions.

Suitable excipients includes starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. For uses of excipients, see "Handbook of Pharmaceutical Excipients", the fifth edition, R. C. Rowe, P. J. Seskey and S. C. Owen. Pharmaceutical Press, London, Chicago.

The composition may further contain a small quantity of wetting agent or emulsifier, or pH buffer, if desired.

The compositions may take the form of a solution, a suspension, an emulsion, a tablet, a pill, a capsule, a powder, a sustained release preparation, and the like. Oral preparations may contain standard carriers and/or excipients such as pharmaceutical-grade mannitol, lactose, starch, magnesium stearate and saccharin.

The pharmaceutical preparation, preferably in the form of a lyophilized preparation or an aqueous solution, comprising the anti-PD-L1 antibody described herein can be prepared by mixing the anti-PD-L1 antibody of desired purity with one or more optional pharmaceutical supplementary materials [Remington's Pharmaceutical Sciences, the 16th edition, Osol. A. ed. (1980)].

An exemplary lyophilized antibody preparation is described in U.S. Pat. No. 6,267,958. The aqueous antibody preparation includes those described in U.S. Pat. No. 6,171,586 and WO2006/044908, and the latter preparation comprises a histidine-acetate buffer.

The pharmaceutical composition or preparation of the invention may also contain more than one active ingredient required by a treated particular indication, preferably active ingredients having complementary activities without adversely affecting one another. For example, it is desirable to further provide other anti-cancer active ingredients, such as a chemotherapeutic agent and/or a cytotoxic agent. The active ingredients are suitably combined in an amount effective for an intended purpose. The active ingredients may be any substance known in the art and capable of being combined with an anti-PD-L1 antibody, including chemotherapeutic agents, other antibodies, and other therapeutic agents. Examples of the active ingredients can be seen in, for example, WO2010/077634, WO2016/061142, U.S. 61/264,061, U.S. 60/696,426, WO2016/007235, and the like.

In some embodiments, the active ingredient is an anti-LAG-3 antibody, e.g., an anti-LAG-3 antibody that binds to a human antigen, preferably, the anti-LAG-3 antibody is humanized.

A sustained release preparation can be prepared. Suitable examples of the sustained release preparation include a semipermeable matrix of a solid hydrophobic polymer containing an antibody, the matrix is in the form of a shaped article, e.g., a film or a microcapsule.

Use of Antibody

In one aspect, the invention relates to a method for modulating an immune response in a subject. The method comprises administering to the subject an effective amount of the antibody molecule (e.g., the anti-PD-L1 antibody) or the pharmaceutical composition or the immunoconjugate disclosed herein, thereby modulating the immune response in the subject. In one embodiment, the antibody molecule (e.g., a therapeutically effective amount of the anti-PD-L1 antibody molecule) or the pharmaceutical composition or the immunoconjugate disclosed herein restores, enhances, stimulates or increases the immune response in the subject.

In another aspect, the invention relates to a method for preventing or treating a tumor (e.g., cancer) in a subject, wherein the method comprises administering to the subject an effective amount of the antibody molecule (e.g., the anti-PD-L1 antibody) or the pharmaceutical composition or the immunoconjugate disclosed herein. In some embodiments, the tumor is a tumor immune escape. Preferably, the tumor is a gastrointestinal tumor (e.g., cancer), such as colon cancer.

In another aspect, the invention relates to a method for preventing or treating an infectious disease in a subject, wherein the method comprises administering to the subject an effective amount of the antibody molecule (e.g., the anti-PD-L1 antibody) or the pharmaceutical composition or the immunoconjugate disclosed herein. In one embodiment, the infectious disease is a chronic infection.

In another aspect, the invention relates to a method for inducing antibody-dependent cell-mediated cytotoxicity in the subject, and the method comprises administering to the subject an effective amount of the antibody molecule (e.g., the anti-PD-L1 antibody) or the pharmaceutical composition or the immunoconjugate disclosed herein.

The subject can be a mammal, e.g., a primate, preferably a higher primate, e.g., a human (e.g., a patient having or at risk of having the disease described herein). In one embodiment, the subject is in need of an enhanced immune response. In some embodiments, the anti-PD-L1 antibody molecule described herein promotes T cell proliferation. In some embodiments, the anti-PD-L1 antibody molecule described herein restores, enhances or stimulates an antigen-specific T cell response in the subject, e.g., interleukin-2 (IL-2) or interferon-gamma (IFN-gamma) production in the antigen-specific T cell response. In some embodiments, the immune response is an anti-tumor response. In one embodiment, the subject has or is at risk of having the disease described herein (e.g., the tumor or infectious disease as described herein). In certain embodiments, the subject is immunocompromised or at risk of immunocompromising. For example, the subject receives or has received chemotherapy and/or radiation therapy. Alternatively or in combination, the subject is immunocompromised due to infection or is at risk of being immunocompromised due to infection.

In some embodiments, the tumor, e.g., cancer, described herein includes, but is not limited to, a solid tumor, a hematological cancer, a soft tissue tumor, and a metastatic lesion.

Examples of the solid tumor include a malignant tumor, e.g., sarcomas and carcinomas (including adenocarcinomas and squamous cell carcinomas) of various organ systems, such as carcinomas that affect liver, lungs, breasts, lymph, gastrointestinal tract (e.g., the colon), genitourinary tract (e.g., kidney and bladder epithelial cells), prostate, and pharynx. The adenocarcinomas include malignant tumors such as most colon cancers, rectal cancers, renal cell carcinomas, liver cancers, non-small cell carcinomas in lung cancers, small intestine cancers, and esophageal cancers. The squamous cell carcinomas include malignant tumors, such as carcinomas in lungs, esophagus, skin, head and neck regions, oral cavity, anus, and cervix. In one embodiment, the cancer is melanoma, e.g., advanced melanomas. In one embodiment, the cancer is gastrointestinal cancer, such as the colon cancer. Metastatic lesions of the aforementioned carcinomas can also be treated or prevented by using the method and composition of the invention.

Non-limiting examples of preferred cancers to be treated include lymphoma (e.g., diffuse large B-cell lymphoma, Hodgkin's lymphoma and non-Hodgkin's lymphoma), breast cancer (e.g., metastatic breast cancer), lung cancer (e.g., non-small cell lung cancer (NSCLC), e.g., stage IV or recurrent non-small cell lung cancer, NSCLC adenocarcinoma, or NSCLC squamous cell carcinoma), myelomas (e.g., multiple myelomas), leukemias (e.g., chronic myelogenous leukemias), skin cancer (e.g., melanomas (e.g., stage III or IV melanoma) or Merkel cell carcinoma), head and neck cancers (e.g., head and neck squamous cell carcinomas (HNSCC)), myelodysplastic syndromes, bladder cancers (e.g., transitional cell carcinomas), kidney cancers (e.g., renal cell carcinomas, e.g., clear cell renal cell carcinoma, and e.g., advanced or metastatic clear cell renal cell carcinoma), and colon cancer. In addition, refractory or recurrent malignancies can be treated by using the antibody molecule described herein.

Examples of other cancers that may be treated include osteocarcinoma, pancreatic cancer, skin cancer, hear or neck cancer, cutaneous or intraocular melanomas, uterine cancer, ovarian cancer, rectal cancer, anal cancer, gastro-esophageal cancer, gastric cancer, testicular cancer, uterine cancer, fallopian tube cancer, endometrial cancer, cervical cancer, vaginal cancer, vulval cancer, Merkel cell carcinoma, Hodgkin's lymphoma, non-Hodgkin's lymphoma, esophageal cancer, small intestine cancer, endocrine carcinoma, thyroid cancer, parathyroid cancer, adrenal carcinoma, soft tissue sarcoma, urethral carcinoma, penis carcinoma, chronic or acute leukemia (including acute myeloid leukemia, chronic myeloid leukemia, acute lymphoblastic leukemia, and chronic lymphocytic leukemia), pediatric solid tumors, lymphocytic lymphoma, bladder cancer, multiple myeloma, myelodysplastic syndromes, renal or ureteral cancer, renal pelvis cancer, central nervous system (CNS) tumors, primary CNS lymphoma, tumor angiogenesis, epistropheus tumors, brainstem glioma, pituitary adenoma. Kaposi's sarcoma, epidermoid carcinoma, squamous-cell carcinoma, T cell lymphoma, and environmentally induced cancers (including cancers induced by asbestos, e.g., mesothelioma), and combinations thereof.

Treatment of metastatic cancer, for example, metastatic cancer expressing PD-L1 (Iwai et al., (2005) Int. Immunol. 17:133-144), can be implemented by using the antibody molecule described herein.

Tumor immune escape may also be treated by using the antibody molecule described herein.

In one embodiment, the tumor is a cancer that expresses elevated levels of PD-L1.

In some embodiments, the cancer described herein is colon cancer and metastatic cancer thereof.

In some embodiments, the infection is acute or chronic. In some embodiments, the chronic infection is a persistent infection, a latent infection or a slow infection. In some embodiments, the chronic infection is caused by a pathogen selected from the group consisting of bacteria, viruses, fungi, and protozoa.

In some embodiments, the pathogen is a bacterium. In one embodiment, the bacterium is selected from the group consisting of *Mycobacterium* species (*Mycobacterium* spp.). *Salmonella* species (*Salmonella* spp.), *Listeria* species (*Listeria* spp.), *Streptococcus* species (*Streptococcus* spp.), *Haemophilus* species (*Haemophilus* spp.), *Neisseria* species (*Neisseria* spp.), *Klebsiella* species (*Klebsiella* spp.), *Borrelia* species (*Borrelia* spp.), *Bacterioides fragilis*, *Treponema* species (*Treponema* spp.), and *Helicobacter pylori*.

In some embodiments, the pathogen is a virus. In one embodiment, the virus is selected from the group consisting of infectious viruses, for example, hepatitis B virus or hepatitis C virus (HBV or HCV), herpes simplex virus I or II, human immunodeficiency virus I or II, cytomegavirus, epstein barr virus (EBV), human papillomavirus, human T lymphotropic leukemia virus I or II, and varicella zoster.

In some embodiments, the pathogen is a fungus. In one embodiment, a fungal-induced disorder is selected from the group consisting of aspergilosis, blastomycosis, candidiasis *albicans*, coccidioiodmycosis *immitis*, histoplasmosis, paracoccidioiomycosis, and microsporidiosis.

In some embodiments, the pathogen is a protozoon such as a parasite. In one embodiment, the disorder caused by the protist is selected from the group consisting of leishmaniasis, plasmodiosis (i.e., malaria), cryptosporidiosis, toxoplasmosis, trypanosomiasis and helminth infection, including diseases caused by trematodes (e.g., schistosomiasis), cestodes (e.g., echinococcosis) and nematodes (e.g., trichinosis), ascariasis, filariasis and strongyloidosis.

In another embodiment, the infection is a hepatitis infection. e.g., a hepatitis B or hepatitis C infection. The anti-PD-L1 antibody molecule may be combined with conventional treatments for hepatitis B infection or hepatitis C infection for therapeutic advantages. In certain embodiments, the anti-PD-L1 antibody molecule is administered in combination with a hepatitis B antigen (e.g., Engerix B) or vaccine, and optionally in combination with an aluminum-containing adjuvant.

In another embodiment, the infectious disease is influenza. In certain embodiments, the anti-PD-L1 antibody molecule is administered in combination with an influenza antigen or vaccine.

Diseases suitable for prevention or treatment with the anti-PD-L1 antibody or the fragment thereof of the invention can be further seen in WO2010/077634, WO2016/061142, U.S. 60/696,426, WO2016/007235 or U.S. 61/264,061.

In other aspects, the invention provides uses of the anti-PD-L1 antibody or the fragment thereof or the immunoconjugate thereof in manufacture or preparation of a drug for prevention or treatment of the above-mentioned related diseases or conditions.

In some embodiments, the antibody or the antibody fragment or the immunoconjugate of the invention delays the onset of the conditions and/or symptoms associated with the conditions.

Combination Therapy

In some embodiments, the prevention or treatment method described herein further comprises administering to the subject or individual the antibody molecule (e.g., the anti-PD-L1 antibody or the fragment thereof) or the pharmaceutical composition or the immunoconjugate disclosed herein in combination with one or more other therapies, e.g., therapeutic modalities and/or other therapeutic agents.

In some embodiments, the therapeutic modality includes surgery (e.g., tumor resection), a radiation therapy (e.g., an external beam therapy that involves a three-dimensional conformal radiation therapy in which an irradiation region is designed), partial irradiation (e.g., irradiation directed to a preselected target or organ), focused irradiation, and the like. The focused irradiation may be selected from the group consisting of stereotactic radiosurgery, fractionated stereotactic radiosurgery, and intensity-modulated radiotherapy. The focused irradiation may have a radiation source selected from the group consisting of particle beams (protons), cobalt-60 (photons), and linear accelerators (X-rays), for example, as described in WO 2012/177624.

The radiation therapy can be conducted through one or combination of methods including, but not limited to, external beam therapy, internal radiation therapy, implant irradiation, stereotactic radiosurgery, systemic radiotherapy, radiotherapy and permanent or transient interstitial brachytherapy. The term "brachytherapy" refers to radiation therapy delivered by a spatially confined radioactive substance inserted into the body at or near the sites of tumors or other proliferative tissue diseases. The term is intended to include but not be limited to exposure to radioisotopes (e.g., At-211, I-131, 1-125, Y-90, Re-186, Re-188, Sm-153, Bi-212, P-32, and radioactive isotopes of Lu). Suitable radiation sources includes solids and liquids. Through non-limiting examples, the radiation source may be a radionuclide, such as I-125, I-131, Yb-169 and Ir-192 as a solid source, I-125 as a solid source, or other radionuclides that emit photons, beta particles, gamma radiation or other therapeutic rays. The radioactive substance may also be a fluid made from any radionuclide solution, for example, an I-125 or I-131 solution, or a radioactive fluid can be produced by using a slurry of a suitable fluid containing small particles of a solid radionuclide (e.g., Au-198 and Y-90). In addition, the radionuclide may be contained in gel or radioactive microspheres.

In some embodiments, the therapeutic agent is selected from the group consisting of chemotherapeutic agents, cytotoxic agents, vaccines, other antibodies, anti-infective active agents, and immunomodulators (e.g., co-stimulatory molecule activators or immune checkpoint molecule inhibitors).

Exemplary cytotoxic agents include anti-microtubule drugs, topoisomerase inhibitors, antimetabolites, mitotic inhibitors, alkylating agents, anthracyclines, *vinca* alkaloids, intercalating agents, active agents capable of interfering with signal transduction pathways, active apoptotic agents, proteasome inhibitors, and irradiation (e.g., partial or total body irradiation (e.g., gamma radiation)).

Other exemplary antibodies include, but are not limited to, immune checkpoint inhibitors (e.g., anti-CTLA-4, anti-TIM-3, anti-CEACAM or anti-LAG-3), antibodies (e.g., agonistic GITR antibodies or CD137 antibodies) that stimulate immune cells, anti-cancer antibodies (e.g., rituximab (Rituxan® or MabThera®), trastuzumab (Herceptin®), tositumomab (Bexxar®), ibritumomab (Zevalin®), alemtuzumab (Campath®), epratuzumab (Lymphocide®), bevacizumab (Avastin®), erlotinib (Tarceva®), cetuximab (Erbitux®), and the like.

Exemplary chemotherapeutic agents include, but are not limited to, anastrozole (Arimitex®), bicalutamide (Casodex®), bleomycin sulfate (Blenoxane®), busulfan (Myleran®), busulfan injection (Busulfex®), capecitabine (Xeloda®), N4-pentyloxycarbonyl-5-deoxy-5-fluorocytidine, carboplatin (Parapalatin®), carmustine (BiCNU®), chlorambucil (Leukeran®), cisplatin (Platinol®), cladribine (Leustatin®), cyclophosphamide (Cytoxan® or Neosar®), cytosine arabinoside, cytosine arabinoside (Cytosar-U®), depocyt (DepoCyt®), dacarbazine (DTIC-Dome®), dactinomycin (actinomycin D and Cosmegan), daunomycin hydrochloride (Cerubidine®), daunomycin citrate liposome injection (DaunoXome®), dexamethasone, docetaxel (Taxotere®), doxorubicin hydrochloride (Adriamycin® and Rubex®), etoposide (Vepesid®), fludarabine phosphate (Fludara®), 5-fluorouracil (Adrucil® and Efudex®), flutamide (Eulexin®), tezacitibine, gemcitabine (difluorodeoxycytidine), hydroxyurea (Hydrea®), idarubicin (Idamycin®), ifosfamide (IFEX®), irinotecan (Camptosar®), L-asparaginase (ELSPAR®), calcium folinate, melphalan (Alkran®), 6-mercaptopurine (Purinethol®), methotrexate (Folex®), mitoxantrone, gemtwuumab ozogamicin (mylotarg), paclitaxel (Taxol®), phoenix (yttrium 90/MX-DTPA), pentostatin, polifeprosan 20 in combination with carmustine implants (Gliadel®), tamoxifen citrate (Nolvadex®), teniposide (Vumon®), 6-thioguanine, thiotepa, tirapazamine (Tirazoline®), topotecan hydrochloride for injection (Hycamptin®), vinblastine (Velban®), vincristine (Oncovin®), vinorelbine, ibrutinib, Zydelig (idelalisib) and brentuximab vedotin.

Exemplary vaccines include, but are not limited to, cancer vaccines. The vaccine may be a DNA-based vaccine, a RNA-based vaccine or a virus transduction-based vaccine. Cancer vaccines can be prophylactic or therapeutic. In some embodiments, the cancer vaccine is a peptide cancer vaccine which is a personalized peptide vaccine in some embodiments. In some embodiments, the peptide cancer vaccine is multivalent long peptide, multiple peptide, peptide mixture, hybrid peptide, or peptide-pulsed dendritic cell vaccine (see, e.g., Yamada et al., Cancer Sci, 104:14-21, 2013).

Exemplary active anti-infective agents include, but are not limited to, antivirals, antifungals, antiprotozoals and antibacterials, such as nucleoside analogs (zidovudine (AST), ganciclovir, foscamet, or cidovir), as described above.

Immunomodulators include immune checkpoint molecule inhibitors and co-stimulatory molecule activators.

In some embodiments, the immune checkpoint molecule inhibitor is an inhibitor of PD-1, PD-L2, CTLA-4, TIM-3, LAG-3, CEACAM (e.g., CEACAM-1, -3, and/or -5), VISTA, BTLA, TIGIT, LAIR1, CD160, 2B4 and/or TGFR beta. Inhibition of the molecule may occur at DNA, RNA, or protein level. In some embodiments, inhibitory nucleic acids (e.g., dsRNA, siRNA, or shRNA) can be used to inhibit expression of immune checkpoint molecules. In other embodiments, immune checkpoint molecule inhibitors are polypeptides that bind to the immune checkpoint molecule such as a soluble ligand (e.g., PD-1-Ig or CTLA-4Ig), or an antibody or an antigen-binding fragment thereof for example, the antibody or the fragment thereof that binds to PD-1, PD-L2, CEACAM (e.g., CEACAM-1, -3, and/or -5), CTLA-4, TIM-3, LAG-3, VISTA, BTLA, TIGIT, LAIR1, CD160, 2B4, and/or TGFR beta or a combination thereof. In other embodiments, the immunomodulator is an inhibitor of CEACAM (e.g., CEACAM-1, -3 and/or -5) (e.g., human CEACAM (e.g., CEACAM-1, -3 and/or -5)). In other embodiments, the immunomodulator is an inhibitor of LAG-3 (e.g., human LAG-3). In one embodiment, the inhibitor of LAG-3 is an antibody molecule against LAG-3, e.g., an anti-LAG-3 antibody that binds to human, preferably the anti-LAG-3 antibody being humanized. In other embodiments, the immunomodulator is an inhibitor of TIM-3 (e.g., human TIM-3). In one embodiment, the inhibitor of TIM-3 is an antibody molecule against TIM-3.

In some embodiments, the immunomodulator is a co-stimulatory molecule activator or agonist. In one embodiment, the co-stimulatory molecule agonist is an agonist (e.g., an agonistic antibody or an antigen-binding fragment thereof or a soluble fusion) of a molecule selected from the group consisting of OX40, CD2, CD27, CD28, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, or CD83 ligand. In other embodiments, the immunomodulator is a GITR agonist. In one embodiment, the GITR agonist is an antibody molecule against GITR. In other embodiments, the immunomodulator is an OX40 agonist. In one embodiment, the OX40 agonist is an antibody molecule against OX40.

In some further embodiments, the anti-PD-L1 antibody or the fragment thereof can also be used in combination with a tyrosine kinase inhibitor (e.g., a receptor tyrosine kinase (RTK) inhibitor). Exemplary tyrosine kinase inhibitors include, but are not limited to, epidermal growth factor (EGF) pathway inhibitors (e.g., epidermal growth factor receptor (EGFR) inhibitor), vascular endothelial growth factor (VEGF) pathway inhibitors (e.g., vascular endothelial growth factor receptor (VEGFR) inhibitor, for example, VEGFR-1 inhibitor, VEGFR-2 inhibitor, and VEGFR-3 inhibitor), platelet-derived growth factor (PDGF) pathway inhibitors (e.g., platelet-derived growth factor receptor (PDGFR) inhibitor, for example, PDGFR-beta inhibitor), RAF-1 inhibitors, KIT inhibitors, and RET inhibitors.

In some embodiments, the anti-PD-L1 antibody or the fragment thereof of the invention can also be used in combination with a PI3K inhibitor, an mTOR inhibitor, a BRAF inhibitor, an MEK inhibitor, a JAK2 inhibitor, and/or the like.

In some embodiments of any of the methods of the invention, administration of the anti-PD-L1 antibody or the fragment thereof of the invention is combined with administration of an antigen. The antigen may be, for example, a tumor antigen, a viral antigen, a bacterial antigen, or an antigen from a pathogen. In some embodiments, the tumor antigen comprises a protein. In some embodiments, the tumor antigen comprises a nucleic acid. In some embodiments, the tumor antigen is a tumor cell.

In some embodiments, the anti-PD-L1 antibody or the fragment thereof of the invention can be administered in combination with a therapy comprising adoptive transfer of T cells (e.g., cytotoxic T lymphocytes or CTLs) expressing a chimeric antigen receptor (CAR).

In some embodiments, the anti-PD-L1 antibody or the fragment thereof of the invention can be administered in combination with an anti-tumor agent.

In some embodiments, the anti-PD-L1 antibody or the fragment thereof of the invention can be administered in combination with an oncolytic virus. In some embodiments, the oncolytic virus is capable of selectively replicating in cancer cells and triggering cancer cell death or delaying the growth of cancer cells. In some cases, the oncolytic virus has no effect or minimal effect on non-cancer cells. The oncolytic virus includes, but is not limited to, oncolytic adenovirus, oncolytic herpes simplex virus, oncolytic retrovirus, oncolytic parvovirus, oncolytic vaccinia virus, oncolytic sindbis virus, oncolytic influenza virus, or oncolytic RNA virus (e.g., oncolytic reovirus, oncolytic Newcastle disease virus (NDV), oncolytic measles virus, or oncolytic vesicular stomatitis virus (VSV)). In some embodiments, the oncolytic virus is a virus described in US 2010/0178684 A1, for example, a recombinant oncolytic virus.

In some embodiments, the anti-PD-L1 antibody or the fragment thereof of the invention can be administered in combination with a cytokine.

In some embodiments, the antibody or the fragment thereof of the invention can be combined with a conventional cancer therapy in the art including, but not limited to, (i) radiation therapies (e.g., radiation therapy, X-ray therapy and irradiation) or ionizing radiation to kill cancer cells and reduce tumors, wherein the radiation therapy can be conducted through external beam radiation therapy (EBRT) or internal brachytherapy; (ii) chemotherapies, or application of cytotoxic drugs, which generally affect cells that are rapidly dividing; (iii) targeted therapies, or agents (e.g., tyrosine kinase inhibitor such as imatinib and gefitinib; monoclonal antibody; photodynamic therapy) that specifically affect the deregulation of cancer cell proteins; (iv) immunotherapies, or enhanced host immune responses (e.g., vaccine); (v) hormone therapies, or blocking hormones (e.g., when the tumors are sensitive to hormones); (vi) angiogenesis inhibitors, or therapies blocking angiogenesis and growth; and (vii) palliative care, or such therapies that relate to improving the quality of healthcare to manage pain, nausea, vomiting, diarrhea, and bleeding, in which analgesics such as morphine and oxycodone and anti-emetics such as ondansetron and aprepitant are given to allow a more aggressive therapeutic regimen.

In some embodiments, the antibody or the fragment thereof of the invention can be combined with a conventional method enhancing host immune functions. The conventional method includes, but is not limited to: (i) APC enhancement by, for example, (a) injecting a DNA encoding a heterologous MHC alloantigen to a tumor, or (b) transfecting a biopsied tumor cell with a gene that increases the possibility of immune antigen recognition (e.g., immunostimulatory cytokine, GM-CSF, co-stimulatory molecule B7.1, and co-stimulatory molecule B7.2). (ii) adoptive cellular immunotherapy, or activated tumor-specific T cell therapy. The adoptive cell immunotherapy includes isolating tumor-infiltrating host T lymphocytes, and stimulating the expansion of the population in vitro, for example, through IL-2 or tumor or both; in addition, isolated dysfunctional T cells can be activated through in-vitro application of the antibody of the invention, and then the activated T cells can be re-administered to the host.

The various combination therapies described above can be further combined for treatment.

More examples of combinations of the anti-PD-L1 antibody with other therapeutic modalities or therapeutic agents can be found in WO2016/061142, WO2010/077634, U.S. 60/696,426, U.S. 61/264,061, WO2016/007235, or the like.

Such combination therapies encompass both co-administration (wherein two or more therapeutic agents are contained in the same formulation or separate formulations), and separate administration, in which administration of the antibody of the invention can occur prior to, concurrently with, and/or after the administration of other therapies, e.g., therapeutic modalities or therapeutic agents. The antibody molecule and/or other therapies, e.g., therapeutic agents or therapeutic modalities, can be administered during active diseases or in the period of remission or less active diseases. The antibody molecule may be administered prior to other therapies, concurrently with other therapies, after other therapies, or during remission of diseases.

In one embodiment, administration of the anti-PD-L1 antibody and administration of other therapies (the therapeutic modalities or the therapeutic agents) occur within about one month, or within about one, two, or three weeks, or within about 1, 2, 3, 4, 5 or 6 days from each other.

In some embodiments, the antibody combinations described herein can be administered separately (e.g., as separate antibodies) or in linkage (e.g., as a bispecific or trispecific antibody molecule).

It will be appreciated that any therapy can be performed by using the immunoconjugate of the invention in place of or in addition to the anti-PD-L1 antibody.

Combination Therapy with Anti-LAG-3 Antibody

In some embodiments, the anti-PD-L1 antibody of the invention may be used for treatment in combination with an anti-LAG-3 antibody.

In some embodiments, the anti-LAG-3 antibody of the invention is an anti-human LAG-3 antibody. In some embodiments, the anti-LAG-3 antibody of the invention is an IgG1 antibody or an IgG2 antibody or an IgG4 antibody. In some embodiments, the anti-LAG-3 antibody is a monoclonal antibody. In some embodiments, the anti-LAG-3 antibody is humanized. In some embodiments, the anti-LAG-3 antibody is a chimeric antibody. In some embodiments, at least a portion of the framework sequence of the anti-LAG-3 antibody is a human consensus framework sequence. In one embodiment, the anti-LAG-3 antibody of the invention also comprises an antibody fragment thereof, preferably an antibody fragment selected from the group consisting of: Fab, Fab', Fab'-SH, Fv, single-chain variable fragment (e.g., scFv) or (Fab')$_2$, single-domain antibody, diabody (dAb), or linear antibody.

In some specific embodiments, the anti-LAG-3 antibody or the antigen-binding fragment thereof of the invention comprises:

(i) three heavy-chain complementarity determining regions (HCDRs) of the heavy chain variable region shown in SEQ ID NO: 75, and/or (ii) three light-chain complementarity determining regions (LCDRs) of the light chain variable region shown in SEQ ID NO: 76.

In some embodiments, the anti-LAG-3 antibody or the antigen-binding fragment thereof of the invention comprises a heavy chain variable region (VH) and/or a light chain variable region (VL), wherein (i) the VH comprises complementarity determining regions (CDRs) HCDR1, HCDR2 and HCDR3, wherein the HCDR1 comprises or consists of the amino acid sequence of SEQ ID NO: 69; the HCDR2 comprises an amino acid sequence selected from SEQ ID NO: 70 or consists of the amino acid sequence; the HCDR3 comprises or consists of the amino acid sequence of SEQ ID NO: 71;

and/or (ii) the VL comprises complementarity determining regions (CDRs) LCDR1, LCDR2, and LCDR3, wherein the LCDR1 comprises or consists of the amino acid sequence of SEQ ID NO: 72; the LCDR2 comprises or consists of the amino acid sequence of SEQ ID NO: 73; the LCDR3 comprises an amino acid sequence selected from SEQ ID NO: 74 or consists of the amino acid sequence.

In some embodiments, the anti-LAG-3 antibody or the antigen-binding fragment thereof of the invention comprises a heavy chain variable region VH and/or a light chain variable region VL, wherein
  (a) the heavy chain variable region VH
    (i) comprises or consists of an amino acid sequence having at least 90%, 91%, 92%, 93%, 94%, 95%, 96%, 97%, 98% or 99% identity to an amino acid sequence selected from SEQ ID NO: 75,
    (ii) comprises or consists of an amino acid sequence selected from SEQ ID NO: 75, or
    (iii) comprises an amino acid sequence having 1 or more (preferably not more than 10, more preferably not more than 5, 4, 3, 2 or 1) amino acid alterations (preferably amino acid substitutions, more preferably amino acid conservative substitutions) as compared to an amino acid sequence selected from the SEQ ID NO: 75, wherein preferably, the amino acid alterations do not occur in the CDRs;
  and/or
  (b) the light chain variable region VL
    (i) comprises or consists of an amino acid sequence having at least 90%, 91%, 92%, 93%, 94%, 95%, 96%, 97%, 98% or 99% identity to an amino acid sequence selected from SEQ ID NO: 76,
    (ii) comprises or consists of an amino acid sequence selected from SEQ ID NO: 76, or
    (iii) comprises an amino acid sequence having 1 or more (preferably not more than 10, more preferably not more than 5, 4, 3, 2 or 1) amino acid alterations (preferably amino acid substitutions, more preferably amino acid conservative substitutions) as compared to an amino acid sequence selected from the SEQ ID NO: 76, wherein preferably, the amino acid alterations do not occur in the CDRs.

In some embodiments, the anti-LAG-3 antibody or the antigen-binding fragment thereof of the invention comprises a heavy chain and/or a light chain, wherein
  (a) the heavy chain
    (i) comprises or consists of an amino acid sequence having at least 85%, 90%, 91%, 92%, 93%, 94%, 95%, 96%, 97%, 98% or 99% identity to an amino acid sequence selected from SEQ ID NO: 77,
    (ii) comprises or consists of an amino acid sequence selected from SEQ ID NO: 77, or
    (iii) comprises an amino acid sequence having 1 or more (preferably not more than 20 or 10, more preferably not more than 5, 4, 3, 2 or 1) amino acid alterations (preferably amino acid substitutions, more preferably amino acid conservative substitutions) as compared to an amino acid sequence selected from the SEQ ID NO: 77, wherein preferably, the amino acid alterations do not occur in the CDRs of the heavy chain, and more preferably, the amino acid alterations do not occur in the heavy chain variable region;
  and/or
  (b) the light chain
    (i) comprises or consists of an amino acid sequence having at least 85%, 90%, 91%, 92%, 93%, 94%, 95%, 96%, 97%, 98% or 99% identity to an amino acid sequence selected from SEQ ID NO: 78,
    (ii) comprises or consists of an amino acid sequence selected from SEQ ID NO: 78, or
    (iii) comprises an amino acid sequence having 1 or more (preferably not more than 20 or 10, more preferably not more than 5, 4, 3, 2 or 1) amino acid alterations (preferably amino acid substitutions, more preferably amino acid conservative substitutions) as compared to an amino acid sequence selected from the SEQ ID NO: 78, wherein preferably, the amino acid alterations do not occur in the CDRs of the light chain, and more preferably, the amino acid alterations do not occur in the light chain variable region.

In some embodiments, modifications for the anti-PD-L1 antibody of the invention also apply to the anti-LAG-3 antibody.

Route of Administration and Dosage

The antibody of the invention (or the pharmaceutical composition or the immunoconjugate containing the antibody, or any other therapeutic agents) can be administered by any suitable means, including parenteral administration, intrapulmonary administration, intranasal administration, and intralesional administration if needed by local treatment. Parenteral infusion includes intramuscular, intravenous, intraarterial, intraperitoneal, or subcutaneous administration. The drugs may be administered by any suitable means, such as injection, e.g., intravenous or subcutaneous injection, to some extent depending on short-term or long-term treatment. Various dosing schedules are contemplated herein, including, but not limited to, single administration or multiple administrations, bolus injections, and pulse infusions at multiple time points.

In order to prevent or treat a disease, the appropriate dosage (when used alone or in combination with one or more of other therapeutic agents) of the antibody of the invention will depend on the type of the disease to be treated, the type of the antibody, the severity and progression of the disease, whether the antibody is administered for prophylactic or therapeutic purposes, previous treatments, clinical history of a patient and responses to the antibody, and the discretion of an attending physician. The antibody is suitably administered to a patient through a single dose or through a series of treatments.

In some embodiments, the dose regimen is adjusted to provide the optimal desired response (for example, a therapeutic response). For example, a single bolus injection may be given, several separate doses may be administered over time, or a dose may be proportionally reduced or increased as indicated by the criticality of the treatment condition. It is particularly advantageous to formulate a parenteral composition in a dosage unit form for ease of dose administration and uniformity. The dosage unit form as used herein refers to physically separated units suitable as unitary doses for subjects to be treated; each unit contains a predetermined quantity of active compound, which is calculated to produce a desired therapeutic effect in combination with a required pharmaceutical carrier. The specification of the dosage unit form of the invention is directly dependent on (a) the unique characteristics of the active compound and the particular therapeutic effect to be achieved, and (b) limitations which are unique in the field of combining the active compound for a sensitive therapy in an individual.

The dosage and regimen of the anti-PD-L1 antibody molecule can be determined by those skilled. In certain embodiments, the anti-PD-L1 antibody molecule is administered (e.g., subcutaneously or intravenously) through injection at a dose of about 1 to 30 mg/kg, e.g., about 5 to 25 mg/kg, about 10 to 20 mg/kg, about 1 to 5 mg/kg, or about 3 mg/kg. The regimen may range from, for example, once a week to once every 2, 3, or 4 weeks. In one embodiment, the anti-PD-L1 antibody molecule is administered every other week at a dose of about 10 to 20 mg/kg. In one embodiment, the anti-PD-L1 antibody molecule is administered at a dose of less than or equal to about 5 mg/kg, less than or equal to about 4 mg/kg, less than or equal to about 3 mg/kg, less than or equal to about 2 mg/kg, or less than or equal to about 1 mg/kg every other week, alone or in combination (e.g., in combination with an anti-LAG-3 antibody molecule). In one embodiment, the anti-PD-L1 antibody molecule is administered at a dose of about 1 to 5 mg/kg every other week, at a dose of about 1 to 4 mg/kg every other week, at a dose of about 1 to 3 mg/kg every other week, or at a dose of about 1 to 2 mg/kg every other week. In one embodiment, the anti-PD-L1 antibody molecule is administered alone or in combination (e.g., in combination with an anti-LAG-3 antibody molecule) at a dose of about 1 to 5 mg/kg every other week, at a dose of about 1 to 4 mg/kg every other week, at a dose of about 1 to 3 mg/kg every other week, or at a dose of about 1 to 2 mg/kg every other week.

Method and Composition for Diagnosis and Detection

In certain embodiments, any of the anti-PD-L1 antibodies or the antigen-binding fragments thereof provided herein can be used for detection of the presence of PD-L1 in a biological sample. The term "detection" as used herein includes quantitative or qualitative detection, and exemplary detections may involve immunohistochemistry, immunocytochemistry, flow cytometry (e.g., FACS), magnetic beads complexed with antibody molecules, ELISA, and PCR techniques (e.g., RT-PCR). In some embodiments, the biological sample is blood, serum, or other fluid sample of biological source. In certain embodiments, the biological sample includes cells or tissues. In some embodiments, the biological sample is derived from a proliferative or cancerous lesion.

In one embodiment, an anti-PD-L1 antibody is provided for use in a diagnostic or detection method. In another aspect, a method for detecting the presence of PD-L1 in a biological sample is provided. In certain embodiments, the method comprises detecting the presence of PD-L1 proteins in a biological sample. In certain embodiments, the PD-L1 is human PD-L1. In certain embodiments, the method comprises contacting the biological sample with the anti-PD-L1 antibody as described herein in a condition that allows the anti-PD-L1 antibody to bind to PD-L1, and detecting whether a complex is formed by the anti-PD-L1 antibody and PD-L1. The formation of the complex indicates the presence of PD-L1. The method may be an in-vitro or in-vivo method. In one embodiment, the anti-PD-L1 antibody is used to select a subject suitable for treatment with the anti-PD-L1 antibody, e.g., wherein PD-L1 is a biomarker for selecting the subject.

In one embodiment, the antibody of the invention can be used to diagnose cancers or tumors, e.g., to assess (e.g., monitor) the treatment or progression, diagnosis and/or staging of a disease (e.g., the hyperproliferative or cancerous disease) described herein in a subject. In certain embodiments, a labeled anti-PD-L1 antibody is provided. The label includes, but is not limited to, a label or moiety (e.g., a fluorescent label, a chromophoric label, an electron-dense label, a chemiluminescent label, and a radioactive label) that is detected directly, as well as a moiety that is detected indirectly, such as an enzyme or a ligand, for example, by an enzymatic reaction or a molecular interaction. Exemplary labels include, but are not limited to, radioisotopes of $^{32}P$, $^{14}C$, $^{125}I$, $^{3}H$, and $^{131}I$, fluorophores (e.g., rare earth chelates or luciferin and derivatives thereof), rhodamine and derivatives thereof, dansyl, umbelliferone, luceriferase [e.g., firefly luciferase and bacterial luciferase (U.S. Pat. No. 4,737, 456)], luciferin, 2,3-dihydrophthalazinedione, horseradish peroxidase (HR), alkaline phosphatase, beta-galactosidase, glucoamylase, lysase, carbohydrate oxidases (e.g., glucose oxidase, galactose oxidase, and glucose-6-phosphate dehydrogenase), heterocyclic oxidases (e.g., uricase and xanthine oxidase), enzymes utilizing hydrogen peroxide to oxidize dye precursors (e.g., HR, lactoperoxidase, or microperoxidase), biotin/avidin, spin labels, phage labels, stable free radicals, and the like.

In some embodiments of the invention provided herein, the sample is obtained prior to treatment with the anti-PD-L1 antibody. In some embodiments, the sample is obtained prior to treatment with an anti-cancer drug. In some embodiments, the sample is obtained after the cancer has metastasized. In some embodiments, the sample is a formalin-fixed, paraffin-embedded (FFPE) sample. In some embodiments, the sample is a biopsy (e.g., a core biopsy) specimen, a surgical specimen (e.g., a specimen from a surgical resection), or a fine-needle aspirate.

In some embodiments, PD-L1 is detected prior to treatment, e.g., prior to initial treatment or prior to a treatment after an interval from a certain treatment.

In some embodiments, a method for treating a tumor or infection is provided, which comprises: detecting the presence of PD-L1 in a subject (for example, using a sample, e.g., a sample containing cancer cells of the subject), thereby determining a PD-L1 value, comparing the PD-L1 value to a control value; and if the PD-L1 value is greater than the control value, administering a therapeutically effective amount of an anti-PD-L1 antibody (e.g., the anti-PD-L1 antibody described herein), optionally in combination with one or more of other therapies, to the subject, thereby treating the tumor or infection.

Exemplary Sequences of Anti-PD-L1 Antibodies of the Invention

TABLE 1

CDR sequences of heavy and light chain variable regions of exemplary antibodies of the invention and of control antibodies described herein (in parentheses are certainty rules)

| Antibody | HCDR1 (Chothia) | HCDR2 (Chothia) | HCDR3 (Chothia) | LCDR1 (Kabat) | LCDR2 (Kabat) | LCDR3 (Kabat) |
|---|---|---|---|---|---|---|
| 3-266.1 | GFNIEDT (SEQ ID NO: 1) | DPANDD SEQ ID NO: 5) | GLGRWF AY (SEQ ID NO: 10) | KASQDVINA VA (SEQ ID NO: 14) | SASNRY T (SEQ ID NO: 17) | QQHYSPPL T (SEQ ID NO: 21) |
| 4-79.2 | GDSITSG (SEQ ID NO: 2) | SYTGS (SEQ ID NO: 6) | APPWLSA MDY (SEQ ID NO: 11) | KSSQSLLYSS NQKNSLA (SEQ ID NO: 15) | WASTRE S (SEQ ID NO:18) | QQYYSYP WT (SEQ ID NO: 22) |

TABLE 1-continued

CDR sequences of heavy and light chain variable regions of exemplary antibodies of the invention and of control antibodies described herein (in parentheses are certainty rules)

| Antibody | HCDR1 (Chothia) | HCDR2 (Chothia) | HCDR3 (Chothia) | LCDR1 (Kabat) | LCDR2 (Kabat) | LCDR3 (Kabat) |
|---|---|---|---|---|---|---|
| 4-26.6 | GDSITSG (SEQ ID NO: 2) | SYSGS (SEQ ID NO: 7) | GDLWPPWFAY (SEQ ID NO: 12) | KSSQSLLYSSNQKNSLA (SEQ ID NO: 15) | WASTRES (SEQ ID NO: 18) | QQYYGYPLT (SEQ ID NO: 23) |
| 4-48.5 | GYTFTTY (SEQ ID NO: 3) | NPNSDY (SEQ ID NO: 8) | QSFDY (SEQ ID NO: 13) | RASESVEFYGTSLLQ (SEQ ID NO: 16) | AASNVES (SEQ ID NO: 19) | HQGRKVPYT (SEQ ID NO: 24) |
| HZ3266-IgG1N297A | GFNIEDT (SEQ ID NO: 1) | DPANDD (SEQ ID NO: 5) | GLGRWFAY (SEQ ID NO: 10) | KASQDVINAVA (SEQ ID NO: 14) | SASNRYT (SEQ ID NO: 17) | QQHYSPPLT (SEQ ID NO: 21) |
| HZ3266-IgG1 | GFNIEDT (SEQ ID NO: 1) | DPANDD (SEQ ID NO: 5) | GLGRWFAY (SEQ ID NO: 10) | KASQDVINAVA (SEQ ID NO: 14) | SASNRYT (SEQ ID NO: 17) | QQHYSPPLT (SEQ ID NO: 21) |
| HZ3266-IgG4PAAK | GFNIEDT (SEQ ID NO: 1) | DPANDD (SEQ ID NO: 5) | GLGRWFAY (SEQ ID NO: 10) | KASQDVINAVA (SEQ ID NO: 14) | SASNRYT (SEQ ID NO: 17) | QQHYSPPLT (SEQ ID NO: 21) |
| HZ4485-IgG1N297A | GYTFTTY (SEQ ID NO: 3) | NPNSDY (SEQ ID NO: 8) | QSFDY (SEQ ID NO: 13) | RASESVEFYGTSLLQ (SEQ ID NO: 16) | AASNVES (SEQ ID NO: 19) | HQGRKVPYT (SEQ ID NO: 24) |
| Consensus sequence | $X_1X_2X_3X_4X_5X_6X_7$ (wherein $X_1$ is G, $X_2$ is selected from D, F, or Y, $X_3$ is selected from N, S, or T, $X_4$ is selected from I or F, $X_5$ is selected from T or E, $X_6$ is selected from S, D, or T, and $X_7$ is selected from G, T, or Y) (SEQ ID NO: 4) | SYXGS (wherein X is selected from T or S) (SEQ ID NO: 9) | | $X_1X_2X_3X_4X_5X_6X_7$ (wherein $X_1$ is selected from S, W, or A, $X_2$ is A, $X_3$ is S, $X_4$ is selected from N or T, $X_5$ is selected from R or V, $X_6$ is selected from Y or E, and $X_7$ is selected from T or S) (SEQ ID NO: 20) | $X_1X_2X_3X_4X_5X_6X_7X_8X_9$ (wherein $X_1$ is selected from Q or H, $X_2$ is Q, $X_3$ is selected from H, Y, or G, $X_4$ is selected from Y or R, $X_5$ is selected from S, G, or K, $X_6$ is selected from P, Y, or V, $X_7$ is P, $X_8$ is selected from L, W, or Y, and $X_9$ is T) (SEQ ID NO: 25) |
| ATE | GFTFSDS (SEQ ID NO: 52) | SPYGGS (SEQ ID NO: 53) | RHWPGGFDY (SEQ ID NO: 54) | QDVSTAVA (SEQ ID NO: 55) | SASFLYS (SEQ ID NO: 56) | QQYLYHPAT (SEQ ID NO: 57) |
| ADI-31853* | GSIYSESYYWG (SEQ ID NO: 69) | SIVYSGYTYYNPSLKS (SEQ ID NO: 70) (Kabat rule) | ARVRTWDAAFDI (SEQ ID NO: 71) (IMGT rule) | QASQDISNYLN (SEQ ID NO: 72) (Kabat rule) | DASNLET (SEQ ID NO: 73) (Kabat rule) | QQVLELPPWT (SEQ ID NO: 74) (Kabat rule) |

*CDR definition rule of ADI-31853 is listed in the line.

TABLE 2

Heavy and light chain variable regions of exemplary antibodies of the invention and of control antibodies described herein

| Antibody | Heavy chain variable region (VH) | Light chain variable region (VL) |
|---|---|---|
| 3-266.1 | EVQLQQSVAELVKPGASVKLSCTASGF NIEDTYIHWVKQRPEQGLEWIGRIDPAN DDTKYDPKFQGKATITADTSSNTAYLQ LSSLTPEDTAVYYCGRGLGRWFAYWG QGTLVTVSA (SEQ ID NO: 26) | SIVMTQSHKFMSTSIGDRVNISCKASQDV INAVAWCQQKPGQSPKLLIYSASNRYTG VPDRFTGSGSGTDFTFTISSVQAEDLAVY YCQQHYSPPLTFGGGTKLELK (SEQ ID NO: 32) |
| 4-79.2 | EVQLQQSGPSLVKPSQTLSLTCSVTGDS ITSGYWNWIREFPGNKLEYLGYISYTGS TYYNPSLKSRISITRDTSKNQYSLQLNSV TTEDTATYYCAKAPRWLSAMDYWGQ GTSVTVSS (SEQ ID NO: 27) | DIVMSQSPSSLAVSVGEKITMSCKSSQSL LYSSNQKNSLAWYQQKPGQSPKLLIYWA STRESGVPDRFTGSGSGTDFTLTISSVKAE DLAVYYCQQYYSYPWTFGGGTKLEIK (SEQ ID NO: 33) |
| 4-26.6 | QVQLKESGPSLVKPSQTLSLTCSVTGDS ITSGYWNWIRKFPGNKLEYMGYISYSG STYHNPSLKSRISITRDTSKNQFYLQLNS VTKEDTATYYCARGDLWPPWFAYWG QGTLVTVSA (SEQ ID NO: 28) | NIVMTQTPSSLAVSVGEKITMSCKSSQSL LYSSNQKNSLAWYQQKPGQSPKLLIYWA STRESGVPDRFTGSGSGTDFTLTISSVEAE DLAVYYCQQYYGYPLTFGAGTKLELK (SEQ ID NO: 34) |
| 4-48.5 | EVQLQQSGAELARPGASVKMSCKASG YTFTTYTMHWVKQRPGQGLEWIGNINP NSDYAIYNQKFKDKATLTADKSSNTAY MQLSGLTSEDSAVYYCAKQSFDYWGQ GTTLTVSS (SEQ ID NO: 29) | DIVLTQSPASLAVSLGQRATISCRASESVE FYGTSLLQWYQQKPGQPPKLLIYAASNV ESGVPARFSGSGSGTDFSLNIHPVEVDDV ALYFCHQGRKVPYTFGGGTKLEIK (SEQ ID NO: 35) |
| HZ3266-IgG1N297A | EVQLVQSGAEVKKPGATVKISCTASGF NIEDTYIHWVQQAPGQGLEWIGRIDPA NDDTKYAPKFQGRATITADTSTDTAYM ELSSLRSEDTAVYYCGRGLGRWFAYW GQGTLVTVSS (SEQ ID NO: 30) | GIVMTQSPDSLAVSLGERATINCKASQDV INAVAWYQQKPGQSPKLLIYSASNRYTG VPDRFSGSGSGTDFTLTISSLQAEDLAVY YCQQHYSPPLTFGGGTKVEIK (SEQ ID NO: 36) |
| HZ3266-IgG1 | EVQLVQSGAEVKKPGATVKISCTASGF NIEDTYIHWVQQAPGQGLEWIGRIDPA NDDTKYAPKFQGRATITADTSTDTAYM ELSSLRSEDTAVYYCGRGLGRWFAYW GQGTLVTVSS (SEQ ID NO: 30) | GIVMTQSPDSLAVSLGERATINCKASQDV INAVAWYQQKPGQSPKLLIYSASNRYTG VPDRFSGSGSGTDFTLTISSLQAEDLAVY YCQQHYSPPLTFGGGTKVEIK (SEQ ID NO: 36) |
| HZ3266-IgG4PAAK | EVQLVQSGAEVKKPGATVKISCTASGF NIEDTYIHWVQQAPGQGLEWIGRIDPA NDDTKYAPKFQGRATITADTSTDTAYM ELSSLRSEDTAVYYCGRGLGRWFAYW GQGTLVTVSS (SEQ ID NO: 30) | GIVMTQSPDSLAVSLGERATINCKASQDV INAVAWYQQKPGQSPKLLIYSASNRYTG VPDRFSGSGSGTDFTLTISSLQAEDLAVY YCQQHYSPPLTFGGGTKVEIK (SEQ ID NO: 36) |
| HZ4485-IgG1N297A | QVQLVQSGAEVAKPGASVKVSCKASG YTFTTYTMHWVRQRPGQGLEWIGNINP NSDYAIYAQKFQGRATMTADKSTNTA YMELSSLRSEDSAVYYCAKQSFDYWG QGTLVTVSS (SEQ ID NO: 31) | DIVLTQSPASLAVSPGQRATITCRASESVE FYGTSLLQWYQQKPGQPPKLLIYAASNV ESGVPARFSGSGSGTDFTLTINPVEADDT ANYYCHQGRKVPYTFGQGTKLEIK (SEQ ID NO: 37) |
| ATE | EVQLVESGGGLVQPGGSLRLSCAASGF TFSDSWIHWVRQAPGKGLEWVAWISPY GGSTYYADSVKGRFTISADTSKNTAYL QMNSLRAEDTAVYYCARRHWPGGFDY WGQGTLVTVSS (SEQ ID NO: 58) | DIQMTQSPSSLSASVGDRVTITCRASQDV STAVAWYQQKPGKAPKLLIYSASFLYSG VPSRFSGSGSGTDFTLTISSLQPEDFATYY CQQYLYHPATFGQGTKVEIK (SEQ ID NO: 59) |
| ADI-31853 | QLQLQESGPGLVKPSETLSLTCTVSGGSI YSESYYWGWIRQPPGKGLEWIGSIVYS GYTYYNPSLKSRVTISVDTSKNQFSLKL SSVTAADTAVYYCARVRTWDAAFDIW GQGTMVTVSS (SEQ ID NO: 75) | DIQMTQSPSSLSASVGDRVTITCQASQDIS NYLNWYQQKPGKAPKLLIYDASNLETG VPSRFSGSGSGTDFTFTISSLQPEDIATYY CQQVLELPPWTFGGGTKVEIK (SEQ ID NO: 76) |

TABLE 3

Heavy and light chains of exemplary antibodies of the invention and of control antibodies described herein

| Antibody | Heavy chain (HC) | Light chain (LC) |
|---|---|---|
| 3-266.1 | EVQLQQSVAELVKPGASVKLSCTASGF NIEDTYIHWVKQRPEQGLEWIGRIDPAN DDTKYDPKFQGKATITADTSSNTAYLQ LSSLTPEDTAVYYCGRGLGRWFAYWG QGTLVTVSAASTKGPSVFPLAPSSKSTS | SIVMTQSHKFMSTSIGDRVNISCKASQDV INAVAWCQQKPGQSPKLLIYSASNRYTG VPDRFTGSGSGTDFTFTISSVQAEDLAVY YCQQHYSPPLTFGGGTKLELKRTVAAPS VFIFPPSDEQLKSGTASVVCLLNNFYPRE |

TABLE 3-continued

Heavy and light chains of exemplary antibodies of the invention and of control antibodies described herein

| Antibody | Heavy chain (HC) | Light chain (LC) |
|---|---|---|
| | GGTAALGCLVKDYFPEPVTVSWNSGAL TSGVHTFPAVLQSSGLYSLSSVVTVPSS SLGTQTYICNVNHKPSNTKVDKKVEPK SCDKTHTCPPCPAPELLGGPSVFLFPPKP KDTLMISRTPEVTCVVVDVSHEDPEVK FNWYVDGVEVHNAKTKPREEQYASTY RVVSVLTVLHQDWLNGKEYKCKVSNK ALPAPIEKTISKAKGQPREPQVYTLPPSR EEMTKNQVSLTCLVKGFYPSDIAVEWE SNGQPENNYKTTPPVLDSDGSFFLYSKL TVDKSRWQQGNVFSCSVMHEALHNHY TQKSLSLSPGK (SEQ ID NO: 38) | AKVQWKVDNALQSGNSQESVTEQDSKD STYSLSSTLTLSKADYEKHKVYACEVTH QGLSSPVTKSFNRGEC (SEQ ID NO: 46) |
| 4-79.2 | EVQLQQSGPSLVKPSQTLSLTCSVTGDS ITSGYWNWIREFPGNKLEYLGYISYTGS TYYNPSLKSRISITRDTSKNQYSLQLNSV TTEDTATYYCAKAPRWLSAMDYWGQ GTSVTVSSASTKGPSVFPLAPSSKSTSGG TAALGCLVKDYFPEPVTVSWNSGALTS GVHTFPAVLQSSGLYSLSSVVTVPSSSL GTQTYICNVNHKPSNTKVDKKVEPKSC DKTHTCPPCPAPELLGGPSVFLFPPKPK DTLMISRTPEVTCVVVDVSHEDPEVKF NWYVDGVEVHNAKTKPREEQYASTYR VVSVLTVLHQDWLNGKEYKCKVSNKA LPAPIEKTISKAKGQPREPQVYTLPPSRE EMTKNQVSLTCLVKGFYPSDIAVEWES NGQPENNYKTTPPVLDSDGSFFLYSKLT VDKSRWQQGNVFSCSVMHEALHNHYT QKSLSLSPGK (SEQ ID NO: 39) | DIVMSQSPSSLAVSVGEKITMSCKSSQSL LYSSNQKNSLAWYQQKPGQSPKLLIYW ASTRESGVPDRFTGSGSGTDFTLTISSVK AEDLAVYYCQQYYSYPWTFGGGTKLEI KRTVAAPSVFIFPPSDEQLKSGTASVVCL LNNFYPREAKVQWKVDNALQSGNSQES VTEQDKDSTYSLSSTLTLSKADYEKHK VYACEVTHQGLSSPVTKSFNRGEC (SEQ ID NO: 47) |
| 4-26.6 | QVQLKESGPSLVKPSQTLSLTCSVTGDS ITSGYWNWIRKFPGNKLEYMGYISYSG STYHNPSLKSRISITRDTSKNQFYLQLNS VTKEDTATYYCARGDLWPPWFAYWG QGTLVTVSAASTKGPSVFPLAPSSKSTS GGTAALGCLVKDYFPEPVTVSWNSGAL TSGVHTFPAVLQSSGLYSLSSVVTVPSS SLGTQTYICNVNHKPSNTKVDKKVEPK SCDKTHTCPPCPAPELLGGPSVFLFPPKP KDTLMISRTPEVTCVVVDVSHEDPEVK FNWYVDGVEVHNAKTKPREEQYASTY RVVSVLTVLHQDWLNGKEYKCKVSNK ALPAPIEKTISKAKGQPREPQVYTLPPSR EEMTKNQVSLTCLVKGFYPSDIAVEWE SNGQPENNYKTTPPVLDSDGSFFLYSKL TVDKSRWQQGNVFSCSVMHEALHNHY TQKSLSLSPGK (SEQ ID NO: 40) | NIVMTQTPSSLAVSVGEKITMSCKSSQSL LYSSNQKNSLAWYQQKPGQSPKLLIYW ASTRESGVPDRFTGSGSGTDFTLTISSVEA EDLAVYYCQQYYGYPLTFGAGTKLELK RTVAAPSVFIFPPSDEQLKSGTASVVCLL NNFYPREAKVQWKVDNALQSGNSQES VTEQDSKDSTYSLSSTLTLSKADYEKHKV YACEVTHQGLSSPVTKSFNRGEC (SEQ ID NO: 48) |
| 4-48.5 | EVQLQQSGAELARPGASVKMSCKASG YTFTTYTMHWVKQRPGQGLEWIGNINP NSDYAIYNQKFKDKATLTADKSSNTAY MQLSGLTSEDSAVYYCAKQSFDYWGQ GTTLTVSSASTKGPSVFPLAPSSKSTSGG TAALGCLVKDYFPEPVTVSWNSGALTS GVHTFPAVLQSSGLYSLSSVVTVPSSSL GTQTYICNVNHKPSNTKVDKKVEPKSC DKTHTCPPCPAPELLGGPSVFLFPPKPK DTLMISRTPEVTCVVVDVSHEDPEVKF NWYVDGVEVHNAKTKPREEQYASTYR VVSVLTVLHQDWLNGKEYKCKVSNKA LPAPIEKTISKAKGQPREPQVYTLPPSRE EMTKNQVSLTCLVKGFYPSDIAVEWES NGQPENNYKTTPPVLDSDGSFFLYSKLT VDKSRWQQGNVFSCSVMHEALHNHYT QKSLSLSPGK (SEQ ID NO: 41) | DIVLTQSPASLAVSLGQRATISCRASESVE FYGTSLLQWYQQKPGQPPKLLIYAASNV ESGVPARFSGSGSGTDFSLNIFIPVEVDDV ALYFCHQGRKVPYTFGGGTKLEIKRTVA APSVFIFPPSDEQLKSGTASVVCLLNNFY PREAKVQWKVDNALQSGNSQESVTEQD SKDSTYSLSSTLTLSKADYEKHKVYACE VTHQGLSSPVTKSFNRGEC (SEQ ID NO: 49) |
| HZ3266- IgG1N297A | EVQLVQSGAEVKKPGATVKISCTASGF NIEDTYIHWVQQAPGQGLEWIGRIDPA NDDTKYAPKFQGRATITADTSTDTAYM ELSSLRSEDTAVYYCGRGLGRWFAYW GQGTLVTVSSASTKGPSVFPLAPSSKST SGGTAALGCLVKDYFPEPVTVSWNSGA | GIVMTQSPDSLAVSLGERATINCKASQD VINAVAWYQQKPGQSPKLLIYSASNRYT GVPDRFSGSGSGTDFTLTISSLQAEDLAV YYCQQHYSPPLTFGGGTKVEIKRTVAAP SVFIFPPSDEQLKSGTASVVCLLNNFYPR EAKVQWKVDNALQSGNSQESVTEQDSK |

TABLE 3-continued

Heavy and light chains of exemplary antibodies of the invention and of control antibodies described herein

| Antibody | Heavy chain (HC) | Light chain (LC) |
|---|---|---|
|  | LTSGVHTFPAVLQSSGLYSLSSVVTVPS SSLGTQTYICNVNHKPSNTKVDKKVEP KSCDKTHTCPPCPAPELLGGPSVFLFPP KPKDTLMISRTPEVTCVVVDVSHEDPE VKFNWYVDGVEVHNAKTKPREEQYAS TYRVVSVLTVLHQDWLNGKEYKCKVS NKALPAPIEKTISKAKGQPREPQVYTLP PSREEMTKNQVSLTCLVKGFYPSDIAVE WESNGQPENNYKTTPPVLDSDGSFFLY SKLTVDKSRWQQGNVFSCSVMHEALH NHYTQKSLSLSPGK (SEQ ID NO: 42) | DSTYSLSSTLTLSKADYEKHKVYACEVT HQGLSSPVTKSFNRGEC (SEQ ID NO: 50) |
| HZ3266-IgG1 | EVQLVQSGAEVKKPGATVKISCTASGF NIEDTYIHWVQQAPGQGLEWIGRIDPA NDDTKYAPKFQGRATITADTSTDTAYM ELSSLRSEDTAVYYCGRGLGRWFAYW GQGTLVTVSSASTKGPSVFPLAPSSKST SGGTAALGCLVKDYFPEPVTVSWNSGA LTSGVHTFPAVLQSSGLYSLSSVVTVPS SSLGTQTYICNVNHKPSNTKVDKKAEP KSCDKTHTCPPCPAPELLGGPSVFLFPP KPKDTLMISRTPEVTCVVVDVSHEDPE VKFNWYVDGVEVHNAKTKPREEQYNS TYRVVSVLTVLHQDWLNGKEYKCKVS NKALPAPIEKTISKAKGQPREPQVYTLP PSRDELTKNQVSLTCLVKGFYPSDIAVE WESNGQPENNYKTTPPVLDSDGSFFLY SKLTVDKSRWQQGNVFSCSVMHEALH NHYTQKSLSLSPGK (SEQ ID NO: 43) | GIVMTQSPDSLAVSLGERATINCKASQD VINAVAWYQQKPGQSPKLLIYSASNRYT GVPDRFSGSGSGTDFTLTISSLQAEDLAV YYCQQHYSPPLTFGGGTKVEIKRTVAAP SVFIFPPSDEQLKSGTASVVCLLNNFYPR EAKVQWKVDNALQSGNSQESVTEQDSK DSTYSLSSTLTLSKADYEKHKVYACEVT HQGLSSPVTKSFNRGEC (SEQ ID NO: 50) |
| HZ3266-IgG4PAAK | EVQLVQSGAEVKKPGATVKISCTASGF NIEDTYIHWVQQAPGQGLEWIGRIDPA NDDTKYAPKFQGRATITADTSTDTAYM ELSSLRSEDTAVYYCGRGLGRWFAYW GQGTLVTVSSASTKGPSVFPLAPCSRST SESTAALGCLVKDYFPEPVTVSWNSGA LTSGVHTFPAVLQSSGLYSLSSVVTVPS SSLGTKTYTCNVDHKPSNTKVDKRVES KYGPPCPPCPAPEAAGGPSVFLFPPKPK DTLMISRTPEVTCVVVDVSQEDPEVQF NWYVDGVEVHNAKTKPREEQFNSTYR VVSVLTVLHQDWLNGKEYKCKVSNKG LPSSIEKTISKAKGQPREPQVYTLPPSQE EMTKNQVSLTCLVKGFYPSDIAVEWES NGQPENNYKTTPPVLDSDGSFFLYSRLT VDKSRWQEGNVFSCSVMHEALHNHYT QKSLSLSLG (SEQ ID NO: 44) | GIVMTQSPDSLAVSLGERATINCKASQD VINAVAWYQQKPGQSPKLLIYSASNRYT GVPDRFSGSGSGTDFTLTISSLQAEDLAV YYCQQHYSPPLTFGGGTKVEIKRTVAAP SVFIFPPSDEQLKSGTASVVCLLNNFYPR EAKVQWKVDNALQSGNSQESVTEQDSK DSTYSLSSTLTLSKADYEKHKVYACEVT HQGLSSPVTKSFNRGEC (SEQ ID NO: 50) |
| HZ4485-IgG1N297A | QVQLVQSGAEVAKPGASVKVSCKASG YTFTTYTMHWVRQRPGQGLEWIGNINP NSDYAIYAQKFQGRATMTADKSTNTA YMELSSLRSEDSAVYYCAKQSFDYWG QGTLVTVSSASTKGPSVFPLAPSSKSTS GGTAALGCLVKDYFPEPVTVSWNSGAL TSGVHTFPAVLQSSGLYSLSSVVTVPSS SLGTQTYICNVNHKPSNTKVDKKVEPK SCDKTHTCPPCPAPELLGGPSVFLFPPKP KDTLMISRTPEVTCVVVDVSHEDPEVK FNWYVDGVEVHNAKTKPREEQYASTY RVVSVLTVLHQDWLNGKEYKCKVSNK ALPAPIEKTISKAKGQPREPQVYTLPPSR EEMTKNQVSLTCLVKGFYPSDIAVEWE SNGQPENNYKTTPPVLDSDGSFFLYSKL TVDKSRWQQGNVFSCSVMHEALHNHY TQKSLSLSPGK (SEQ ID NO: 45) | DIVLTQSPASLAVSPGQRATITCRASESVE FYGTSLLQWYQQKPGQPPKLLIYAASNV ESGVPARFSGSGSGTDFTLTINPVEADDT ANYYCHQGRKVPYTFGQGTKLEIKRTVA APSVFIFPPSDEQLKSGTASVVCLLNNFY PREAKVQWKVDNALQSGNSQESVTEQD SKDSTYSLSSTLTLSKADYEKHKVYACE VTHQGLSSPVTKSFNRGEC (SEQ ID NO: 51) |
| ATE | EVQLVESGGGLVQPGGSLRLSCAASGF TFSDSWIFIWVRQAPGKGLEWVAWISPY GGSTYYADSVKGRFTISADTSKNTAYL QMNSLRAEDTAVYYCARRHWPGGFDY WGQGTLVTVSSASTKGPSVFPLAPSSKS TSGGTAALGCLVKDYFPEPVTVSWNSG ALTSGVHTFPAVLQSSGLYSLSSVVTVP SSSLGTQTYICNVNHKPSNTKVDKKVEP KSCDKTHTCPPCPAPELLGGPSVFLFPP | DIQMTQSPSSLSASVGDRVTITCRASQDV STAVAWYQQKPGKAPKLLIYSASFLYSG VPSRFSGSGSGTDFTLTISSLQPEDFATYY CQQYLYHPATFGQGTKVEIKRTVAAPSV FIFPPSDEQLKSGTASVVCLLNNFYPREA KVQWKVDNALQSGNSQESVTEQDSKDS TYSLSSTLTLSKADYEKHKVYACEVTHQ GLSSPVTKSFNRGEC (SEQ ID NO: 61) |

TABLE 3-continued

Heavy and light chains of exemplary antibodies of the invention and of control antibodies described herein

| Antibody | Heavy chain (HC) | Light chain (LC) |
|---|---|---|
|  | KPKDTLMISRTPEVTCVVVDVSHEDPE VKFNWYVDGVEVHNAKTKPREEQYAS TYRVVSVLTVLHQDWLNGKEYKCKVS NKALPAPIEKTISKAKGQPREPQVYTLP PSREEMTKNQVSLTCLVKGFYPSDIAVE WESNGQPENNYKTTPPVLDSDGSFFLY SKLTVDKSRWQQGNVFSCSVMHEALH NHYTQKSLSLSPGK (SEQ ID NO: 60) |  |
| IgG1 | EVRLLESGGGLVQPGGSLRLSCAASGFT FSNYAMGWVRQAPGKGLEWVSAISGS GGSTYYADSVKGRFTTSRDDSKNALYL QMNSLRAEDTAVYYCARGGPGWYAA DVWGQGTTVTVSSASTKGPSVFPLAPSS KSTSGGTAALGCLVKDYFPEPVTVSWN SGALTSGVHTFPAVLQSSGLYSLSSVVT VPSSSLGTQTYICNVNHKPSNTKVDKK AEPKSCDKTHTCPPCPAPELLGGPSVFL FPPKPKDTLMISRTPEVTCVVVDVSHED PEVKFNWYVDGVEVHNAKTKPREEQY NSTYRVVSVLTVLHQDWLNGKEYKCK VSNKALPAPIEKTISKAKGQPREPQVYT LPPSRDELTKNQVSLTCLVKGFYPSDIA VEWESNGQPENNYKTTPPVLDSDGSFF LY SKLTVDKSRWQQGNVFSCSVMHEA LHNHYTQKSLSLSPGK (SEQ ID NO: 62) | DIQMTQSPSSLSASVGDRVTITCRASQSIS SYLNWYQQKPGKAPKLLIYAASLQSGV PSRFSGSGSGTDFTLTISSLQPEDFATYYC QQADLPAFAFGGGTKVEIKRTVAAPSVFI FPPSDEQLKSGTASVVCLLNNFYPREAK VQWKVDNALQSGNSQESVTEQDSKDST YSLSSTLTLSKADYEKHKVYACEVTHQG LSSPVTKSFNRGEC (SEQ ID NO: 63) |
| ADI-31853 | QLQLQESGPGLVKPSETLSLTCTVSGGSI YSESYYWGWIRQPPGKGLEWIGSIVYS GYTYYNPSLKSRVTISVDTSKNQFSLKL SSVTAADTAVYYCARVRTWDAAFDIW GQGTMVTVSSASTKGPSVFPLAPCSRST SESTAALGCLVKDYFPEPVTVSSWNS LTSGVHTFPAVLQSSGLYSLSSVVTVPS SSLGTKTYTCNVDHKPSNTKVDKRVES KYGPPCPPCPAPEAAGGPSVFLFPPKPK DTLMISRTPEVTCVVVDVSQEDPEVQF NWYVDGVEVHNAKTKPREEQFNSTYR VVSVLTVLHQDWLNGKEYKCKVSNKG LPSSIEKTISKAKGQPREPQVYTLPPSQE EMTKNQVSLTCLVKGFYPSDIAVEWES NGQPENNYKTTPPVLDSDGSFFLYSRLT VDKSRWQEGNVFSCSVMHEALHNHYT QKSLSLSLG (SEQ ID NO: 77) | DIQMTQSPSSLSASVGDRVTITCQASQDIS NYLNWYQQKPGKAPKLLIYDASNLETG VPSRFSGSGSGTDFTFTISSLQPEDIATYY CQQVLELPPWTFGGGTKVEIKRTVAAPS VFIFPPSDEQLKSGTASVVCLLNNFYPRE GAAKVQWKVDNALQSGNSQESVTEQDSKD STYSLSSTLTLSKADYEKHKVYACEVTH QGLSSPVTKSFNRGEC (SEQ ID NO: 78) |

TABLE 4

Exemplary heavy and light chain constant regions

| | |
|---|---|
| IgG1 heavy chain constant region | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKKAEPKSCDKTHTCPPC PAPELLGGPSVFLFPPKPKDTLMISRTPEVTCVVVDVSHEDPEVKFNWYVDGVEV HNAKTKPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQPENNYKT TPPVLDSDGSFFLYSKLTVDKSRWQQGNVFSCSVMHEALHNHYTQKSLSLSPGK (SEQ ID NO: 64) |
| IgG1 heavy chain constant region (comprising a N297A mutation at position 297) | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKKVEPKSCDKTHTCPPC PAPELLGGPSVFLFPPKPKDTLMISRTPEVTCVVVDVSHEDPEVKFNWYVDGVEV HNAKTKPREEQYASTYRVVSVLTVLHQDWLNGKEYKCKVSNKALPAPIEKTISK AKGQPREPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLSLSPGK (SEQ ID NO: 65) |

TABLE 4-continued

Exemplary heavy and light chain constant regions

| | |
|---|---|
| IgG4 heavy chain constant region | ASTKGPSVFPLAPCSRSTSESTAALGCLVKDYFPEPVTVSWNSGALTSGVHTFPAV LQSSGLYSLSSVVTVPSSSLGTKTYTCNVDHKPSNTKVDKRVESKYGPPCPPCPAP EAAGGPSVFLFPPKPKDTLMISRTPEVTCVVVDVSQEDPEVQFNWYVDGVEVHN AKTKPREEQFNSTYRVVSVLTVLHQDWLNGKEYKCKVSNKGLPSSIEKTISKAKG QPREPQVYTLPPSQEEMTKNQVSLTCLVKGFYPSDIAVEWESNGQPENNYKTTPP VLDSDGSFFLYSRLTVDKSRWQEGNVFSCSVMHEALHNHYTQKSLSLSLG (SEQ ID NO: 66) |
| κ light chain constant region | RTVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC (SEQ ID NO: 67) |

These and other aspects and embodiments of the invention are described in the drawings (brief description of the drawings follows) and in the following detailed description of the invention and are illustrated in the following examples. Any or all of the features discussed above and throughout the application may be combined in various embodiments of the invention. The following examples further illustrate the invention. However, it is to be understood that the examples are described by way of illustration and not limitation, and various modifications may be made by those skilled in the art.

EXAMPLES

Example 1. Preparation of Hybridoma Cells

A hybridoma technology is a method of fusing two cells while maintaining the main characteristics of both. The two cells refer to an antigen-immunized mouse splenocyte and a mouse myeloma cell. The mouse splenocyte (B lymphocyte) immunized by specific antigen is characterized by antibody secretion functions, but cannot be subcultured in vitro. The mouse myeloma cells can divide and proliferate indefinitely in culture conditions, i.e., are so-called immortalized. In the action of a selective medium, only the hybrid cells formed by fusing the myeloma cells and the B cells may have the capacity of passaging, and a cell clone with both the antibody secretion function and immortality is formed. In an experiment, a mouse was immunized by hPD-L1 protein, and splenocytes and myeloma cells of the mouse were obtained and fused, so that the hybridoma cells capable of expressing positive antibodies were obtained.

Hybridoma Fusion
Experimental Animals and Immunological Information

| | |
|---|---|
| Mouse | Balb/c (Beijing Vital River Laboratory Animal Technology Co., Ltd.) |
| Immunizing antigen | Human PD-L1 protein (extracellular domain), ACRO BIOSYSTEMS, Catalog No. PD1-H5229 |
| Immunizing method | 50 μg/mouse, subcutaneous (SC), 50 μL per spot, 4 spots |
| Times of immunizing | 5 |
| Final booster immunization | 50 μg of PD-L1 protein, intraperitoneal (IP), 3 days before fusion |

Preparation of electroporation: dishes were thoroughly soaked with 70% ethanol and dried in an ultra clean bench for use.

Isolation of splenocytes: the mouse was sacrificed by cervical dislocation, sterilized with 75% alcohol for 5 min, and immediately placed on a mouse dissecting plate in the ultra clean bench, in a left lateral decubitus position, and limbs of the mouse were fixed with No. 7 needles; the spleen was taken out after aseptically opening the abdominal cavity and then washed with basal medium (prepared as per the table below). Surrounding connective tissues were carefully removed. The spleen was then transferred to another dish containing the basal medium; the spleen was pressed with an elbow needle, perforated with a small needle, and then pressed with forceps to fully release the splenocytes so as to obtain splenocyte suspension; after being filtered through a 100-μM cell strainer, the cell suspension was washed once by 30 mL of basal medium and centrifuged at 1200 rpm for 6 min

| Name | Composition | Preparation |
|---|---|---|
| Basal medium | RPMI-1640 (Hyclone) | 90% |
| | FBS (Hyclone) | 10% |
| | GlutaMAX™ Supplement (Gibco) | 1× |

Lysis of erythrocytes: The supernatant was discarded and the cells were resuspended in 10 mL of a RBC lysis buffer (GIBCO). Then 20 mL of a RBC lysis buffer was added; the suspension was left to stand for 5 min and centrifuged at 1100 rpm for 6 min. After removing the supernatant, the cells were resuspended in 10 mL of basal medium. Then 30 mL of basal medium was added, and the cells were centrifuged at 1100 rpm for 6 min; after removal of the supernatant, the cells were resuspended in 20 mL of basal medium and counted.

Electroporation: SP2/0 cells (mouse myeloma cells) (ATCC) were resuspended in 20 mL of basal medium and counted; the SP2/0 cells and the splenocytes were mixed in a ratio of 1:2 to 1:1, and centrifuged at 100 rpm for 6 min; after removal of the supernatant, the mixed cells were resuspended in 10 mL of fusion buffer (BTXpress); then, 15 mL of fusion buffer was added, and the mixture was centrifuged at 1000 rpm for 5 min with the supernatant discarded; after repeating the above steps, the cells were resuspended with an appropriate amount of fusion buffer solution and the mixed cell density was adjusted to $1 \times 10^7$ cells/mL. The settings of the electroporation apparatus were as follows. 2 mL of cell suspension was added into each dish for electroporation.

| Condition | Mouse (SP2/0-ECF-F) |
|---|---|
| Alignment: | 60 v, 30 sec |
| Membrane breaking: | 1500 V, 30 μs, 3× |
| Post-fusion pulse: | 60 V, 3 sec |

Post-fusion plating: The cells were left in the dish at room temperature for 5 min; the cells were transferred to a centrifuge tube and diluted to 1-2×10$^4$ cells/mL with selective medium (prepared as per the following table). 100 μL of cell suspension was added to each well of a 96-well plate. The selective medium was changed 7 days after the fusion. Cells were screened on Day 10 (or later, depending on the cell growth state) of incubation. The hybridoma cells expressing specific anti-PD-L1 antibodies were selected through FACS [FACS ARIA BD Biosciences)].

| Name | Composition | Preparation |
|---|---|---|
| Selective medium | RPMI-1640 (Hyclone) | 90% |
| | FBS (Hyclone) | 10% |
| | HAT medium (Gibco) | 1× |
| | GlutaMAX™ Supplement (Gibco) | 1× |

Positive Hybridoma Cell Subcloning

Subcloning: 200 μL of the basal medium described above was added into each well in the second to eighth columns of a 96-well plate; a suspension was made using the cells from the positive wells selected, and was added into the first column; 100 μL of the cell suspension in the first column was transferred into the second column, and 100 μL of the mixture was transferred into the next column after mixing well. The above step was repeated until a mixture of 300 μL was obtained in the last column. After sitting for 15 min, the cells were counted under a microscope. A corresponding volume containing about 100 cells was added to 20 mL of the basal medium described above for mixing and plating at 200 μL each well. After one week, cells were observed under the microscope. Monoclonal wells were marked, and positive wells were detected.

Cell cryopreservation: The cells were monitored for their states. Those growing well with viability over 90% were centrifuged at 1000 rpm for 5 min and the supernatant was discarded; The cells were resuspended to 1×10$^7$ cells/mL using cryoprotectant (45.5% of FBS, 44.5% of RPMI-1640 and 10% of DMSO), aliquoted into cryopreservation tubes, placed in programmed cooling containers, and cryopreserved at −80° C.

Example 2. Production and Purification of a Chimeric Antibody

Using molecular biotech, the invention produces antibody sequences in the anti-PD-L1 positive hybridoma cells and constructs a human-mouse chimeric antibody using the antibody sequences.

Hybridoma Sequencing

RNA extraction: Fresh cells were centrifuged at 300 g for 5 min, and the supernatant was discarded. 500 μL of LY buffer (Biomiga) (20 μL of betamercaptoethanol per 1 mL prior to use) was added to the precipitate, and was shaken until being clear. The mixture was transferred into a centrifugation tube and centrifuged at 13000 rpm for 2 min. The flow-through was collected. 100% ethanol was added to the flow-through in a ratio of 1/2, and the fluid was mixed for 5 times until a clear solution was obtained. The clear solution was added into an RNA collection tube and centrifuged at 13000 rpm for 1 min, and the liquid portion was discard. 500 μL of recovery buffer (Takara) was added, and the mixture was centrifuged at 13000 rpm for 30 s, and was centrifuged for another 30 s after adding 500 μL of RNA washing buffer (Biomiga) (ethanol is added before use). The above process was repeated before further centrifugation and an evaporation for a complete removal of ethanol. The collection column was pre-treated with 30 μL of DEPC-treated water, and the mixture was centrifuged at 12000 g for 2 min. and the eluates were collected. The RNA concentration was measured.

cDNA Production Through Reverse Transcription:

The reaction system I was configured as follows:

| Name | Amount |
|---|---|
| Oligo dT Primer* | 1 μL |
| dNTP* | 1 μL |
| Template RNA (RNA obtained above) | 5 ug |
| RNase free ddH$_2$O* | Make up to 10 μL |

*Derived from PrimeScript II 1$^{st}$ Strand cDNA Synthesis Kit; purchased from Takara.

After incubation at 65° C. for 5 min, the system was rapidly cooled on ice; to the reaction system I the following reverse transcription system was added in a total amount of 20 μL:

| Name | Amount |
|---|---|
| Reaction system I | 10 μL |
| 5× PrimeScript II Buffer* | 4 μL |
| RNase Inhibitor (40 U/μL)* | 0.5 μL (20 U) |
| PrimeScript II RTase (200 U/μL)* | 1 μL (200 U) |
| RNase free ddH$_2$O* | Make up to 20 μL |

*Derived from PrimeScript II 1$^{st}$ Strand cDNA Synthesis Kit; purchased from Takara.

After slowly mixing, reverse transcription was induced in the following conditions of 42° C. for 60 min→95° C. for 5 min. The mixture was then cooled on ice before cDNA collection.

Connection of cDNA with T Vector:

The heavy chain variable region and light chain variable region were amplified separately through PCR The PCR reaction system comprised h following components:

| Name | Amount |
|---|---|
| TaKaRa EX Tag HS | 0.25 μL |
| Primer Mix 1 (following table 5) | 1 μL |
| Primer Mix 2 (following table 6) | 1 μL |
| cDNA (obtained as mentioned above) | 1 μL |
| 10× Ex Tag buffer | 5 μL |
| dNTP Mixture (2.5 mM each) | 4 μL |
| RNase free ddH$_2$O | Make up to 50 μL |

PCR reaction conditions were as follows:

| | | |
|---|---|---|
| 94° C. | 5 min | |
| 94° C. | 30 s | |
| 55° C. | 30 s | 30 cycles |
| 72° C. | 60 s | |
| 72° C. | 5 min | |

0.5 μL of pMD20-T vector (Clontech) and 5 μL of Ligation Mighty Mix (Takara) were added to 4.5 μL of the PCR product from the PCR reaction. The mixture was gently mixed, and incubated at 37° C. for 2 h to obtain a ligation product.

Transformation of Cells:

TOP10 competent cells [Tiangen Biotech (Beijing) Co., Ltd.] were taken from −80° C. and thawed on ice. 5 μL of the obtained ligation product was added into the thawed TOP10 competent cells. The mixture was shaken and incubated on ice for 30 min. After heat shock at 42° C. for 90 s, the obtained mixture was rapidly cooled on ice in 2 min. 900 µL of LB culture medium [Sangon Biotech (Shanghai) Co., Ltd.] was added into the EP tube, and the mixture was incubated at 37° C. on a shaker at 220 rpm for 1 hour. The bacteria were centrifuged at 3000 g for 2 min. 800 µL of supernatant was removed, and the bacteria were resuspended with the remaining medium for inoculating on an ampicillin plate. The bacteria were incubated overnight at 37° C. Clones were separated for sequencing.

Construction of Chimeric Antibodies

The VH and VL regions, which had been sequenced, of the mouse anti-PD-L1 antibody generated from the hybridomas of Example 1 were amplified by PCR: the sequences of upstream and downstream primers are shown in Tables 5 and 6.

TABLE 5

Primer (Primer Mix 1) for heavy chain variable region (VH) of mouse anti-PD-L1 antibody

| Primer | Sequence (5'-3') | Ratio (%) |
|---|---|---|
| OVH1 | SAGGTCCAGCTGCAGCAGYYTGG (SEQ ID NO: 79) | 28.6 |
| OVH2 | CAGGTRCAGCTGAAGSAGTCAGG (SEQ ID NO: 80) | 10.7 |
| OVH3 | GAKGTGCAGCTTCAGCAGTCRGG (SEQ ID NO: 81) | 8.9 |
| OVH5 | GAVGTGAWGCTGGTGGAGTCTGR (SEQ ID NO: 82) | 7.1 |
| OVH11 | GAAGTGCAGCTGTTGGAGACTGG (SEQ ID NO: 83) | 3.6 |
| OVH14 | GAGGTTCAGCTGCAGCAGTCTGK (SEQ ID NO: 84) | 16.1 |
| OVH15 | CAGGTTCACCTACAACAGTCTGG (SEQ ID NO: 85) | 3.5 |
| REVESE-6 | CTGAGGARACGGTGACCG (SEQ ID NO: 86) | 6 |
| REVESE-4 | CTGAGGAGACTGTGAGAGWGGT (SEQ ID NO: 87) | 4 |
| REVESE-2-1 | CTGAGGAGACGGTGACTGAGGT (SEQ ID NO: 88) | 2 |
| REVESE-2-2 | CTGCAGAGACAGTGACCAGAGT (SEQ ID NO: 89) | 2 |
| Water | | q.s. |

After components were mixed in proportions, the resulting Primer Mix 1 was used for subsequent VH PCR amplification.

TABLE 6

Primer (Primer Mix 2) for light chain variable region (VL) of mouse anti-PD-L1 antibody

| Primer | Sequence (5'-3') | Ratio (%) |
|---|---|---|
| P1 | | A total of ~75 |
| OVK1 | GATGYTKTKVTGACCCAAACTCC (SEQ ID NO: 90) | 21.3 |
| OVK3 | RACATTGTGCTGACMCAATCTCC (SEQ ID NO: 91) | 6.7 |
| OVK4a | SAAAWTGTKCTCWCCCAGTCTCC (SEQ ID NO: 92) | 5.97 |
| OVK4b | SAAAWTCTKCTCWCCCAGTCTCC (SEQ ID NO: 93) | 5.97 |
| OVK4c | SAAAWTTTKCTCWCCCAGTCTCC (SEQ ID NO: 94) | 5.97 |
| OVK6a | ARCATTGTGATGACCCAGWCTCA (SEQ ID NO: 95) | 2.63 |
| OVK6b | ARCATTGTGATGACCCAGWCTCC (SEQ ID NO: 96) | 2.63 |
| OVK6c | GRCATTGTGATGACCCAGWCTCA (SEQ ID NO: 97) | 2.63 |
| OVK6d | GRCATTGTGATGACCCAGWCTCC (SEQ ID NO: 98) | 2.63 |
| OVK10 | GATATCCAGATGACACAGACTAC (SEQ ID NO: 99) | 10.8 |
| OVK14 | GAMATCMWGATGACCCARTCTCC (SEQ ID NO: 100) | 7.7 |
| P2 | | A total of 10 |
| mIGKV1-1 | GATGYTGTGATGACCCAAACTCC (SEQ ID NO: 101) | 1 |
| mIGKV1-2 | GATGTTTTGATGACCCAAACTCC (SEQ ID NO: 102) | 1 |
| mIGKV2-1 | GATATTGTGATGACGCAGGCTGC (SEQ ID NO: 103) | 1 |
| mIGKV2-2 | GATATTGTGATAACCCAGGATGA (SEQ ID NO: 104) | 1 |
| mIGKV4-1 | GAAAATGTGCTCACYCAGTCTCC (SEQ ID NO: 105) | 1 |
| mIGKV5-1 | GACATCTTGCTGACTCAGTCTCC (SEQ ID NO: 106) | 1 |
| mIGKV5-2 | GACATTGTGATGACTCAGTCTCC (SEQ ID NO: 107) | 1 |
| mIGKV9-1 | GACATCCAGATGATTCAGTCTCC (SEQ ID NO: 108) | 1 |
| mIGKV9-2 | GACATCCAGATGACCCAGTCTCC (SEQ ID NO: 109) | 1 |
| mIGKV12-19 | GACATCCAGATGACHCAGTCTCC (SEQ ID NO: 110) | 1 |
| P3 | | A total of 15 |
| IGKV1 | GATGYTKTGATGACCCAAACTCCA (SEQ ID NO: 111) | 6 |
| IGKV2-109 | GATATTGTGATGACGCAGGCTGCA (SEQ ID NO: 112) | 2 |
| IGKV2-112 | GATATTGTGATAACCCAGGATGAA (SEQ ID NO: 113) | 2 |
| IGKV3-7 | GACATTGTGCTAACACAGTCTCCT (SEQ ID NO: 114) | 1 |
| IGKV3-1-5.10 | RACATTGTGCTSACCCAATCTCCA (SEQ ID NO: 115) | 10 |
| IGKV5-48 | GACATCTTGCTGACTCAGTCTCCA (SEQ ID NO: 116) | 1 |
| IGKV6-13 | GACATTGTGATGACCCAGTCTCAA (SEQ ID NO: 117) | 1 |
| IGKV6-32 | AGTATTGTGATGACCCAGACTCCC (SEQ ID NO: 118) | 1 |
| IGKV14 | GACATCMAGATGACMCAGTCTCCA (SEQ ID NO: 119) | 4 |
| IGKV4-51.86 | GAAAATGTGCTCACYCAGTCTCCA (SEQ ID NO: 120) | 1 |
| IGKV7-33 | GACATTGTGATGACTCAGTCTCCA (SEQ ID NO: 121) | 1 |
| IGKV9-123 | GACATCCAGATGATTCAGTCTCCA (SEQ ID NO: 122) | 1 |
| IGKV9-124 | GACATCCAGATGACCCAGTCTCCA (SEQ ID NO: 123) | 1 |
| IGKV10-95 | GATATCCAGATGACACAGACTACT (SEQ ID NO: 124) | 1 |

TABLE 6-continued

Primer (Primer Mix 2) for light chain variable region (VL) of mouse anti-PD-L1 antibody

| Primer | Sequence (5'-3') | Ratio (%) |
|---|---|---|
| IGKV11-125 | GATGTCCAGATGATTCAGTCTCCA (SEQ ID NO: 125) | 1 |
| mK-Rev | TACAGTTGGTGCAGCATCAG (SEQ ID NO: 126) | |

After components were mixed in proportions, the resulting Primer Mix 2 was used for subsequent VL PCR amplification.

The PCR system was as follows:

| Name | Amount |
|---|---|
| 2× Prime STAR HS (Premix) | 25 µL |
| Primer Mix* | 2 µL |
| Plasmid template | 0.5 µL |
| dNTP Mixture (2.5 mM each) | 4 µL |
| RNase free ddH$_2$O | Make up to 50 µL |

*For VH amplification, the Primer Mix 1 was applied; for VL amplification, the Primer Mix 2 was applied.

The gel was cut for recovering the PCR amplification products.

Homologous Recombination:

The homologous recombination system was configured as follows:

| Name | Amount |
|---|---|
| Recovering fragments | 1 µL |
| pTT5 vector | 2 µL |
| 5× Buffer (Takara) | 2 µL |
| Homologous recombination enzyme (Takara) | 1 µL |
| ddH$_2$O | Make up to 10 µL |

After incubation for 30 min at 37° C., a recombinant product was obtained. The TOP10 competent cells were transformed by the recombinant product, and monoclones were separated for sequencing. Clones containing plasmids with correct insertion directions were selected as positive clones, and preserved.

Expression and Purification of Chimeric Antibodies

Plasmids containing the anti-PD-L1 antibody sequence were extracted from the positive clones obtained above.

293F cells (Invitrogen) were passaged according to a desired transfection volume, and the cell density was adjusted to 1.5×10$^6$ cells/mL the day before transfection. The cell density on the day of transfection was approximately 3×10$^6$ cells/mL. An appropriate amount of plasmids was added to F17 culture medium (Gibco, A13835-01) with 1/10 of the final volume as transfection, and mixed. An appropriate amount of polyethylenimine (PEI) (Polysciences, 23966) was added to the mixture (in a ratio of plasmids to PEI=1:3 in the 293F cells), mixed and incubated at room temperature for 10 min, resulting in a DNA/PEI mixture. After being resuspended with the DNA/PEI mixture, the cells were introduced at 36.5° C., 8% CO$_2$. After 24 h, the cells were supplemented with FEED (Sigma) with 2% of the transfection volume, and were incubated at 36.5° C., 8% CO$_2$ at 120 rpm. On Day 6 days of subculture or until a viability fell below 60%, the cells were centrifuged and the supernatant was collected and purified.

The gravity column for purification was dried at 180° C. for 4 hours after being treated with 0.5 M NaOH overnight, resulting in a purification column. Glass containers were washed with distilled water and dried. Before purification, the collected cultures were centrifuged at 4500 rpm for 30 min, and the cells were discarded. The supernatant was filtered through a 0.22 µL filter. Each tube was filled with 1 mL of Protein A and equilibrated with 10 mL of binding buffer (sodium phosphate 20 mM, NaCl 150 mM, pH 7.0). The filtered supernatant was loaded to the purification column, which was then re-equilibrated with 15 mL of binding buffer. 5 mL of eluent buffer (citric acid+sodium citrate 0.1 M. pH 3.5) was added. The eluate was collected, and 80 µL of Tris-HCl was added per mL of eluate. The buffer of the collected antibodies were changed into PBS (Gibco, 70011-044) by ultrafiltration/diafiltration, and the concentrations were measured.

The amino acid sequences of the CDRs, the light and heavy chain variable regions, and the light and heavy chains of the obtained 4 chimeric antibodies of the invention, and their sequence numbers are shown in Tables 1 to 3 above.

The reference antibody used in the invention is Roche's PD-L1 antibodies Atezolizumab (hereinafter referred to as ATE or Ate, or the trade name: Tecentriq), of which the amino acid sequences of the CDRs, the light and heavy chain variable regions, and the light and heavy chains are also shown in Tables 1 to 3 above.

Example 3. Binding Kinetics of Chimeric Antibodies for Antigens as Determined by Biological Optical Interferometry The equilibrium dissociation constant ($K_D$) for binding of the antibody of the invention to human PD-L1 was determined by biological optical interferometry (ForteBio). A ForteBio affinity assay of prior art was performed (Estep, P., et al, High throughput solution based measurement of antibody-antigen affinity and epitope binning. MAbs, 2013.5 (2):270-8).

Half an hour before the experiment, an appropriate number of AMQ (Pall, 1506091) (for sample detection) or AHQ (Pall, 1502051) (for positive control detection) sensors depending on the number of samples were soaked in SD buffer (PBS 1×, BSA 0.1%, Tween-20 0.05%).

SD buffer, antibodies, and antigens (including human PD-L1, mouse PD-L1 and *Macaca fascicularis* PD-L1, all purchased from Acrobiosystems) each of 100 µL were added to %-well black polystyrene half area microplates (Greiner, 675076). The sensors were arranged according to the positions of the samples. The instrument settings were as follows: the operation procedures were Baseline, Loading ~1 nm. Baseline, Association, and Dissociation. The run time of each procedure was dependent on the rates of association and dissociation. The rotation speed was 400 rpm, and the temperature was 30° C. The $K_D$ values were analyzed by ForteBio analysis software.

In the assay described above, the affinities of antibodies 3-266.1, 4-79.2, 4-26.6, and 4-48.5 are shown in Table 7:

TABLE 7

Affinity constants (equilibrium dissociation constants) for bindings of antigens and antibodies by ForteBio assay

| Antibody | $K_D$ (M) |
|---|---|
| 3-266.1 | 9.80E−10 |
| 4-79.2 | 7.56E−09 |
| 4-26.6 | 3.85E−09 |

TABLE 7-continued

Affinity constants (equilibrium dissociation constants) for bindings of antigens and antibodies by ForteBio assay

| Antibody | $K_D$ (M) |
|---|---|
| 4-48.5 | 1.23E−09 |
| ATE | 2.94E−09 |

In the above assay, the $K_D$ values of the chimeric antibodies 3-266.1, 4-79.2, 4-26.6, and 4-48.5 were 9.80E$^{-10}$ M, 7.56E$^{-09}$ M, 3.85E$^{-09}$ M, and 1.23E$^{-09}$ M respectively. The antibodies in this study had similar or superior $K_D$ values as compared with the reference.

Example 4. Binding Assays of Chimeric Antibodies and Cells Overexpressing PD-L1

In this study, the binding of chimeric antibodies, diluted in gradient, of the invention to stable CHO cell lines overexpressed human PD-L1 on cell surface were measured by flow cytometry.

The CHO cells (CHO-PDL1) overexpressing human PD-L1 were generated by transfecting CHO-S cells (Invitrogen, ExpiCHO™ Expression System Kit, Catalog No. A29133) with pCHO1.0 vectors (Invitrogen) carrying human PD-L1 cDNA (Sino biological) cloned into multiple cloning sites (MCSs).

CHO-PDL1 cells were counted, diluted to 1×10$^6$ cells/mL, and added to each well of a U-shaped bottom 96-well plates at 100 μL/well. The suspension was centrifuged at 400 g for 5 min, and the supernatant was discarded. The samples (chimeric antibodies 3-266.1, 4-79.2, 4-26.6 and 4-48.5 respectively, and the positive control Ate) (the antibodies were serially three-fold diluted from a concentration of 500 nM in PBS containing 0.1% bovine serum albumin (BSA) until the 8th concentration) were added into the U-shaped plates. The cells were resuspended to a volume of 100 μL/well, and then left on ice for 30 min. The suspension was centrifuged at 400 g for 5 min, and the supernatant was discarded. The cells were washed once with PBS. The mixture was centrifuged at 400 g for 5 min, and the supernatant was discarded. 100 μL of FITC-labeled secondary antibody for anti-mouse-Fab (Jackson immuno Research) (diluted in PBS in 1:500) was added per well, and 100 μL of FITC-labeled secondary antibody for anti-human-Fab (Jackson Immuno Research) was added to the cells to which the positive control antibody was added. The cells were incubated for 30 min on ice in the dark. The cells were centrifuged at 400 g for 5 min with the supernatant being discarded, and were washed once with a PBS. The cells were resuspended with 100 μL of 1×PBS, and detected by FACS.

In the assay described above, the binding of antibodies 3-266.1, 4-79.2, 4-26.6 and 4-48.5 to the CHO-PDL1 cells are shown in FIG. 1.

In the assay above, the antibodies 3-266.1, 4-79.2, 4-26.6, and 448.5 all bound to human PD-L1 overexpressed on the CHO cells, and EC$_{50}$ was 2.139 nM, 2.598 nM, 1.985 nM, and 1.995 nM respectively. Compared with the reference antibody ATE, the antibodies 3-266.1, 4-79.2, 4-26.6, and 4-48.5 have superior affinities, and the binding capacities of some antibodies were more than twice of the reference antibody.

Example 5. Humanization of Chimeric Antibodies

The chimeric antibodies obtained in Example 1 were humanized. The antibody humanization was performed by using a SmrtMolHumanize proprietary software program from Macromoltek. The sequences were input into software, and the system generated three-dimensional models of the sequences. The sequences were then humanized via the following steps:
1) determining the structure of CDR loops;
2) searching a human germline sequence database for closest homologous sequences for each V/J region of the heavy and light chains;
3) screening for the human germline which is most similar with the heavy and light chains and has the minimum amount of back mutation;
4) constructing the CDR regions of the chimeric antibody onto the back bone of a human antibody;
5) determining the positions of amino acids that maintain the CDR functions in the back bone based on the sequences and structural features;
6) adding back mutation (back to the input amino acids) at important positions of the sequence;
7) generating the three-dimensional model of the humanized sequence;
8) manually examining the sequence and the structure to identify risk sites that may cause misfolding or reduced stability;
9) optimizing amino acids at risk sites.

The amino acid sequences of the CDRs, the light and heavy chain variable regions, and the light and heavy chains of the obtained 4 chimeric antibodies of the invention (HZ3266-IgG1N297A, HZ3266-IgG1, HZ3266-IgG4PAK, and HZ4485-IgG1N297A) are shown in Tables 1 to 3 above.

Example 6. Binding Kinetics of Humanized Antibodies for Antigens as Determined by ForteBio The equilibrium dissociation constant ($K_D$) binding of the humanized antibodies of different Fc subtypes of the invention to human PD-L1 was determined by ForteBio. The ForteBio affinity assay was shown in Example 2. In the assay described above, the affinities of antibodies HZ3266-IgG1N297A, HZ3266-IgG1, HZ3266-IgG4PAK, and HZ4485-IgG1N297A are shown in Table 8:

TABLE 8

Affinity constants for bindings of antigens and antibodies by ForteBio assay

| Antibody | $K_D$ (M) |
|---|---|
| ATE | 1.62E−09 |
| HZ3266-IgG1N297A | 7.24E−10 |
| HZ3266-IgG1 | 9.35E−10 |
| HZ3266-G4PAAK | 1.32E−09 |
| HZ4485-IgG1N297A | 3.17E−09 |

In the above assay, the humanized antibodies HZ3266-IgG1N297A, HZ3266-IgG1, HZ3266-G4PAAK and HZ4485-IgG1N297A described herein had $K_D$ values of 7.24E$^{-10}$ M, 9.35E$^{-10}$ M, 1.32E$^{-09}$ M, and 3.17E$^{-09}$M respectively, and the humanized antibodies in this study have similar or superior $K_D$ values compared to that of the reference.

Example 7. Binding Assays of Humanized Antibodies and Cells Overexpressing PD-L1

Figure 2:
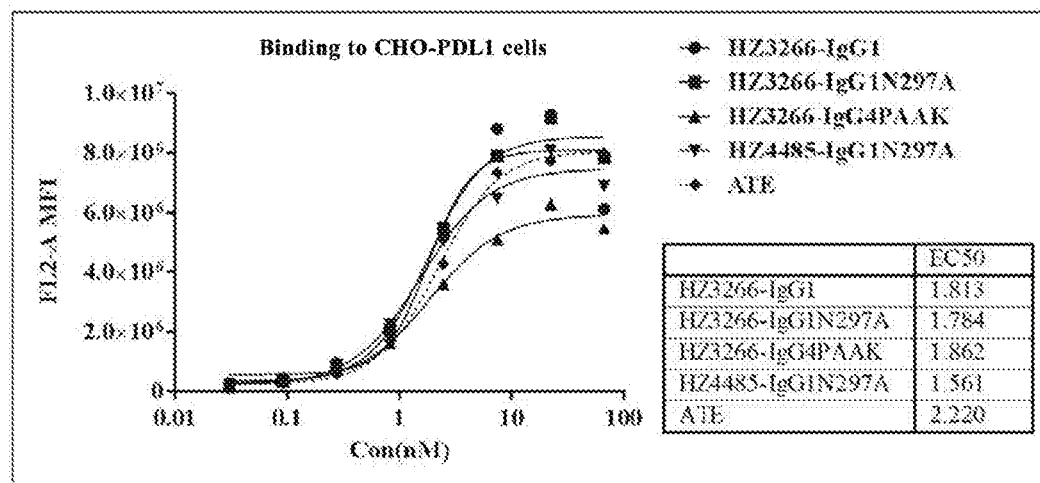
FIG. 2 shows the binding of the anti-PD-L1 antibody of the invention to CHO-PDL1 cells determined by FACS.

In this study, the binding of humanized antibodies, diluted in gradient, of the invention to stable CHO cell lines overexpressed human PD-L1 on cell surface (CHO-PDL1)

were measured by flow cytometry. The assay was shown in Example 3, with exception that the antibodies used were the humanized antibodies HZ3266-IgG1N297A, HZ3266-IgG1, HZ3266-G4PAAK, and HZ4485-IgG1N297A. The antibodies were serially three-fold diluted from a concentration of 500 nM in PBS containing 0.1% bovine serum albumin (BSA) until the 8th concentration. The binding conditions of the humanized antibodies HZ3266-IgG1N297A, HZ3266-IgG1, HZ3266-G4PAAK, HZ4485-IgG1N297A, and CHO-PDL1 are shown in FIG. 2.

In the assay, the humanized antibodies HZ3266-IgG1, HZ3266-IgG1N297A, HZ3266-G4PAAK, and HZ4485-IgG1N297A bound to human PD-L1 over-expressed on the CHO cells, and the EC50 was 1.813 nM, 1.784 nM, 1.862 nM, and 1.561 nM respectively. Compared with the reference antibodies ATE, these antibodies had superior binding capacities.

Example 8. Detection of Biological Activity of Antibodies by MOA

Anti-PD-1/PD-L1 antibodies can relieve the inhibitory effect on a downstream NFAT signal path by blocking the binding of PD-1 and PD-L1. In this study, a MOA detection system (PD-1/PD-L1 Blockade Bioassay, Cell Propagation Model, Catalog J1252) available from Promega, Inc. was utilized. According to the method provided in the product manual, the activation of NFAT signal was reflected by detecting the expression of fluorescent reporter genes, thereby detecting the inhibitory effects of the antibodies on PD-1 and PD-L1 binding.

CHOK1-PDL1 cells (from the MOA detection system described above) were plated one day before the activity assay. The cells were passaged 1 to 2 days before plating. The culture supernatant was discarded and the cells were washed once with PBS (Gibco). An appropriate amount of Trypsin (Gibco) was added for digestion for 3-5 min at 37° C., 5% $CO_2$; culture medium of a volume 4 times that of Trypsin was added, and the cells were transferred to 50-mL centrifuge tubes and counted. Cells of a desired volume were centrifuged at 230 g for 10 min. The cells were added in 1640 culture medium (Gibco) and were resuspended to $4 \times 10^5$ cells/mL. The cells were added to 6-well white culture plates (Nunclon) at 100 μL/well. PBS was added into edge wells at 200 μL/well. The cells were incubated overnight in an incubator at 37° C., 5% $CO_2$.

Jurkat-PD1 cell (from the MOA detection system described above) treatment: Cells were passaged two days before the activity assay. After counting, the cells of a desired volume were centrifuged at 170 g for 5 min; The cells were resuspended to $1.25 \times 10^6$ cells/mL with assay buffer [1640 culture medium (Gibco)+1% FBS].

Addition of samples and Jurkat-PD1 cells to assay plates (from the MOA detection system described above): 95 μL/well of CHOK1-PDL1 cell supernatant was discarded. 40 μL of the samples [the humanized antibodies HZ3266-IgG1, HZ3266-IgG1N297A and HZ4485-IgG1N297A prepared in the invention, the positive control (Ate) and negative control (IgG1)] were added [the antibodies were serially three-fold diluted from a concentration of 100 nM in assay buffer until the 8th concentration]. 40 μL of the Jurkat-PD1 cells were added. The cells were incubated in an incubator at 37° C. 5% $CO_2$ for 6 h.

Detection: The Bio-Glo™ buffer (from the MOA detection system described above) was thawed in advance, and the Bio-Glo™ substrate (from the MOA detection system described above) was added and mixed well. After 6 hours, the Bio-Glo™ reagent (from the MOA detection system described above) was added at 80 μL/well. The resulting mixture was left at room temperature for 5-10 mm before reading.

Figure 3:
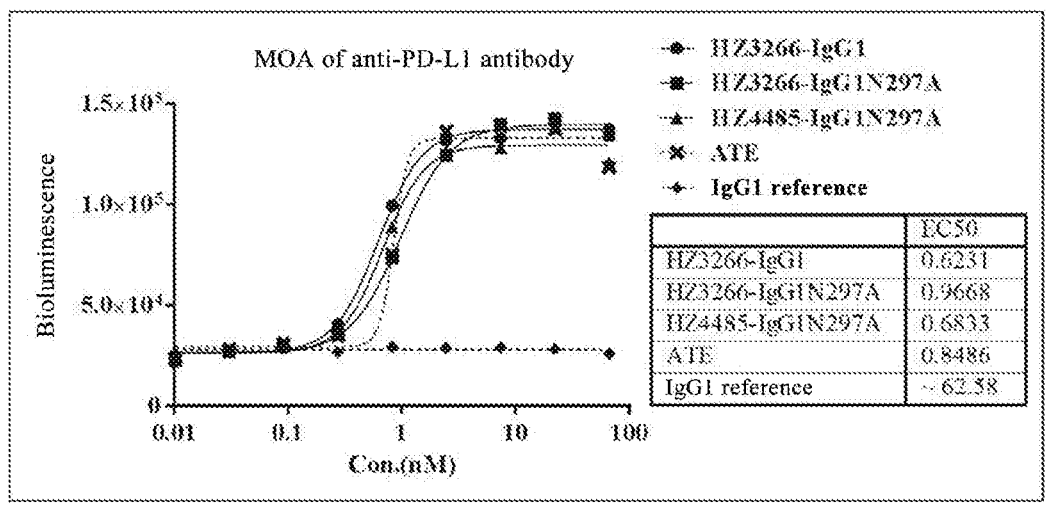
FIG. 3 shows the blocking activity of the antibody of the invention against the PD-1/PD-L1 interaction determined by MOA assay.

In this assay, as shown in FIG. 3, the antibodies HZ3266-IgG1, HZ3266-IgG1N297A, and HZ4485-IgG1N297A can effectively block the PD I/PD-L1 interaction.

Example 9. Mixed Lymphocyte Reaction

In this study, the antibodies and mature DC cells and CD4+T cells derived from different donors were co-incubated. The relative expression quantities of IL2 and IFN-γ in the system were detected, so that the activating effect of different antibodies on T cells was reflected.

PBMC isolation: 2.5-fold PBS was added into 50 mL of fresh blood from a donor. The mixture was gently added to FiColl (Thermo) and aliquoted into 4 tubes with 12.5 mL each tube. The samples were centrifuged at 400 g for 30 min before stopping at a deceleration of 0. The intermediate white strip was pipetted into PBS and washed twice with PBS.

DC cell isolation: The PBMC cells isolated above were incubated adherently for 2 hours at 37° C., 6% $CO_2$ after adding 5 mL of T cell culture medium (prepared as per the following table). The cell suspension was pipetted for CD4+ cell isolation. 3 mL of DC culture medium (prepared as per the following table) was added to remaining cells for a 2-day incubation, and another 3 mL of DC culture medium was added. On Day 5 of culture, rTNFa (R&D Systems) (1000 U/mL), IL-1b (R&D Systems) (5 ng/mL). IL-6 (R&D Systems) (10 ng/mL) and 1 μM PGE2 (Tocris) were added for another incubation of 2 days, resulting in DC cells for lymphocyte mix reaction (MLR).

| Name | Composition | Preparation |
| --- | --- | --- |
| T cell culture medium: | X-VIVO 15 (Lonza) | 93% |
| | Human AB serum | 5% |
| | Na-Pyr (Gibco) | 1% |
| | NEAA (Gibco) | 1% |
| | P/S (Gibco) | 1% |
| | Glutamax (Gibco) | 1% |
| DC cell culture medium | X-VIVO 15 (Lonza) | 99% |
| | Human AB serum | 1% |
| | HEPES (Sigma) | 10 mM |
| | β-Me (Sigma) | 50 μM |
| | IL-4 (R&D Systems) | (1000 U/mL) |
| | GM-CSF (R&D Systems) | (1000 U/mL) |

CD4+ T cell isolation: This was performed according to the 'Untouched CD4+ T cell isolation' kit instructions (11346D, Invitrogen). PBMCs were left for 2 h before the cell suspension was pipetted into a 15-mL centrifugation tube. The cells were centrifuged at 200 g for 10 min, and the precipitate was resuspended with 500 μL of a separating medium, 100 μL of AB type serum and 100 μL of purified antibody. The mixture was incubated for 20 min at 4° C., and washed once with the separating medium. 500 μL of a Bead Buffer (Invitrogen) was added for an incubation of 15 min, and the beads were then removed by a magnetic field. The mixture was washed once with T cell culture medium, and resuspended with 8 mL of culture medium. The resulting mixture was then incubated at 37° C., 6% $CO_2$.

MLR: The matured DC cells obtained above were mixed with CD4+ cells at 200 μL per well, with 10000 DC cells and 100000 CD4+ cells. The antibodies (concentrations: 100 nM, 20 nM, 4 nM, 0.8 nM, 0.16 nM and 0.032 nM) of the invention were added. A mixture of the DC cells prepared above (represented as DC in the following table), CD4+ T cells (represented as CD4 in the following table), the mixture (represented as Cell in the following table) of DC cells and CD4+ cells and IgG1 disclosed in Table 3 herein served as the negative control, and DC+CD4+ T cells+anti-CD3/CD28 magnetic beads (QIAGEN) (represented as Beads in the following table) served as the positive control. The samples were incubated for 5 days, and the concentrations of IL2 and IFN-gamma (the relative expression in DeltaF %) were detected by cisbio kits (Human IL2 Kit 1000 Test, Human IFN gamma 1000 Test).

Figure 4A:
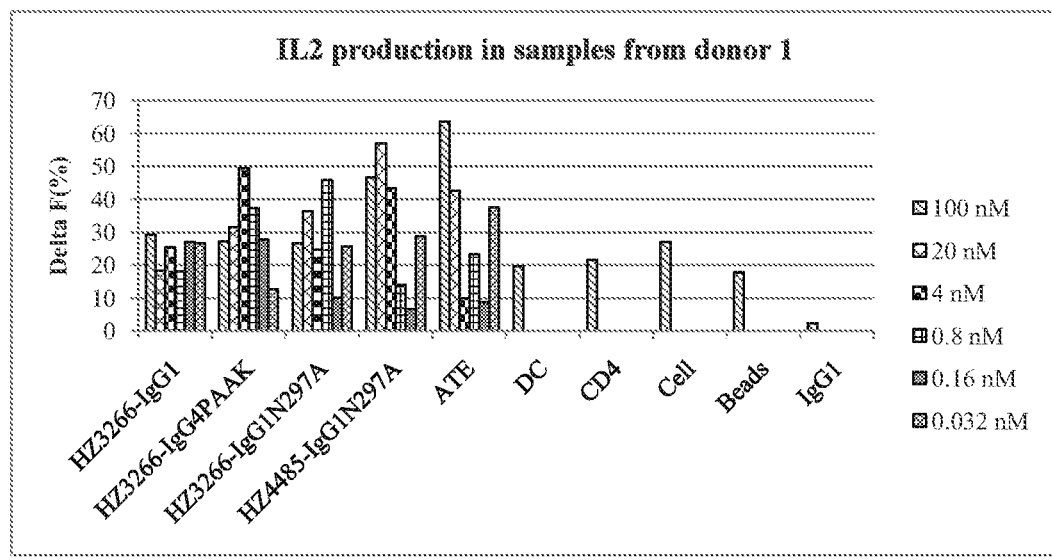
FIGS. 4A and 4B show the activation of T cells (relative expression of IL-2) by the antibody of the invention determined by MLR assay.
Figure 4B:
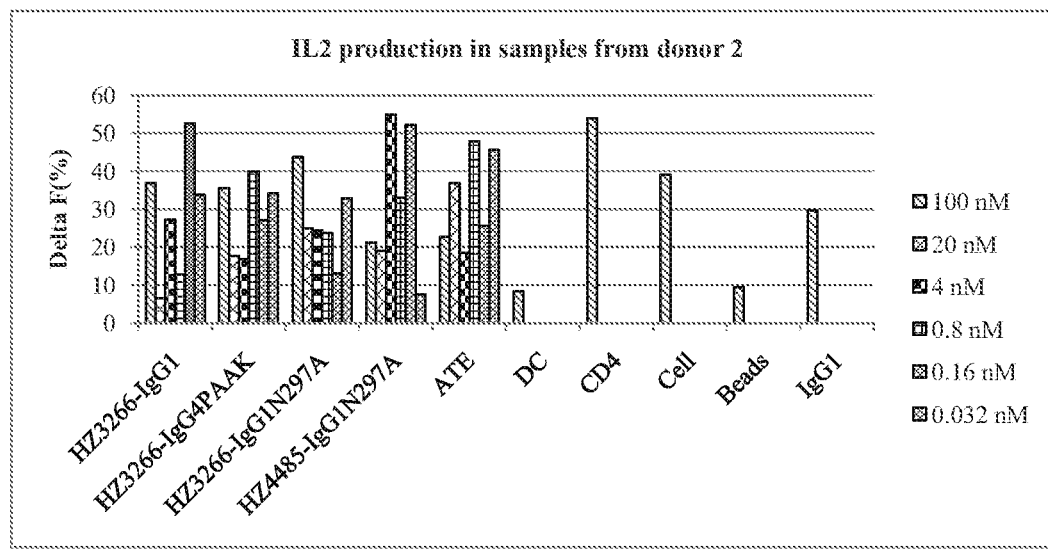
Figure 5A:
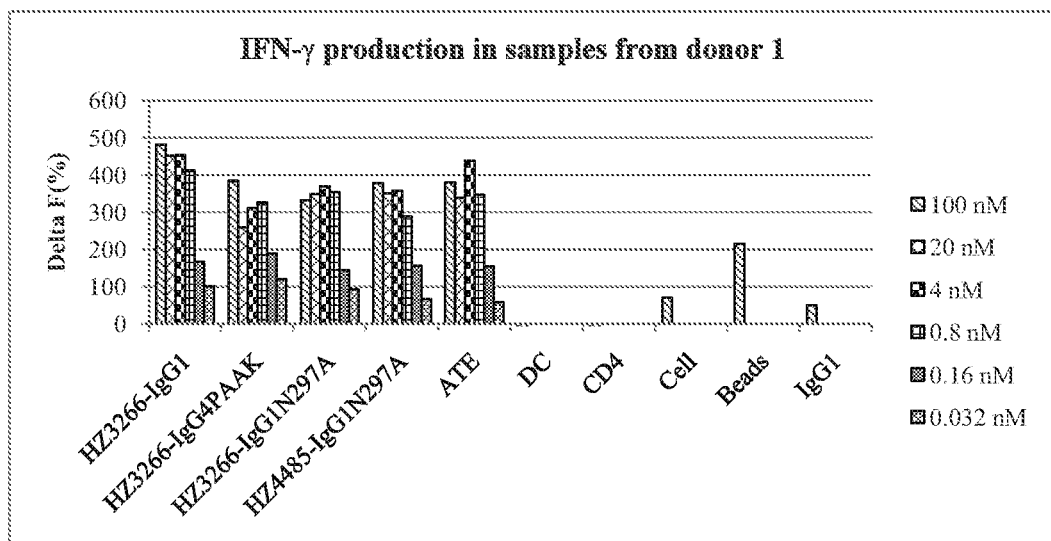
FIGS. 5A and 5B show the activation of T cells (relative expression of IFN-γ) by the antibody of the invention determined by MLR assay.
Figure 5B:
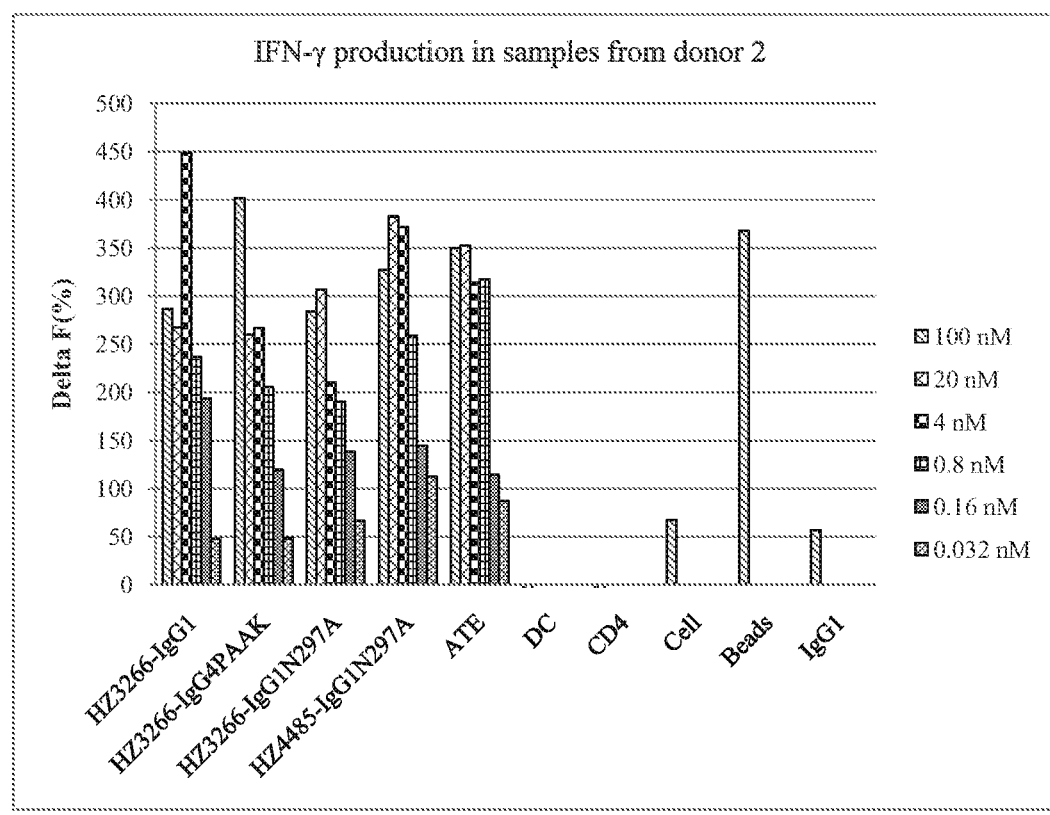

The results are shown in Tables 9, 10, 11, and 12, and FIGS. 4 and 5. Data in the tables are in DeltaF %.

TABLE 9

Relative expression of IL2 in cells from donor 1

| Name | 100 nM | 20 nM | 4 nM | 0.8 nM | 0.16 nM | 0.032 nM |
|---|---|---|---|---|---|---|
| HZ3266-IgG1 | 29.21 | 18.35 | 25.44 | 18.19 | 27.15 | 26.75 |
| HZ3266-IgG4PAAK | 27.23 | 31.54 | 49.54 | 37.47 | 27.76 | 12.7 |
| HZ3266-IgG1N297A | 26.68 | 36.48 | 24.78 | 45.85 | 10.09 | 25.71 |
| HZ4485-IgG1N297A | 46.79 | 57.07 | 43.51 | 14.1 | 6.655 | 28.83 |
| ATE | 63.66 | 42.66 | 9.989 | 23.34 | 8.729 | 37.55 |
| DC | 19.71* | | | | | |
| CD4 | 21.67* | | | | | |
| Cell | 27.17* | | | | | |
| Beads | 17.85 | | | | | |
| IgG1 | 2.47 | | | | | |

*Negative control; no antibodies or magnetic beads were added.

TABLE 10

Relative expression of IL2 in cells from donor 2

| Name | 100 nM | 20 nM | 4 nM | 0.8 nM | 0.16 nM | 0.032 nM |
|---|---|---|---|---|---|---|
| HZ3266-IgG1 | 36.91 | 6.659 | 27.29 | 12.83 | 52.58 | 33.79 |
| HZ3266-IgG4PAAK | 35.59 | 17.76 | 16.9 | 40.03 | 27.13 | 34.2 |
| HZ3266-IgG1N297A | 43.74 | 25.01 | 24.49 | 23.83 | 13.2 | 32.88 |
| HZ4485-IgG1N297A | 21.29 | 19.11 | 54.91 | 33.08 | 52.22 | 7.629 |
| ATE | 22.68 | 36.87 | 18.62 | 47.91 | 25.62 | 45.62 |
| DC | 8.379* | | | | | |
| CD4 | 53.96* | | | | | |
| Cell | 39.05* | | | | | |
| Beads | 9.422 | | | | | |
| IgG1 | 29.71 | | | | | |

*Negative control; no antibodies or magnetic beads were added.

TABLE 11

Relative expression of IFN-γ in cells from donor 1

| Name | 100 nM | 20 nM | 4 nM | 0.8 nM | 0.16 nM | 0.032 nM |
|---|---|---|---|---|---|---|
| HZ3266-IgG1 | 482.7 | 452.4 | 453.5 | 412.3 | 166.3 | 101.1 |
| HZ3266-IgG4PAAK | 384.7 | 259.3 | 310.8 | 326.7 | 188.9 | 120.9 |
| HZ3266-IgG1N297A | 332.1 | 349.5 | 369.7 | 354.5 | 143.7 | 92.12 |
| HZ4485-IgG1N297A | 379 | 350.3 | 357.5 | 288.3 | 156.6 | 66.73 |

TABLE 11-continued

Relative expression of IFN-γ in cells from donor 1

| Name | 100 nM | 20 nM | 4 nM | 0.8 nM | 0.16 nM | 0.032 nM |
|---|---|---|---|---|---|---|
| ATE | 380.1 | 338.4 | 438.8 | 348.3 | 155.1 | 58.48 |
| DC | −18.8* | | | | | |
| CD4 | −14.6* | | | | | |
| MLR Cell | 69.89* | | | | | |
| Beads | 215.1 | | | | | |
| IgG1 | 49.66 | | | | | |

*Negative control; no antibodies or magnetic beads were added.

TABLE 12

Relative expression of IFN-γ in cells from donor 2

| Name | 100 nM | 20 nM | 4 nM | 0.8 nM | 0.16 nM | 0.032 nM |
|---|---|---|---|---|---|---|
| HZ3266-IgG1 | 286.7 | 267.3 | 449.1 | 236.7 | 194 | 48.33 |
| HZ3266-IgG4PAAK | 402.1 | 260.2 | 266.7 | 205.4 | 119.6 | 48.5 |
| HZ3266-IgG1N297A | 284.2 | 306.8 | 210.5 | 190.1 | 138.3 | 66.4 |
| HZ4485-IgG1N297A | 327 | 382.9 | 371.9 | 258.7 | 144.7 | 112.7 |
| ATE | 349.8 | 352.4 | 314.1 | 317.6 | 114.5 | 87.25 |
| DC | 4.12* | | | | | |
| CD4 | −7.17* | | | | | |
| Cell | 67.53* | | | | | |
| Beads | 367.8 | | | | | |
| IgG1 | 57.15 | | | | | |

*Negative control; no antibodies or magnetic beads were added.

Therefore, the antibodies of the invention can effectively activate T cells in vitro, and part of the activation effects are superior to those of positive control antibody.

Example 10. Assay of Antibody Druggability by Zenix Column

In this assay, the antibody druggability was detected by analyzing the retention time of the exemplary humanized antibodies of the invention in Zenix columns (Sepax Technologies, Inc). The shorter the retention time was, the lower the antibody viscosity was, and the better the drugability was.

Chromatographic conditions: wavelength: 214 nm, column temperature: 25° C., flow rate: 0.35 mL/min, injection volume: 10 μL.

Sample preparation: 100 μL of samples (antibodies HZ3266-IgG1, HZ3266-IgG4PAAK, HZ3266-IgG1N297A, and HZ4485-IgG1N297A; ATE as a positive control with a concentration of 1 mg/mL) was centrifuged at 13000 rpm for 5 min. 80 μL of the supernatant was transferred into a liquid-phase insert and placed on a liquid-phase sample tray for injection.

As shown in Table 13, the retention times of different HZ3266 isotypes and HZ4485 on the column were shorter than that of the reference antibody, indicating that good druggability of the antibodies HZ3266 and HZ4485.

TABLE 13

Assay of antibody druggability by Zenix column

| Sample | Retention time (RT) (min) |
|---|---|
| HZ3266-IgG1 | 7.744 |
| HZ3266-IgG4PAAK | 7.73 |
| HZ3266-IgG1N297A | 7.749 |

TABLE 13-continued

Assay of antibody druggability by Zenix column

| Sample | Retention time (RT) (min) |
|---|---|
| HZ4485-IgG1N297A | 8.429 |
| ATE | 10.317 |

Example 11. Anti-Tumor Efficacy Assay

In this assay, the anti-tumor effect of the PD-L1 antibody of the invention was tested in MC38 cells (MC38-hPDL1) (Nanjing Yinhe Biotech) expressing human PD-L1 in hPD-L1 transgenic mice.

hPD-L1 Transgenic Mice:

Female hPD-L1 transgenic mice with C57Bl/6 background (about eight weeks old), purchased from Shanghai Model Organisms Center, Inc. Before the study, the mice were adapted for 7 days after arrival.

Cells:

The MC38 cells (MC38-hPDL1) expressing human PD-L1 were purchased from Nanjing Yinhe Biotech. and were subcultured in strict accordance to the instruction for further in-vivo assays. The cells were collected by centrifugation and resuspended in sterile PBS, with the cell density adjusted to 5-$10^6$ cells/mL. On the Day 0, 0.2 mL of cell suspension was subcutaneously grafted to the abdominal region of the hPD-L1 transgenic mice to establish MC38-hPDL1 tumor-bearing mouse models.

Administration:

The tumor volume of the mice was measured 6 days after grafting, and mice with the tumor volume ranging from 87.4 $mm^3$ to 228.4 $mm^3$ were selected and evenly divided into groups by tumor volume (8 mice each group, one receiving IgG1 and the other receiving HZ3266-IgG1N297A of the invention). Mice were treated twice a week at 6, 10, 14, 17, 21, 24, 28, 31 and 35 days after grafting. Dosages and route of administration are shown in Table 12. Changes in tumor volume and body weight of mice were monitored during the treatment period twice/week for 5 weeks. Body weights and tumor volumes were measured prior to each dose. Tumor volume measurement: The maximum length of major axis (L) and maximum length of minor axis (W) of tumors were measured with a vernier caliper, and tumor volume was calculated using the following formula: $V=L \times W^2/2$. The mice were weighted twice a week using an electronic balance.

TABLE 14

Study design

| Group | Dose | Dosing volume | Concentration | Route of administration |
|---|---|---|---|---|
| IgG1 (sequence shown in Table 3) | 20 mg/kg | 10 mL/kg | 2.0 mg/mL | Intraperitoneal |
| Antibody of the invention | 20 mg/kg | 10 mL/kg | 2.0 mg/mL | Intraperitoneal |

Figure 6:
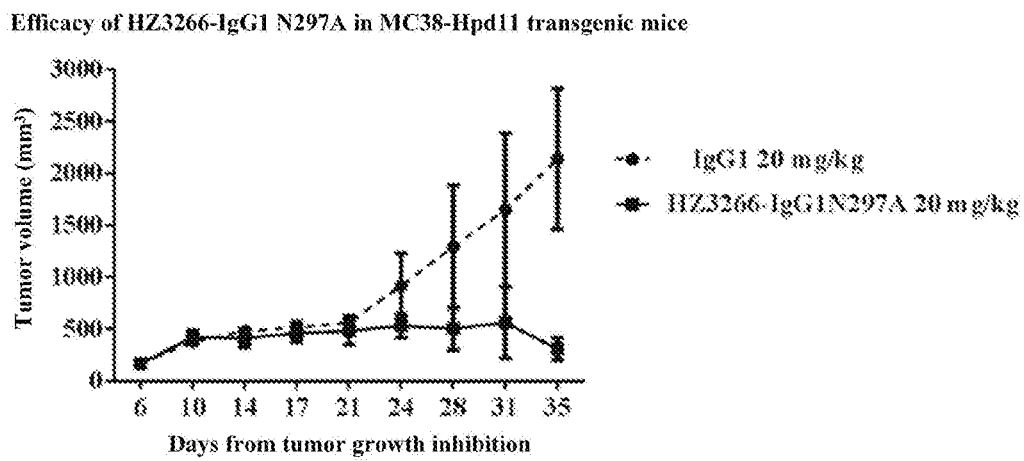
FIG. 6 shows the inhibitory effect of the antibody of the invention on tumors.

The antibodies of the invention showed a significant anti-tumor efficacy at one week after administration (FIG. 6), and by Day 35, the tumor in one mouse receiving the antibody of the invention was completely regressed. The results showed that different antibody dosages had no effect on the body weight of the tumor-bearing mice.

Therefore, the antibody of the invention has obvious inhibitory effect on tumors.

Example 12. Combination of Anti-PD-L1 Antibody of the Invention with Anti-Human-LAG-3 Antibody In this study, the anti-tumor activity the combined use of the anti-PD-L1 antibody (HZ3266-IgG1N297A) and the anti-human-LAG-3 antibody (ADI-31853) was tested in a humanized mouse model.

In this study, the anti-tumor efficacy of the anti-PD-L1 antibody was tested in NCG mice bearing A375 (ATCC) human skin cancer cells. Human PBMCs (All Cells) ($2 \times 10^6$ cell/mouse) were intravenously injected in advance, and then A375 tumor-bearing mouse models were established through subcutaneous grafting. The mice were grouped after tumor formation and treatments with different antibodies were given. The changes in tumor size and body weight of mice were monitored during the treatment period. The treatments were given twice a week for 2 weeks with a total of 5 doses. The mice were monitored twice a week for 4 weeks. Dosages and route of administration are as follows. The tumor growth inhibition (TGI %) was calculated after the end of treatment.

Anti-Human-LAG-3 Antibody ADI-31853 cDNA encoding the light and heavy chain amino acid sequences (Table 3) of the anti-LAG-3 antibody ADI-31853 was cloned into an expression vector pTT5, according to a conventional method in the art.

The expression vector containing target antibody genes and a transfection reagent PEI (Polysciences) were transiently transfected into incubated human embryonic kidney cells 293 (Invitrogen) according to a scheme provided by the manufacturer. After transfection, the supernatant was discarded and the cells were diluted to $4 \times 10^6$/mL with fresh EXP1293 medium (Gibco). The cells were incubated at 37° C., 5% $CO_2$ for 7 days, with fresh medium fed every 48 hours. After 7 days, the cells were centrifuged at 1300 rpm for 20 min. The supernatant was purified with Protein A to produce antibodies with purity greater than 95%.

The equilibrium dissociation constant ($K_D$) for binding of ADI31853 to human LAG-3 (hLAG-3) was measured by biological optical interferometry (ForteBio). A ForteBio affinity assay of prior art was performed (Estep. P., et al, High throughput solution based measurement of antibody-antigen affinity and epitope binning. MAbs, 2013.5(2):270-8). Briefly, the sensor was equilibrated offline in assay buffer for 30 minutes, and on-line detection was then conducted for 60 seconds to establish a baseline. The purified antibody obtained as described above was loaded on-line onto an AHQ sensor (ForteBio) for ForteBio affinity assay. The sensor with the loaded antibody was then exposed to 100 nM of a human LAG-3 antigen (ArcoBiosystems) for 5 minutes before transferring the sensor to the assay buffer for dissociation for 5 minutes for dissociation rate measurement. Kinetic analysis was performed using a 1:1 binding model.

In the assay described above, the ADI-31853 affinity was as follows:

| Antibody | The antibody was on an AHQ tip, and the human LAG-3-His was in solution (100 nM) [the univalent affinity, the equilibrium dissociation constant $K_D$ (M)] | Association constant ($M^{-1}S^{-1}$) | Dissociation constant ($S^{-1}$) |
|---|---|---|---|
| ADI-31853 | $6.22E4^{-10}$ | $3.22E^{+05}$ | $2.00E^{-04}$ |

Mice:

NOG mice, female, 7-8 weeks old (ages at tumor cell grafting), weight of 17.6-24.2 g, purchased from Beijing Vital River Laboratory Animal Technology Co., Ltd. Before the study, the mice were adapted for 7 days after arrival.

Cells:

The human skin cancer cells A375 (ATCC #CRL-1619) were purchased from ATCC and were subcultured in strict accordance to the requirement provided by ATCC for further in-vivo assays. The cells were collected by centrifugation and resuspended in sterile PBS, with the cell density adjusted to $30 \times 10^6$ cells/mL. The NOG mice were intravenously injected with human PBMC (All Cells), followed by right dorsal shaving and subcutaneous injections of the A375 cells at 0.2 mL/mouse. The tumor volume of the mice was measured 7 days after grafting, and mice with the tumor volume ranging from 70-71 mm$^3$ were selected and randomly divided into groups by tumor volume.

Treatment:

The following antibodies were injected subcutaneously in various groups:

(1) human IgG (equitech-Bio), 20 mg/kg;
(2) LAG-3 (ADI-31853), 10 mg/kg;
(3) PD-L1 (HZ3266-IgG1N297A), 10 mg/kg;
(4) LAG-3 (ADI-31853), 10 mg/kg+PD-L1 (HZ3266-IgG1N297A), 10 mg/kg.

On the 7th day after grafting, the mice with average tumor sizes meeting the requirements were randomly grouped with 8 mice per group. The mice in each group were administrated with the four regimens on Days 7, 10, 14 and 17 at the above doses respectively.

Analysis: The tumor volume and body weight were measured twice a week throughout the study, and the mice were euthanized when the tumors reached the endpoint or when the mice had more than 20% of weight loss. The maximum length of major axis (L) and maximum length of minor axis (W) of tumors were measured with a vernier caliper, and tumor volume was calculated using the following formula: $V=L \times W^2/2$. The tumor volume over time of the mice in various group was plotted. Statistical significance was determined using analysis of variance (ANOVA). A P value below 0.05 was considered statistically significant in all analyses.

Figure 7:
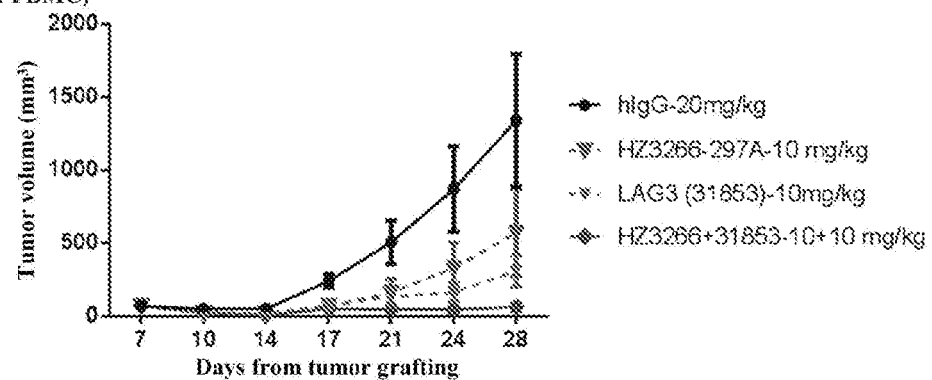
FIG. 7 shows the inhibitory effect of the antibody of the invention in combination with an anti-LAG-3 antibody.

As shown in FIG. 7, it can be seen that the combined use of the anti-LAG-3 monoclonal antibody ADI-31853 (31853) and the anti-PD-L1 monoclonal antibody (HZ3266-IgG1N297A) (HZ 3266) significantly inhibited tumor growth compared to the use of a human IgG control (equitech-Bio) (hIgG) and the separate use of the two antibodies.

The invention claimed is:

1. An antibody or antigen-binding fragment thereof that binds to PD-L1, wherein the antibody or antigen-binding fragment thereof comprises:
   (i) three heavy chain complementary determining regions (HCDRs) of a heavy chain variable region shown in SEQ ID NO: 26 or 30, and three light chain complementary determining regions (LCDRs) of a light chain variable region shown in SEQ ID NO: 32 or 36;
   (ii) three heavy chain complementary determining regions (HCDRs) of a heavy chain variable region shown in SEQ ID NO: 27, and three light chain complementary determining regions (LCDRs) of a light chain variable region shown in SEQ ID NO: 33;
   (iii) three heavy chain complementary determining regions (HCDRs) of a heavy chain variable region shown in SEQ ID NO: 28, and three light chain complementary determining regions (LCDRs) of a light chain variable region shown in SEQ ID NO: 34; or
   (iv) three heavy chain complementary determining regions (HCDRs) of a heavy chain variable region shown in SEQ ID NO: 29 or 31, and three light chain complementary determining regions (LCDRs) of a light chain variable region shown in SEQ ID NO: 35 or 37.

2. The antibody or antigen-binding fragment thereof of claim 1, the antibody or antigen-binding fragment thereof comprising a light chain variable region and a heavy chain variable region, wherein
   (i) the heavy chain variable region comprises an amino acid sequence having at least 90% identity to an amino acid sequence of SEQ ID NO: 26 or 30; and
   the light chain variable region comprises an amino acid sequence having at least 90% identity to an amino acid sequence of SEQ ID NO: 32 or 36;
   (ii) the heavy chain variable region comprises an amino acid sequence having at least 90% identity to an amino acid sequence of SEQ ID NO: 27; and
   the light chain variable region comprises an amino acid sequence having at least 90% identity to an amino acid sequence of SEQ ID NO: 33;
   (iii) the heavy chain variable region comprises an amino acid sequence having at least 90% identity to an amino acid sequence of SEQ ID No: 28; and
   the light chain variable region comprises an amino acid sequence having at least 90% identity to an amino acid sequence of SEQ ID NO: 34; or
   (iv) the heavy chain variable region comprises an amino acid sequence having at least 90% identity to an amino acid sequence of SEQ ID NO: 29 or 31; and
   the light chain variable region comprises an amino acid sequence having at least 90% identity to an amino acid sequence of SEQ ID NO: 35 or 37.

3. The antibody or antigen-binding fragment thereof of claim 1, the antibody or antigen-binding fragment thereof comprising a light chain variable region and a heavy chain variable region, wherein
   (i) the heavy chain variable region comprises an amino acid sequence of SEQ ID NO: 26 or 30; and
   the light chain variable region comprises an amino acid sequence of SEQ ID NO: 32 or 36;
   (ii) the heavy chain variable region comprises an amino acid sequence of SEQ ID NO: 27; and
   the light chain variable region comprises an amino acid sequence of SEQ ID NO: 33;
   (iii) the heavy chain variable region comprises an amino acid sequence of SEQ ID NO: 28; and
   the light chain variable region comprises an amino acid sequence of SEQ ID NO: 34; or
   (iv) the heavy chain variable region comprises an amino acid sequence of SEQ ID NO: 29 or 31; and
   the light chain variable region comprises an amino acid sequence of SEQ ID NO: 35 or 37.

4. The antibody or antigen-binding fragment thereof of claim 1, the antibody or antigen-binding fragment thereof comprising:
   (a) a heavy chain comprising an amino acid sequence having at least 85% identity to an amino acid sequence of SEQ ID NO: 38, 42, 43, or 44;
   and
   a light chain comprising an amino acid sequence having at least 85% identity to an amino acid sequence of SEQ ID NO: 46 or 50;
   (b) a heavy chain comprising an amino acid sequence having at least 85% identity to an amino acid sequence of SEQ ID NO: 39;
   and
   a light chain comprising an amino acid sequence having at least 85% identity to an amino acid sequence of SEQ ID NO: 47;
   (c) a heavy chain comprising an amino acid sequence having at least 85% identity to an amino acid sequence of SEQ ID NO: 40;
   and
   a light chain comprising an amino acid sequence having at least 85% identity to an amino acid sequence of SEQ ID NO: 48; or
   (d) a heavy chain comprising an amino acid sequence having at least 85% identity to an amino acid of SEQ ID NO: 41 or 45;
   and
   a light chain comprising an amino acid sequence having at least 85% identity to an amino acid sequence of SEQ ID NO: 49 or 51.

5. The antibody or antigen-binding fragment thereof of claim 1, wherein the antibody is an IgG1 or IgG4 antibody.

6. The antibody or antigen-binding fragment thereof of claim 1, wherein the antibody is a monoclonal antibody.

7. The antibody or antigen-binding fragment thereof of claim 1, wherein the antibody is a humanized antibody or a chimeric antibody.

8. The antibody or antigen-binding fragment thereof of claim 1, wherein the antigen-binding fragment is Fab, Fab', Fab'-SH, Fv, a single-chain antibody, scFv, a (Fab')$_2$ fragment, a diabody (dAb), or a linear antibody.

9. The antibody or antigen-binding fragment thereof of claim 1, wherein the antibody is a bispecific or multispecific antibody.

10. An isolated nucleic acid encoding
an antibody or antigen-binding fragment thereof that binds to PD-L1, wherein the antibody or antigen-binding fragment thereof comprises:
(i) three heavy chain complementary determining regions (HCDRs) of a heavy chain variable region shown in SEQ ID NO: 26 or 30, and three light chain complementary determining regions (LCDRs) of a light chain variable region shown in SEQ ID NO: 32 or 36;
(ii) three heavy chain complementary determining regions (HCDRs) of a heavy chain variable region shown in SEQ ID NO: 27, and three light chain complementary determining regions (LCDRs) of a light chain variable region shown in SEQ ID NO: 33;
(iii) three heavy chain complementary determining regions (HCDRs) of a heavy chain variable region shown in SEQ ID NO: 28, and three light chain complementary determining regions (LCDRs) of a light chain variable region shown in SEQ ID NO: 34; or
(iv) three heavy chain complementary determining regions (HCDRs) of a heavy chain variable region shown in SEQ ID NO: 29 or 31, and three light chain complementary determining regions (LCDRs) of a light chain variable region shown in SEQ ID NO: 35 or 37.

11. A vector comprising the nucleic acid of claim 10, wherein the vector is an expression vector.

12. A host cell comprising the nucleic acid of claim 10, wherein the host cell is a 293 cell or CHO cell.

13. A method for preparing an antibody or antigen-binding fragment thereof that binds to PD-L1, the method comprising incubating the host cell of claim 12 in conditions suitable for expression of a nucleic acid encoding an antibody or antigen-binding fragment thereof; and isolating the antibody or antigen-binding fragment thereof.

14. An immunoconjugate, comprising the antibody or antigen-binding fragment thereof of claim 1, and a cytotoxic agent.

15. A pharmaceutical composition, comprising the antibody or antigen-binding fragment thereof of claim 1, and a pharmaceutical carrier.

16. A pharmaceutical composition, comprising the antibody or antigen-binding fragment thereof of claim 1, and an additional therapeutic agent, wherein the additional therapeutic agent is selected from the group consisting of chemotherapeutic agents, antibodies, an anti-LAG-3 antibody, cytotoxic agents, vaccines, anti-infection active agents, and immunomodulatory agents.

17. The pharmaceutical composition of claim 16, wherein the anti-LAG-3 antibody comprises:
(i) three heavy chain complementarity determining regions (HCDRs) of the heavy chain variable region shown in SEQ ID NO: 75, and
(ii) three light chain complementarity determining regions (LCDRs) of the light chain variable region shown in SEQ ID NO: 76.

18. The pharmaceutical composition of claim 16, wherein the anti-LAG-3 antibody comprises a heavy chain variable region (VH) and a light chain variable region (VL), wherein
(i) the VH comprises heavy chain complementarity determining regions (CDRs) HCDR1, HCDR2 and HCDR3, wherein the HCDR1 comprises an amino acid sequence of SEQ ID NO: 69; the HCDR2 comprises an amino acid sequence of SEQ ID NO: 70; and the HCDR3 comprises an amino acid sequence of SEQ ID NO: 71; and
(ii) the VL comprises light chain complementarity determining regions (CDRs) LCDR1, LCDR2, and LCDR3, wherein the LCDR1 comprises an amino acid sequence of SEQ ID NO: 72; the LCDR2 comprises an amino acid sequence of SEQ ID NO: 73; and the LCDR3 comprises an amino acid sequence of SEQ ID NO: 74.

19. A method of preventing or treating a tumor or an infectious disease in a subject in need thereof, the method comprising administering an effective amount of the antibody or antigen-binding fragment thereof of claim 1 to the subject.

20. A method of preventing or treating a tumor or an infectious disease in a subject in need thereof, the method comprising administering an effective amount of the antibody or antigen-binding fragment thereof of claim 1 and an effective amount of an anti-LAG-3 antibody to the subject.

21. The method of claim 19, wherein the tumor is a cancer, a gastrointestinal tract tumor, a gastrointestinal tract cancer, or a colon cancer; or the infectious disease is a chronic infection.

22. The method of claim 19, wherein the antibody or antigen-binding fragment thereof is administered in combination with one or more of additional therapies, wherein the one or more of additional therapies are therapeutic modalities or therapeutic agents, wherein the therapeutic modalities are surgical treatment or radiotherapy, wherein the therapeutic agents are selected from the group consisting of chemotherapeutic agents, cytotoxic agents, vaccines, anti-infection active agents, antibodies, and immunomodulatory agents.

23. The method of claim 20, wherein the anti-LAG-3 antibody comprises:
(i) three heavy chain complementarity determining regions (HCDRs) of the heavy chain variable region shown in SEQ ID NO: 75, and
(ii) three light chain complementarity determining regions (LCDRs) of the light chain variable region shown in SEQ ID NO: 76.

24. The method of claim 20, wherein the anti-LAG-3 antibody comprises a heavy chain variable region (VH) and a light chain variable region (VL), wherein
(i) the VH comprises heavy chain complementarity determining regions (CDRs) HCDR1, HCDR2 and HCDR3, wherein the HCDR1 comprises an amino acid sequence of SEQ ID NO: 69; the HCDR2 comprises an amino acid sequence of SEQ ID NO: 70; and the HCDR3 comprises an amino acid sequence of SEQ ID NO: 71; and
(ii) the VL comprises light chain complementarity determining regions (CDRs) LCDR1, LCDR2, and LCDR3, wherein the LCDR1 comprises an amino acid sequence of SEQ ID NO: 72; the LCDR2 comprises an amino acid sequence of SEQ ID NO: 73; and the LCDR3 comprises an amino acid sequence of SEQ ID NO: 74.

25. The antibody or antigen-binding fragment thereof of claim 1, wherein the antibody or antigen-binding fragment thereof comprises three heavy chain complementary determining regions (HCDRs) of a heavy chain variable region shown in SEQ ID NO: 26 or 30, and three light chain complementary determining regions (LCDRs) of a light chain variable region shown in SEQ ID NO: 32 or 36.

26. The antibody or antigen-binding fragment thereof of claim 1, wherein the antibody or antigen-binding fragment thereof comprises three heavy chain complementary determining regions (HCDRs) of a heavy chain variable region shown in SEQ ID NO: 27, and three light chain complementary determining regions (LCDRs) of a light chain variable region shown in SEQ ID NO: 33.

27. The antibody or antigen-binding fragment thereof of claim 1, wherein the antibody or antigen-binding fragment thereof comprises three heavy chain complementary determining regions (HCDRs) of a heavy chain variable region shown in SEQ ID NO: 28, and three light chain complementary determining regions (LCDRs) of a light chain variable region shown in SEQ ID NO: 34.

28. The antibody or antigen-binding fragment thereof of claim 1, wherein the antibody or antigen-binding fragment thereof comprises three heavy chain complementary determining regions (HCDRs) of a heavy chain variable region shown in SEQ ID NO: 29 or 31, and three light chain complementary determining regions (LCDRs) of a light chain variable region shown in SEQ ID NO: 35 or 37.

29. The antibody or antigen-binding fragment thereof of claim 2, wherein the heavy chain variable region comprises an amino acid sequence of SEQ ID NO: 26 or 30; and the light chain variable region comprises an amino acid sequence of SEQ ID NO: 32 or 36.

30. The antibody or antigen-binding fragment thereof of claim 2, wherein the heavy chain variable region comprises an amino acid sequence of SEQ ID NO: 27; and the light chain variable region comprises an amino acid sequence of SEQ ID NO: 33.

31. The antibody or antigen-binding fragment thereof of claim 2, wherein the heavy chain variable region comprises an amino acid sequence of SEQ ID No: 28; and the light chain variable region comprises an amino acid sequence of SEQ ID NO: 34.

32. The antibody or antigen-binding fragment thereof of claim 2, wherein the heavy chain variable region comprises an amino acid sequence of SEQ ID NO: 29 or 31; and the light chain variable region comprises an amino acid sequence of SEQ ID NO: 35 or 37.

33. An antibody or antigen-binding fragment thereof that binds to PD-L1, wherein the antibody or antigen-binding fragment thereof comprises:
a heavy chain variable region (VH) comprising heavy chain complementary determining regions (HCDRs) 1, 2, and 3, wherein the HCDR1 region comprises an amino acid sequence that is identical to a selected HCDR1 amino acid sequence, the HCDR2 region comprises an amino acid sequence that is identical to a selected HCDR2 amino acid sequence, and the HCDR3 region comprises an amino acid sequence that is identical to a selected HCDR3 amino acid sequence; and
a light chain variable region (VL) comprising light chain complementary determining regions (LCDRs) 1, 2, and 3, wherein the LCDR1 region comprises an amino acid sequence that is identical to a selected LCDR1 amino acid sequence, the LCDR2 region comprises an amino acid sequence that is identical to a selected LCDR2 amino acid sequence, and the LCDR3 region comprises an amino acid sequence that is identical to a selected LCDR3 amino acid sequence;
wherein the selected HCDRs 1, 2, and 3 amino acid sequences and the selected LCDRs 1, 2, and 3 amino acid sequences are one of the following:
(1) the selected HCDRs 1, 2, 3 amino acid sequences are set forth in SEQ ID NOs: 1, 5, 10, respectively, and the selected LCDRs 1, 2, 3 amino acid sequences are set forth in SEQ ID NOs: 14, 17, 21, respectively;
(2) the selected HCDRs 1, 2, 3 amino acid sequences are set forth in SEQ ID NOs: 2, 6, 11, respectively, and the selected LCDRs 1, 2, 3 amino acid sequences are set forth in SEQ ID NOs: 15, 18, 22, respectively;
(3) the selected HCDRs 1, 2, 3 amino acid sequences are set forth in SEQ ID NOs: 2, 7, 12, respectively, and the selected LCDRs 1, 2, 3 amino acid sequences are set forth in SEQ ID NOs: 15, 18, 23, respectively; and
(4) the selected HCDRs 1, 2, 3 amino acid sequences are set forth in SEQ ID NOs: 3, 8, 13, respectively, and the selected LCDRs 1, 2, 3 amino acid sequences are set forth in SEQ ID NOs: 16, 19, 24, respectively.

34. The antibody or antigen-binding fragment thereof of claim 33, wherein the selected HCDRs 1, 2, 3 amino acid sequences are set forth in SEQ ID NOs: 1, 5, 10, respectively, and the selected LCDRs 1, 2, 3 amino acid sequences are set forth in SEQ ID NOs: 14, 17, 21, respectively.

35. The antibody or antigen-binding fragment thereof of claim 33, wherein the selected HCDRs 1, 2, 3 amino acid sequences are set forth in SEQ ID NOs: 2, 6, 11, respectively, and the selected LCDRs 1, 2, 3 amino acid sequences are set forth in SEQ ID NOs: 15, 18, 22, respectively.

36. The antibody or antigen-binding fragment thereof of claim 33, wherein the selected HCDRs 1, 2, 3 amino acid sequences are set forth in SEQ ID NOs: 2, 7, 12, respectively, and the selected LCDRs 1, 2, 3 amino acid sequences are set forth in SEQ ID NOs: 15, 18, 23, respectively.

37. The antibody or antigen-binding fragment thereof of claim 33, wherein the selected HCDRs 1, 2, 3 amino acid sequences are set forth in SEQ ID NOs: 3, 8, 13, respectively, and the selected LCDRs 1, 2, 3 amino acid sequences are set forth in SEQ ID NOs: 16, 19, 24, respectively.

* * * * *